(12) United States Patent
Fefer et al.

(10) Patent No.: US 9,750,249 B2
(45) Date of Patent: *Sep. 5, 2017

(54) SYNERGISTIC PARAFFINIC OIL AND BOSCALID FUNGICIDES

(71) Applicant: Suncor Energy Inc., Calgary (CA)

(72) Inventors: Michael Fefer, Whitby (CA); Jun Liu, Oakville (CA)

(73) Assignee: Suncor Energy Inc., Calgary, Alberta (CA)

( * ) Notice: Subject to any disclaimer, the term of this patent is extended or adjusted under 35 U.S.C. 154(b) by 14 days.

This patent is subject to a terminal disclaimer.

(21) Appl. No.: 14/950,579

(22) Filed: Nov. 24, 2015

(65) Prior Publication Data

US 2016/0150783 A1  Jun. 2, 2016

Related U.S. Application Data

(63) Continuation of application No. 13/821,808, filed as application No. PCT/CA2011/001018 on Sep. 9, 2011, now Pat. No. 9,226,504.

(60) Provisional application No. 61/381,179, filed on Sep. 9, 2010.

(51) Int. Cl.
| A01N 43/40 | (2006.01) |
| A01N 27/00 | (2006.01) |
| A01N 61/02 | (2006.01) |
| A01N 25/30 | (2006.01) |
| A01P 3/00 | (2006.01) |

(52) U.S. Cl.
CPC ............ *A01N 43/40* (2013.01); *A01N 27/00* (2013.01)

(58) Field of Classification Search
None
See application file for complete search history.

(56) References Cited

U.S. PATENT DOCUMENTS

| 2,714,062 A | 7/1955 | Lockrey et al. |
| 2,786,821 A | 3/1957 | Gardner et al. |
| 2,870,037 A | 1/1959 | Converse et al. |
| 3,113,066 A | 12/1963 | Edmond |
| 3,131,119 A | 4/1964 | Fordyce et al. |
| 3,426,126 A | 2/1969 | Thorne et al. |
| 3,615,799 A | 10/1971 | Gannon et al. |
| 3,689,574 A | 9/1972 | Engelhart |
| 3,799,758 A | 3/1974 | Franz |
| 3,948,635 A | 4/1976 | Vachette et al. |
| 3,950,265 A | 4/1976 | Albrecht et al. |
| 3,997,322 A | 12/1976 | Ratledge |
| 4,002,628 A | 1/1977 | Benefiel et al. |
| 4,015,970 A | 4/1977 | Hennart |
| 4,041,164 A | 8/1977 | Albrecht et al. |
| 4,094,845 A | 6/1978 | De Long |
| 4,124,720 A | 11/1978 | Wenmaekers |
| 4,243,405 A | 1/1981 | Balasubramanyan et al. |
| 4,431,554 A | 2/1984 | Baur |
| 4,584,013 A | 4/1986 | Brunner |
| 4,618,360 A | 10/1986 | Brunner |
| 4,693,745 A | 9/1987 | Brunner |
| 4,698,334 A | 10/1987 | Horriere et al. |
| 4,734,432 A | 3/1988 | Szego et al. |
| 4,737,515 A | 4/1988 | Hallenbach et al. |
| 4,761,423 A | 8/1988 | Szego et al. |
| 4,826,863 A | 5/1989 | Szego et al. |
| 4,834,908 A | 5/1989 | Hazen et al. |
| 4,853,026 A | 8/1989 | Frisch et al. |
| 4,902,333 A | 2/1990 | Quimby, Jr. |
| 4,971,840 A | 11/1990 | Boho et al. |
| 5,084,087 A | 1/1992 | Hazen et al. |
| 5,102,442 A | 4/1992 | Hazen et al. |
| 5,137,726 A | 8/1992 | Ogawa |
| 5,178,795 A | 1/1993 | Roberts |
| 5,229,356 A | 7/1993 | Tocker |
| 5,238,604 A | 8/1993 | Hazen et al. |
| 5,308,827 A | 5/1994 | Sakamoto et al. |
| 5,330,995 A | 7/1994 | Eicken et al. |
| 5,336,661 A | 8/1994 | Lucas |
| 5,352,729 A | 10/1994 | Birkhofer et al. |
| 5,362,167 A | 11/1994 | Loftin |
| 5,393,770 A | 2/1995 | Grayson |
| 5,393,791 A | 2/1995 | Roberts |
| 5,409,885 A | 4/1995 | Derian et al. |
| 5,504,054 A | 4/1996 | Murphy |
| 5,547,918 A | 8/1996 | Newton et al. |
| 5,558,806 A | 9/1996 | Policello et al. |

(Continued)

FOREIGN PATENT DOCUMENTS

| CA | 964482 | 3/1975 |
| CA | 2069311 | 4/1991 |
| CA | 2434848 | 8/2002 |
| CA | 2507482 | 5/2005 |
| CA | 2496142 | 8/2005 |

(Continued)

OTHER PUBLICATIONS

U.S. Appl. No. 14/376,006, filed Jul. 31, 2014, Liu et al.
U.S. Appl. No. 15/074,919, filed Mar. 18, 2016.
"Addendum 9. Northeastern Collegiate Weed Science Contest Weed, Crop, and Herbicide Lists," revised May 2007. Retrieved from the Internet: <URL: http://www.newss.org/docs/mop/addendum-9.pdf>, 7 pages.

(Continued)

*Primary Examiner* — Abigail Fisher
(74) *Attorney, Agent, or Firm* — Fish & Richardson P.C.

(57) ABSTRACT

Fungicidal compositions comprising a paraffinic oil and 2-chloro-N-(4'-chloro[1,1'-biphenyl]-2-yl)-3-pyridinecarboxamide (boscalid) are provided. The fungicidal compositions may further comprise a pigment. The fungicidal compositions may be provided as oil-in-water (O/W) emulsions which may be used for controlling fungal disease, such as dollar spot or bentgrass dead spot or bermudagrass dead spot, in plants, such as turfgrasses. Methods of applying the fungicidal compositions are also provided.

20 Claims, No Drawings

(56) References Cited

U.S. PATENT DOCUMENTS

| | | |
|---|---|---|
| 5,580,567 A | 12/1996 | Roberts |
| 5,599,768 A | 2/1997 | Hermansky |
| 5,599,804 A | 2/1997 | Mudge |
| 5,643,852 A | 7/1997 | Lucas et al. |
| 5,658,851 A | 8/1997 | Murphy et al. |
| 5,665,672 A | 9/1997 | Lucas |
| 5,668,086 A | 9/1997 | Tadayuki et al. |
| 5,703,016 A | 12/1997 | Magin et al. |
| 5,739,371 A | 4/1998 | O'Lenick, Jr. |
| 5,741,502 A | 4/1998 | Roberts |
| 5,919,858 A | 7/1999 | Loftin |
| 5,958,104 A | 9/1999 | Nonomura et al. |
| 5,989,331 A | 11/1999 | Bauer et al. |
| 6,033,647 A | 3/2000 | Touzan et al. |
| 6,117,820 A | 9/2000 | Cutler et al. |
| 6,146,652 A | 11/2000 | Gore et al. |
| 6,159,900 A | 12/2000 | Bieringer et al. |
| 6,162,763 A | 12/2000 | Tateno |
| 6,210,656 B1 | 4/2001 | Touzan et al. |
| 6,221,811 B1 | 4/2001 | Policello et al. |
| 6,329,321 B2 | 12/2001 | Okura et al. |
| 6,403,061 B1 | 6/2002 | Candau et al. |
| 6,416,748 B1 | 7/2002 | Candau et al. |
| 6,432,877 B2 | 8/2002 | Okura et al. |
| 6,515,031 B2 | 2/2003 | Fefer |
| 6,673,360 B2 | 1/2004 | Fefer |
| 6,683,030 B2 | 1/2004 | Kober et al. |
| 6,713,518 B1 | 3/2004 | Bessette et al. |
| 6,727,205 B2 | 4/2004 | Brinkman |
| 6,734,202 B2 | 5/2004 | Cotter et al. |
| 6,803,345 B2 | 10/2004 | Herold et al. |
| 6,878,674 B2 | 4/2005 | Kobayashi |
| 6,972,273 B2 | 12/2005 | Sedun et al. |
| 7,135,435 B2 | 11/2006 | Cooper et al. |
| 7,166,725 B2 | 1/2007 | Fang et al. |
| 7,799,343 B2 | 9/2010 | Loughner |
| 7,923,452 B2 | 4/2011 | Birner et al. |
| RE42,394 E | 5/2011 | Mudge |
| 8,076,267 B2 | 12/2011 | Diebold et al. |
| 8,298,990 B2 | 10/2012 | Wu et al. |
| 8,426,343 B2 | 4/2013 | Norton et al. |
| 8,569,210 B2 | 10/2013 | Fefer et al. |
| 8,747,874 B2 | 6/2014 | Fefer |
| 8,748,342 B2 | 6/2014 | Gewehr et al. |
| 8,853,128 B2 | 10/2014 | Fefer et al. |
| 9,044,008 B2 | 6/2015 | Fefer |
| 9,226,504 B2 | 1/2016 | Fefer et al. |
| 9,357,768 B2 | 6/2016 | Fefer et al. |
| 9,451,773 B2 | 9/2016 | Fefer et al. |
| 9,485,988 B2 | 11/2016 | Fefer et al. |
| 2001/0019728 A1 | 9/2001 | Basinger et al. |
| 2001/0044381 A1 | 11/2001 | Dean |
| 2002/0161057 A1 | 10/2002 | Fefer |
| 2003/0087764 A1 | 5/2003 | Pallas et al. |
| 2003/0185754 A1 | 10/2003 | Cohen et al. |
| 2003/0187079 A1 | 10/2003 | Fefer |
| 2003/0194454 A1 | 10/2003 | Bessette et al. |
| 2003/0198659 A1 | 10/2003 | Hoffmann et al. |
| 2003/0198696 A1 | 10/2003 | Keen |
| 2004/0132621 A1 | 7/2004 | Frisch et al. |
| 2004/0132622 A1 | 7/2004 | Stewart |
| 2004/0151749 A1 | 8/2004 | Hasebe et al. |
| 2004/0167034 A1 | 8/2004 | Coote et al. |
| 2004/0192556 A1 | 9/2004 | Schregenberger et al. |
| 2005/0026786 A1 | 2/2005 | Deckwer et al. |
| 2005/0181949 A1 | 8/2005 | Norton et al. |
| 2005/0202102 A1 | 9/2005 | Miller |
| 2005/0233907 A1 | 10/2005 | Nabors et al. |
| 2005/0261379 A1 | 11/2005 | Fefer |
| 2005/0274164 A1 | 12/2005 | Coates et al. |
| 2006/0063676 A1 | 3/2006 | Brigance et al. |
| 2006/0068991 A1 | 3/2006 | Norton et al. |
| 2006/0194699 A1 | 8/2006 | Moucharafleh et al. |
| 2006/0276339 A1 | 12/2006 | Windsor et al. |
| 2006/0282961 A1 | 12/2006 | Hughes |
| 2006/0293188 A1 | 12/2006 | Norton et al. |
| 2007/0184005 A1 | 8/2007 | Policello et al. |
| 2007/0197386 A1 | 8/2007 | Diebold et al. |
| 2007/0197387 A1 | 8/2007 | Polge |
| 2007/0287720 A1 | 12/2007 | Royalty et al. |
| 2008/0064601 A1 | 3/2008 | Casanello et al. |
| 2008/0085832 A1 | 4/2008 | Fefer et al. |
| 2008/0112909 A1 | 5/2008 | Faler et al. |
| 2008/0153702 A1 | 6/2008 | Voeste et al. |
| 2008/0161367 A1 | 7/2008 | Voeste et al. |
| 2008/0194704 A1 | 8/2008 | Bhatnagar et al. |
| 2008/0274888 A1 | 11/2008 | Goldstein |
| 2008/0280763 A1 | 11/2008 | Hodge et al. |
| 2008/0293567 A1 | 11/2008 | Birner et al. |
| 2009/0092986 A1 | 4/2009 | Taing et al. |
| 2009/0325922 A1 | 12/2009 | Fefer et al. |
| 2010/0016447 A1 | 1/2010 | Fefer |
| 2010/0099567 A1 | 4/2010 | Shinichi |
| 2010/0310617 A1 | 12/2010 | Zhang et al. |
| 2010/0317527 A1 | 12/2010 | Takeuchi et al. |
| 2011/0275516 A1 | 11/2011 | Wu et al. |
| 2011/0306495 A1 | 12/2011 | Sanaraheewa et al. |
| 2012/0245232 A1 | 9/2012 | Bousque et al. |
| 2013/0303374 A1 | 11/2013 | Fefer et al. |
| 2014/0107070 A1 | 4/2014 | Fefer et al. |
| 2014/0228218 A1 | 8/2014 | Fefer et al. |
| 2014/0256556 A1 | 9/2014 | Fefer et al. |
| 2015/0065475 A1 | 3/2015 | Fefer et al. |
| 2015/0237869 A1 | 8/2015 | Fefer |
| 2015/0305329 A1 | 10/2015 | Fefer |
| 2016/0198723 A1 | 7/2016 | Fefer |
| 2016/0286801 A1 | 10/2016 | Liu et al. |
| 2017/0071201 A1 | 3/2017 | Fefer et al. |

FOREIGN PATENT DOCUMENTS

| | | |
|---|---|---|
| CA | 2472806 | 11/2005 |
| CA | 2568817 | 12/2005 |
| CA | 2209920 | 1/2007 |
| CA | 2562718 | 4/2008 |
| CA | 2605092 | 4/2008 |
| CA | 2625415 | 9/2008 |
| CA | 2711660 | 7/2009 |
| CA | 2748084 | 7/2010 |
| CN | 101238820 | 8/2008 |
| CN | 101304658 | 11/2008 |
| CN | 101390517 | 3/2009 |
| CN | 101415327 | 4/2009 |
| CN | 101473849 | 7/2009 |
| CN | 101998827 | 3/2011 |
| CN | 101773113 | 2/2013 |
| DE | 2511077 | 9/1976 |
| EP | 0267778 | 5/1988 |
| EP | 0498231 | 8/1992 |
| EP | 0526206 | 2/1993 |
| EP | 0598515 | 5/1994 |
| EP | 0862857 | 9/1998 |
| EP | 1563734 | 8/2005 |
| EP | 2319484 | 5/2011 |
| GB | 191208748 | 4/1913 |
| GB | 745360 | 2/1956 |
| GB | 747909 | 4/1956 |
| GB | 748422 | 5/1956 |
| GB | 753976 | 8/1956 |
| GB | 758926 | 10/1956 |
| GB | 762866 | 12/1956 |
| GB | 763246 | 12/1956 |
| GB | 765459 | 1/1957 |
| GB | 792045 | 3/1958 |
| GB | 1044895 | 10/1966 |
| GB | 1168913 | 10/1969 |
| GB | 1249674 | 10/1971 |
| GB | 1417364 | 12/1975 |
| GB | 1499397 | 2/1978 |
| GB | 2123819 | 2/1984 |
| GB | 2176493 | 12/1986 |
| JP | 50-063141 | 5/1975 |
| JP | 54-036205 | 11/1979 |
| JP | 55-129213 | 10/1980 |

(56) References Cited

FOREIGN PATENT DOCUMENTS

| | | |
|---|---|---|
| JP | 57-028184 | 2/1982 |
| JP | 59-067205 | 4/1984 |
| JP | 59-210007 | 11/1984 |
| JP | S62-240601 | 10/1987 |
| JP | 2-138376 | 5/1990 |
| JP | 3-183505 | 8/1991 |
| JP | 3-221576 | 9/1991 |
| JP | 4-128003 | 4/1992 |
| JP | 07-179306 | 7/1995 |
| JP | 8-218225 | 8/1996 |
| JP | 10-029901 | 2/1998 |
| JP | 11-137084 | 5/1999 |
| JP | 11-349588 | 12/1999 |
| JP | 2006-124337 | 5/2006 |
| JP | 2008-502640 | 1/2008 |
| NL | 8900381 | 9/1990 |
| SU | 1021415 | 6/1983 |
| WO | WO 9007272 | 7/1990 |
| WO | WO 9312175 | 6/1993 |
| WO | WO 9621353 | 7/1996 |
| WO | WO 9632010 | 10/1996 |
| WO | WO 9632011 | 10/1996 |
| WO | WO 9835561 | 8/1998 |
| WO | WO 0064257 | 11/2000 |
| WO | WO 0221913 | 3/2002 |
| WO | WO 0234047 | 5/2002 |
| WO | WO 02089573 | 11/2002 |
| WO | WO 02096199 | 12/2002 |
| WO | WO 03047558 | 6/2003 |
| WO | WO 03101195 | 12/2003 |
| WO | WO 03105587 | 12/2003 |
| WO | WO 2004030641 | 4/2004 |
| WO | WO 2004080177 | 9/2004 |
| WO | WO 2005009132 | 2/2005 |
| WO | WO 2005018324 | 3/2005 |
| WO | WO 2005055716 | 6/2005 |
| WO | WO 2005082137 | 9/2005 |
| WO | WO 2006126211 | 11/2006 |
| WO | WO 2007054473 | 3/2007 |
| WO | WO 2007117720 | 10/2007 |
| WO | WO 2007136597 | 11/2007 |
| WO | WO 2008014185 | 1/2008 |
| WO | WO 2008020872 | 2/2008 |
| WO | WO 2008030753 | 3/2008 |
| WO | WO 2008049192 | 5/2008 |
| WO | WO 2008069990 | 6/2008 |
| WO | WO 2008073397 | 6/2008 |
| WO | WO 2009080428 | 7/2009 |
| WO | WO 2009090181 | 7/2009 |
| WO | WO 2009098223 | 8/2009 |
| WO | WO 2009126370 | 10/2009 |
| WO | WO 2009139106 | 11/2009 |
| WO | WO 2009155693 | 12/2009 |
| WO | WO 2010043447 | 4/2010 |
| WO | WO 2010132169 | 11/2010 |
| WO | WO 2011028987 | 3/2011 |
| WO | WO 2011070503 | 6/2011 |
| WO | WO 2012031355 | 3/2012 |
| WO | WO 2012040804 | 4/2012 |
| WO | WO 2012055991 | 5/2012 |
| WO | WO 2012126094 | 9/2012 |
| WO | WO 2012162844 | 12/2012 |
| WO | WO 2012162846 | 12/2012 |
| WO | WO 2012171126 | 12/2012 |
| WO | WO 2013078546 | 6/2013 |
| WO | WO 2014139012 | 9/2014 |

OTHER PUBLICATIONS

"An Online Guide to Plant Disease Control," Oregon State University Extension, print 1954, web 1996. Retrieved from the Internet: <URL: http:/plant-disease.orst.edu/>, 7 pages.

"Auxin," Wikipedia [online]. Retrieved from the Internet: <URL: http://en.wikipedia.org/wiki/Auxin>, 12 pages, Retrieved on Apr. 9, 2015.

"Bentgmss Dead Spot: Ophiosphaerella agrostis," Cornell University, created Apr. 2001, updated Jan. 2015. Retrieved from the Internet: <URL: http://plantclinic.cornell.edu/factsheets/bentgrassdeadspot.pdf>, 2 pages.

"Biological/Biorational Products for Disease Management," University of Connecticut Integrated Pest Management, [online] Jan. 2006. Retrieved from the Internet: <URL: http://www.ipm.uconn.edu/ipm/greenhs/htms/biofung.htm>, 6 pages.

"Characteristics of Plant Growth Regulators used in Fine Turf," Clemson University, retrieved on Aug. 24, 2011. Retrieved from the Internet: <URL: http://www.clemson.edu/extension/horticulture/turf/pest-guidelines/2011-p- est-guidelines/plant growth-reg-201 1.pdf>, 9 pages.

"Chemical Update: Plant growth regulators," Grounds Maintenance [online] 2008. Retrieved from the Internet: <URL: http://www.grounds-mag.com/mag/grounds_maintenance_chemical_update_plant_6>, 2 pages.

"Civitas Technical Bulletin—Fungicide Resistance," Petro-Canada. Retrieved from the Internet: <URL: http://www.civitasturf.com/pdf/techBulletin.pdf>, 2 pages, 2009.

"Deformulation of RD 7212 Grazz Greenzit," 5 pages, 2009.

"Dollar Spot on Turfgrass," Cornell University, retrieved on Aug. 22, 2011. Retrieved from the Internet: <URL: http://counties.cce.cornell.edu/wyoming/agriculture/resources/ipd/dollar_spot_turfgrass.htm>, 3 pages.

"Emerald® Fungicide a Better Standard for Dollar Spot Control," Jan. 1, 2007 [retrieved on Jan. 14, 2014]. Retrieved from the Internet <URL: http://betterturf.basf.us/products/related-documents/emerald-info-sheet.pdf>, 2 pages.

"Food, Crop & Livestock Safety: Phytotoxicity," British Columbia Ministry of Agriculture. Archived Oct. 27, 2005. Retrieved from the Internet: <URL: http://www.agf.gov.bc.ca/pesticides/e_10.htm>, 2 pages.

"Fungicide Synergy," Kansas State University, Feb. 26, 2009. Retrieved from the Internet: <URL: http://www.ksuturf.com/LISTServArchive/2009-02-26-Fungicide-Synergy.pdf>, 3 pages.

"Gray leaf spot of perennial ryegrass," Kansas State University Turfgrass Research, 4 pages, revised Aug. 2008.

"Heat Stress Study Using Greenzit Pigment," University of Guelph, 3 pages, 2009.

"Herbicide Recommendations for Turfgrass: Postemergence Broadleaf Herbicides," Ontario Ministry of Agriculture, Food and Rural Affairs, Nov. 25, 2002, reviewed May 15, 2006. Retreived from the Internet: <URL: http://www.omafra.gov.on.ca/english/crops/pub75/17turpbh.htm>, 7 pages.

"Herbicide," Wikipedia [online], retrieved on Aug. 29, 2006. Retrieved from the Internet: <http://en.wikipedia.org/wiki/Herbicide>, 5 pages.

"Horticultural Oils," IPM of Alaska [online] retrieved on Apr. 5, 2005. Retrieved from the Internet: <URL: http:/www.ipmofalaska.com/filed/hortoils.html>, 3 pages.

"Inert (other) Pesticide Ingredients in Pesticide Products," U.S. Environment Protection Agency, retrieved Sep. 11, 2007. Retrieved from the Internet: <http://www.epa.gov/opprd001/inerts/lists.html> 3 pages.

"It pays to be pure," Retrieved from the Internet: <http://www.findarticles.com/p/articles/mi-qa3824/is-200405/ai-n9424665/print>, Meister Media Worldwide, 1 pages, May 2004.

"Kannar Product Range Turf Enhancing Products," 1 page. Retreived on Dec. 14, 2007. Retrieved from the Internet: <URL: http://web.archive.org/web/20040101182326/http:kannar.com/>, 1 page.

"Leaf Spot and Melting-out (crown and root rot) Diseases," Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/leaf-spot>, 2 pages.

(56) References Cited

OTHER PUBLICATIONS

"Performance of generic phosphite fungicides: A status report," AgNet Mar. 8, 2004, The Canadian Phytopathological Society, Retrieved from the Internet: <URL: http://www.cps-scp.ca/pathologynews/performanceofgenericfungicides.html>, 2 pages.

"Plant Growth Regulators for Turf, Landscape and Garden," Lawn Care Academy [online], retrieved Dec. 28, 2010. Retrieved from the Internet: <URL: http://www.lawn-care-academy.com/plant-growth-regulators.html>, 6 pages.

"The National Turfgrass Research Initiative: Enhancing America's Beauty Protecting America's Natural Resources Ensuring the Health and Safety of all Americans," Retrieved from the Internet: <URL: http://www.ntep.org/pdf/turfinitiative.pdf>, Apr. 2003, 22 pages.

"The Stylet-Oil User's Guide," Retrieved from the Internet: <URL: http://www.stylet-oil.com>, 15 pages. Retrieved on Mar. 22, 2005.

"Trinexapac-ethyl—Compound Summary," PubChem Public Chemical Database, [online] retrieved on Aug. 25, 2011. Retrieved from the Internet: <URL: http://pubchem.ncbi.nlm.nih.gov/summary/summary cgi?cid=92421&loc=ec_rcs>, 3 pages.

"Turf grass coloration using hexadentate cobalt phthalocyanine amine complex salts," AN-1976-74211X[40], p. 1, 1975.

"Turfgrass Diseases: Leaf Spots and Tip Blights, Melting Out, Crown and Root Rots," University of Rhode Island Landscape Horticulture Program, 2000. Retrieved from the Internet: <URL: http://www.uri.edu/ce/factsheets/prints/leafspotsetcprint.html>, 3 pages.

"Turfgrass Pest Management Manual: A Guide to Major Turfgrass Pests & Turfgrasses," North Carolina State University, Mar. 26, 2007. Retrieved from the Internet: <URL: http://www.turffiles.ncsu.edu/PDFFiles/004041/Turfgrass_Pest_Management_Manual_A_Guide_to_Major_Turfgrass_Pests_and_Turfgrasses.pdf>, 106 pages.

Aerosil 200, Evonik [online] <URL: http://www.aerosil.com/lpa-productrinder/page/productsbytext/detail.html?pid=1855&lang=en>, Jun. 19, 2012, 1 page.

Agnello, "Petroleum-derived spray oils: chemistry, history, refining and formulation," in Beattie, G.A.C., Watson, D.M., Stevens, M., Spooner-Hart, R. and Rae, D.J. (eds). Spray Oils Beyond 2000—Sustainable Pest & Disease Management. University of Western Sydney, 2002. Retrieved from the Internet: <URL: http://web.entomology.cornell.edu/agnello/assets/1-1_Agnello.pdf>, 17 pages.

Bakke, "Analysis of Issues Surrounding the Use of Spray Adjuvants with Herbicides," Dec. 2002, Revised Jan. 2007. Retrieved from the Internet: <URL: http://www.fs.usda.gov/Internet/FSE_DOCUMENTS/fsbdev3_045552.pdf>, 61 pages.

Beasley and Branham, "Trinexapac-ethyl and Paclobutrazol Affect Kentucky Bluegrass Single-Leaf Carbon Exchange Rates and Plant Growth," *Crop Sci.*, 47:132-138, Jan. 22, 2007.

Beckerman, "Disease Management Strategies for Horticultural Crops: Using Organic Fungicides," Purdue Extension, Apr. 1, 2008 [retrieved on Sep. 29, 2014]. Retrieved from the Internet: <URL: https://www.extension.purdue.edu/extmedia/bp/bp-69-w.pdf>, 4 pages.

Ben-Tal, "Effect of Chloro-Aluminum-Phtahalocyanine on the Growth of Lenma gibba G3," *J. Plant Physiol.*, 135(5):635-636, 1989.

Bigelow et al., "Evaluation of Commercially Available Plant Growth Regulator Programs for Creeping Bentgrass Fairway Management," Retrieved from the Internet: <URL: http://www.agry.purdue.edu/turf/report/2003/Page66.pdf>, pp. 66-74, 2003.

Biology and Control of Dollar Spot Disease, Ontario Ministry of Agriculture Food & Rural Affairs, Retrieved on Aug. 22, 2011. Retrieved from the Internet: <URL: http://www.omafra.gov.on.ca/english/crops/facts/info_turfdollarspot.htm>, 3 pages.

Blenis et al, "Evaluation of Fungicides and Surfactants for Control of Fairy Rings Caused by Marasmius oreades (Bolt ex. Fr.) Fr.," *HortScience*, 32(6):1077-1084, 1997.

Bradley, "Some ways in which a paraffin oil impedes APHID transmission of potato virus Y," *Canadian Journal of Microbiology*, 9(3): 369-380, 1963.

Brochure for Civitas, Petro-Canada, retrieved on Aug. 22, 2011. Retrieved from the Internet: <URL: http://www.civitasturf.com/pdf/CIVITAS-technical-brochure.pdf>, 12 pages.

Brown Patch on Turfgrass *Rhizoctonia* spp., Cornell University Department of Plant Pathology and Plant-Microbe Biology, created Aug. 1999, updated May 2011. Retrieved from the Internet: <URL: http://plantclinic.cornell.edu/factsheets/brownpatch.pdf>, 3 pages.

Brown Patch Rhizoctonia solani, University of Guelph, Nov. 27, 2003. Retrieved from the Internet: <URL: http://www.uoguelph.ca/pdc/Factsheets/PDFs/127TurfBrownPatch.pdf>, 1 page.

Brown Patch, Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/brown--patch>, 3 pages.

Buckley et al., "An Integrated Approach to Insect Management in Turfgrass: Black Cutworm," Rutgers, the State University of New Jersey, Mar. 2010. Retrieved from the Internet: <URL: http://snyderfarm.rutgers.edu/pdfs/BlackCutworms.pdf>, 3 pages.

Burpee and Latin, "Reassessment of Fungicide Synergism for Control of Dollar Spot," *Plant Disease*, 92(4):601-606, 2008.

Burpee et al., "Interactive Effects of Plant Growth Regulators and Fungicides on Epidemics of Dollar Spot in Creeping Bentgrass," *Plant Disease*, 80(11):1245-1250, 1996.

Burr and Warren, "Enhancement of Herbicide Activitiy with an Isoparaffinic Oil Carrier," *Weed Science*, 19(6):701-705, Nov. 1971.

Burt, "Tolerance of warmseason turf grasses to herbicides," Plantation Field Laboratory Mimeo Report PFL66-1, University of Florida Digital Collections [online] Aug. 1966. Retrieved from the Internet: <URL: http://ufdc.ufl.edu//UF00076427/00001>, 11 pages.

Buss, "Insect Pest Management on Golf Courses," University of Florida. Retrieved from the Internet: <URL: http://edis.ifas.ufl.edu/in410>, 14 pages. Retrieved on Aug. 26, 2011.

Buss, "Insect Pest Management on Turfgrass," University of Florida. Retrieved from the Internet: <URL: http://edis.ifas.ufl.edu/ig001>, 13 pages. Retrieved on Aug. 26, 2011.

Butler, "Cultural practices and their effects upon turf grass growth and stress tolerance," The British and International Golf Greenkeepers Association Limited, Jul. 2006. Retrieved from the Internet: <URL: http://www.bigga.org.uk/about-us/magazine/back-issues/07-2006/cultural-pray-tim-butler/00919.html>, 7 pages.

Bywater, "Plant Growth Regulators: Mode of Action," AGCSA [online] Australian Turfgrass Management vol. 3.3, Jun.-Jul. 2001. Retrieved from the Internet: <URL: http://www.agcsa.com.au/static/atm_articles/html/3_3c.html>, 3 pages.

Cawthon and Pyle, "Use of Plant Growth Regulators to Retard Growth of Bermudagrass and Dallisgrass in the Landscape," Texas A&M University, retrieved Aug. 24, 2011. Retrieved from the Internet: URL:<http://www.tamu-commerce.edu/agscience/res-dlc/turf/pgr.html>, 5 pages.

Chase and Simone, "Phytotoxicity on Foliage Ornamentals Caused by Bactericides and Fungicides," Plant Pathology Fact Sheet, Florida Cooperative Extension Service, Institute of Food and Agricultural Sciences, University of Florida. Retrieved from the Internet: <URL: http://plantpath.ifas.ufl.edultakextpublFactSheetsip-pOO30.pdf>, 8 pages. Retrieved on Aug. 26, 2011.

Chemical Structures, The Bugwood Network, Nov. 7, 2002. Retrieved from the Internet: <URL: http://www.bugwood.org/PAT/22chemicalstructures.html>, 8 pages.

Christians, "Creative uses for plant growth regulators," *USGA Green Sec. Rec*, 39: 11-13, Sep. 2001/Oct. 2001.

Clarke et al., "Pest Control Recommendations for Lawn and Turf Areas, 2006" Rutgers NJAES Cooperative Extension, Jul. 13, 2006. Retrieved from the Internet: <URL: http://njaes.rutgers.edu/pubs/publication.asp?pid=e037>, 33 pages.

Cleary Chemical Corporation, "Use of Cleary's Grass Greenzit™," 1 page, 2004.

(56) References Cited

OTHER PUBLICATIONS

Cline, "OLR mating disruption just got easier," Western Farm Press [online] Jun. 1, 2001. Retrieved from the Internet: <URL: http://westernfarmpress.com/olr-mating-disruption-just-got-easier>, 4 pages.

Cockerham et al., "Evaluation of Turfgrass Growth Retardant Chemicals," *California Turfgrass Culture*, 23-24, 21(3):23-24, 1971.

Colby, "Calculating synergistic and antagonistic responses of herbicide combinations," *Weeds*, 20-22, 1967.

Coo-Ranger et al., "Ionic silicone surfactants in water-in-silicone oil emulsions containing proteins," *Polymer Preprints*, 45(1):674-675, 2004.

Cortes-Barco et al., "Comparison of induced resistance activated by benzothiadiazole,(2R, 3R)-butanediol and an isoparaffin mixture against anthracnose of Nicotiana benthamiana," *Plant pathology*, 59(4):643-653, 2010.

Cortes-Barco et al., "Induced systemic resistance against three foliar diseases of Agrostis stolonifera by (2R, 3R)-butanediol or an isoparaffin mixture," *Annals of Applied Biology*, 157(2):179-189, 2010.

Corwin, "Integrated Pest Management: Identification & Management of Turfgrass Disease," University of Missouri Extension. Retrieved from the Internet: <URL: http://extension.missouri.edu/p/IPM1029> 56 pages, 2007.

Cranmer et al., "Controlled droplet application (CDA) of fluazifop and sethoxydim for annual and perennial weed control," 1983 Meeting of the Weed Science Society of America, 1983, 23-24, Weed Abstract vol. 033 Abs. (No. 00871).

Cranshaw, "Clover and Other Mites of Turfgrass," Colorado State University Extension. Dec. 2012. Retrieved from the Internet: <URL: http://www.ext.colostate.edu/pubs/insect/05505.html>, 2 pages.

Crocker & Simpson, "Pesticide screening test for the southern chinch bug," *Journal of Economic Entomology*, 74(6):730-731, 1981.

Croda, "Volpo," Croda Chemicals Europe Ltd, Jul. 2001. Retrieved from the Internet: <URL: http://www.chservice.ru/download/DC%20Volpo.pdf>, May 2004.

Cropper, "Towards Reducing Fungicide Use in the Control of Dollar Spot (*Sclerotinia homoeocarpa* F.T. Bennett) Disease on Creeping Bentgrass (*Agrostis stolonifera* L.)," May 4, 2009, Master of Science Thesis, University of Kentucky. Retrieved from the Internet: <URL: http://archive.uky.edu/handle/10225/1044>, 69 pages.

Danneberger and Street, "Turfgrass Growth Substances," *Golf Course Management*, Apr. 1990, 58(4):80, 82, 86, 88.

Datapak for SALVO herbicide, United Agri Products Canada Inc., 14 pages, Oct. 2005.

Dell et al., "The Efficacy of JMS Stylet-Oil on Grape Powdery Mildew and Botrytis Bunch Rot and Effects on Fermentation," *Am. J. Enol. Vitic.*, 49(1):11-16, 1998.

Dickey, "Using plant growth regulators in turfgrass management. (Green Science).," Golfscape [online] Sep. 1, 2002. Retrieved from the Internet: <URL: http://www.highbeam.com/doc/1G1-105617663.html/print>, 2 pages.

Diesburg, "Effects of Turf Colorants and FES04 on Spring Greenup of Zoysiagrass," 1990. Retrieved from the Internet: <URL: http://www.turf.uiuc.edu/research/summaries/1990/effect_colorant.pdf>, 2 pages.

Dokkuma, "Plant Growth Regulators as a Turfgrass Management Tool," Greenkeeper [online] 2008. Retrieved from the Internet: <URL: http://www.greenkeeper.com/upload/alinea_1425.pdf>, 4 pages.

Dokkuma, Plant Growth Regulators Used in Turfgrass Management, Greenkeeper [online] 2008. Retrieved from the Internet: <URL: http://www.greenkeeper.eu/upload/alinea_1420.pdf>, 4 pages.

Duell, "Turfgrass quality and phytotoxicity affected by growth retardants," Chapter 70. Retrieved from the Internet: <URL: http://archive.lib.msu.edu/tic/its/articles/1985pro749.pdf>, 8 pages. Retrieved on Aug. 24, 2011.

Engvild, "Herbicidal activity of 4-chloroindoleacetic acid and other auxins on pea, barley and mustard," *Physiologia Plantarum*, 96(2):333-337, Feb. 1996.

Erhan and Nelsen, "Comparisons of volatile organic chemical content of news, sheetfed, and heatset ink formulations," *Journal of the American Oil Chemists' Society*, 78(4):419-422, 2001.

Fasold, "Plant Growth Regulators: More Color, Less Clippings," Irrigation and Green Industry [online], May 15, 2009. Retrieved from the Internet: <URL: http://www.igin.com/article-925-%20plant_growth_regulat.html>, 4 pages.

Fertilome, "Broad Spectrum Landscape & Garden Fungicide (32 oz)," Fertilome.com [online] archived on Dec. 30, 2010. Retrieved from the Internet: <URL: http://web.archive.org/web/20101230174658/http://www.fertilome.com/product.aspx?pid=9950d7c1-dfed-4268-9474-eb508f967dc0>, 2 pages.

Fidanza et al., "Evaluation of fungicide and plant growth regulator tank-mix programmes on dollar spot severity of creeping bentgrass," *Crop Protection*, 25(9):1032-1038, 2006.

Fidanza et al., "Use of a Soil Surfactant with Fungicides for Control of Fairy Ring Disease in Turfgrass," *Journal of ASTM International*, 4(4):77-82, 2007.

Fishel, "Plant Growth Regulators," University of Florida, Feb. 2006, Revised Apr. 2009, 5 pages.

Fungicide Resistance Action Committee [FRAC] Code List: Fungicides sorted by mode of Action, Fungicide Resistance Action Committee, retrieved on Aug. 22, 2011. Retrieved from the Internet: <URL: http://www.frac.info/frac/publication/anhang/FRAC%20Code%20List%202011final.pdf>, 10 pages.

Furuta, "Strangers in a Strange Land," California Turfgrass Culture, 21(3):22-23, 1971.

Gaussoin and Branham, "Plant Growth Regulator Effects on Annual Bluegrass/Creeping Bentgrass Competition," Department of Crop & Soil Sciences Michigan State University, pp. 52-56, Jul. 2008. Retrieved from the Internet: <URL: http://archive.lib.msu.edu/tic/mitgc/article/198852a.pdf>.

Gauvrit and Cabanne, "Oils for weed control: Uses and mode of action," *Pesticide Science*, 37(2):147-153, 1993.

Gebhardt et al., "Herbicide application with the controlled droplet applicator when using soybean oil," American Society of Agricultural Engineers, Paper No. 83-1509, 13 pages, 1983.

Gilbert and Kopec, "Spring Greenup of Dormant Non-Overseeded Bermudagrass," University of Arizona College of Agriculture 2004 Turfgrass and Ornamental Research Report. Retrieved from the Internet: <URL: http://ag.arizona.edu/pubs/crops/az1359/az13593c11.pdf>, 4 pages.

Golden Artist Colors, "Pigment Identification Charts," Retrieved on Sep. 15, 2011. Retrieved from the Internet: <URL: http://www.goldenpaints.com/technicaldata/pigment.php>, 15 pages.

Goodwin and McBrydie, "Effect of surfactants on honey bee survival," *New Zealand Plant Protection*, 53:230-234, 2000.

Grey et al., "Timed Release of Flurprimidol from a Granular Formulation in Mulches and Sand," *HortScience*, 44(2):512-515, 2009.

Grover et al., "Droplet and Vapor Drift from Butyl Ester and Dimethylamine Salt of 2,4-D," *Weed Science*, 20(4): 320-324, Jul. 1972.

Guy et al., "The performance of postemergence grass herbicides applied with sprinkler irrigation," Proceedings of the 39th annual meeting of the Southern Weed Science Society, p. 106, 8A, 1986.

Harmon and Latin, "Gray leaf spot of perennial ryegrass," Plant Health Progress [online]. Retrieved from the Internet: <URL: http://www.plantmanagementnetwork.org/pub/php/diagnosticguide/2003/ryegrass/>, 8 pages, 2003.

Hartzler, "Role of spray adjuvants with postemergence herbicides," Iowa State University Weed Science [online], Mar. 7, 2001, Retrieved from the Internet: <URL: http://www.weeds.iastate.edu/mgmt/2001/additives.htm>, 3 pages.

(56) References Cited

OTHER PUBLICATIONS

Heil and Bostock, "Induced systemic resistance (ISR) against pathogens in the context of induced plant defences," *Annals of Botany*, 89(5), 503-512, 2002.

Hill, "Silicone surfactants—new developments," *Current opinion in colloid & interface science*, 7(5):255-261, 2002.

Hodgson, "Armyworms and cutworms in turfgrass," Utah State University Extension, Jun. 2007. Retrieved from the Internet: <URL: http://utahpests.usu.edu/IPM/files/uploads/PDFDocs/factsheet-pdf/armyw-cutw-turf07.pdf>, 3 pages.

Hoffman et al., "Application of Fungicides for Suppression of Fusarium Head Blight (Scab)," North Dakota State University, May 2000. Retrieved from the Internet: <URL: http://www.ag.ndsu.edu/pubs/ageng/machine/ae1148.pdf>, 4 pages.

Hoffman, "Analysis of Alcohol and Alkylphenol Polyethers via Packed Column Supercritical Fluid Chromatography," (Doctoral dissertation, Virginia Polytechnic Institute and State University), 2004.

Holly Frontier®, "Sunspray Oils," 2014 [retrieved on Jul. 27, 2015]. Retrieved from the Internet: <URL: http://www.hollyfrontierlsp.com/Products/Horticultural-Oils/Sunspray-Oils/85/>, 1 page.

Horn, "Increasing the Effectiveness of Turf Herbicides by Use of Oil," Florida State Horticultural Society, pp. 499-509, 1966.

Horn, "Tolerance of Several Southern Turfgrasses to Various Spray Oils," Florida State Horticultural Society, pp. 494-499, 1966.

Hsiang and Tian, "Chemical Trials for Dollar Spot Disease Control," Summer 2006, Guelph Turfgrass Institute, 2006 Annual Research Report, Retrieved from the Internet <URL: http://131.104.104.3/06anrep/40-42.pdf>, pp. 40-42.

Hsiang et al., "Baseline sensitivity and cross-resistance to demethylation-inhibiting fungicides in Ontario isolates of Sclerotinia homoeocarpa," *European journal of plant pathology*, 103(5):409-416, 1997.

Hsiang et al., "Sensitivity of Sclerotinia homoeocarpa to demethylation-inhibiting fungicides in Ontario, Canada, after a decade of use," *Plant pathology*, 56(3):500-507, 2007.

Huang, "Better Creeping Bentgrass Through Electricity," *GCM*, 2003, pp. 85-86. Retrieved from the Internet: <http://www2.gcsaa.org/gcm/2003/dec03/pdfs/12electricity.pdf>, 2 pages.

Huang, "Plant growth regulators: What and why," *Golf Course Management*, pp. 157-160, Jan. 2007.

Jordan, "Enhanced post-emergence herbicide efficacy with ultra-low volume application," Proceedings of the 48th annual meeting of the Southern Weed Science Society, 48, pp. 208-212, 1995.

Kaminski and Dernoeden, "Dead Spot Disease of Creeping Bentgrass," University of Maryland, Nov. 2003. Retrieved from the Internet: <URL: http://www.hgic.umd.edu/content/documents/TT-14DeadSpot.pdf>, 2 pages.

Kaminski and Dernoeden, "Dead Spot of Creeping Bentgrass and Hybrid Bermudagrass," Plant Management Network [online], Apr. 19, 2005. Retrieved from the Internet: <URL: http://www.plantmanagementnetwork.org/pub/ats/diagnostic/2005/deadspot/>, 8 pages.

Kaminski and Dernoeden, "Understanding Bentgrass Dead Spot," USGA Turfgrass and Environmental Research Online, 2(2):1-7, Jan. 15, 2003. Retrieved rom the Internet: <URL: http://turf.lib.msu.edu/tero/v02/n02.pdf>, 9 pages.

Kaminski, "Bentgrass dead spot," University of Connecticut, Dec. 2006. Retrieved from the Internet: <http://www.turf.uconn.edu/pclf/research/factsheets/Disease_Bentgrass_Dead_Spot.pdf>, 2 pages.

Kopec et al., "Repeat Applications of Paclobutrazole (TGR) Plant Growth Regulator on Overseeded Bermudagrass Turf: Weed Control and Bermudagrass Transition," Turfgrass, Landscape and Urban IPM Research Summary, The University of Arizona. Retrieved from the Internet: <URL: http://ag.arizona.edu/pubs/crops/az1487/14875e.pdf>, pp. 174-196, Feb. 2009.

Kopeck and Gilbert, "Overseed Greens Performance Trials," 6 pages, 1995-1996.

Koppenhofer et al., "An Integrated Approach to Insect Management in Turfgrass: Sod Webworms," Rutgers, The State University of New Jersey, Mar. 2010. Retrieved from the Internet: <URL: http://snyderfarm.rutgers.edu/pclfs/SodWebworms.pdf> 3 pages.

Koppenhofer et al., "An Integrated Approach to Insect Management in Turfgrass: White Grubs," Jun. 2002. Retrieved from the Internet: <URL: https://www.co.somerset.nj.us/pdf/JapBeetleFS.pdf>, 4 pages.

Kremer et al., "Control of Sclerotinia homoeocarpa in turfgrass using effective microorganisms," *EM World J*, 1:16-21, 2000.

Latin and Stewart, "Turfgrass Disease Profiles: Gray Leaf Spot," Purdue University. Retrieved from the Internet: <URL: https://www.extension.purdue.edu/extmedia/BP/BP-107-W.pdf> Apr. 2008, 2 pages.

Latin, "Turfgrass Disease Profiles: Brown Patch," Purdue University, Retrieved from the Internet: <URL: https://www.extension.purdue.edu/extmedia/BP/BP-106-W.pdf> Apr. 2008, 2 pages.

Latin, "Turfgrass Disease Profiles: Dollar Spot," Purdue University. Retrieved from the Internet: <URL: https://www.extension.purdue.edu/extmedia/BP/BP-105-W.pdf>, Jan. 2010, 3 pages.

Latin, "Turfgrass Disease Profiles: Gray Snow Mold," Purdue University, Retrieved from the Internet: <URL: https://www.extension.purdue.edu/extmedia/BP/BP-101-W.pdf> Jan. 2006, 3 pages.

Latin, "Turfgrass Disease Profiles: Leaf Spot/Melting Out," Purdue University, Retrieved from the Internet: <http://www.ces.purdue.edu/extmedia/bp/bp-103-w.pdf>, Apr. 2008, 2 pages.

Latin, "Turfgrass Disease Profiles: Pink Snow Mold and Microdochium Patch," Purdue University, Retrieved from the Internet: <URL: https://www.extension.purdue.edu/extmedia/BP/BP-102-W.pdf>, Jan. 2006, 3 pages.

Lickfeldt et al., "Implications of repeated trinexapac-ethyl applications on Kentucky bluegrass," *Agronomy Journal*, 93(5):1164-1168, 2001.

Lincoln County Noxious Weed Control, "Herbicide Facts," 2007, Retrieved from the Internet: <URL: http://www.co.lincoln.wa.us/WeedBoard/heibicide/herbicidefacts.pdf>, 22 pages.

Liu, "Cytokinin Effects on Creeping Bentgrass Responses to Heat Stress: I. Shoot and Root Growth," *Crop. Sci.*, 42:457-465, 2002.

Liu, "Painting dormant bermudagrass putting greens," *Golf Course Manage*, 75(11):86-91, 2007.

Lorbeer, "Synergism, Antagonism, and Additive Action of Fungicides in Mixtures," *Phytopathology*, 86(11):1261-1262, 1996.

Material Safety Data Sheet for AGRI-DEX, Helena Chemical Company, 1 page, Apr. 29, 2005.

Material Safety Data Sheet for Banner MAXX, Syngenta Crop Protection, Inc., 5 pages, Aug. 30, 2010.

Material Safety Data Sheet for Blendex VHC, Helena Chemical Company, 1 page, Jul. 27, 2000.

Material Safety Data Sheet for Broadcoat Spray Adjuvant, Caltex Australia Limited, 5 pages, Sep. 2003.

Material Safety Data Sheet for Chipco Signature, Bayer CropScience Pty Ltd, May 1, 2007, 6 pages.

Material Safety Data Sheet for Chipco Signature, Bayer CropScience Pty Ltd, Oct. 21, 2002, 7 pages.

Material Safety Data Sheet for Civitas, Petro-Canada Lubricants, Inc., 6 pages, Mar. 21, 2011.

Material Safety Data Sheet for Cleary 3336 Plus, Cleary Chemical Corporation, Feb. 1, 2005, 4 pages.

Material Safety Data Sheet for Daconil 2787, Syngenta Crop Protection Canada, Inc., 7 pages, Dec. 31, 2008.

Material Safety Data Sheet for Daconil Ultrex Fungicide, Syngenta Crop Protection Canada, Inc., 7 pages, Aug. 1, 2009.

Material Safety Data Sheet for FORE 80 WP Rainshield, Dow AgroSciences, Jun. 1, 2001, 9 pages.

Material Safety Data Sheet for FORE Fungicide, Rohm and Haas Company, 9 pages, Oct. 16, 1995.

Material Safety Data Sheet for Grass Greenzit, W.A.Cleary Chemical Corporation, 2 pages, Oct. 1997.

Material Safety Data Sheet for Green Lawnger, Becker Underwood, Inc., 5 pages, Feb. 25, 2009.

Material Safety Data Sheet for Harmonizer, Petro-Canada Lubricants Inc., 6 pages, May 6, 2011.

(56) References Cited

OTHER PUBLICATIONS

Material Safety Data Sheet for JMS Stylet-Oil, 4 pages, Mar. 1, 1994.
Material Safety Data Sheet for Kannar Green KC 200, 2007.
Material Safety Data Sheet for Kannar Turfkare Green, 1 page, Sep. 18, 2007.
Material Safety Data Sheet for Killex Lawn Weed Control Concentate (Ortho), Scotts Canada Ltd., 7 pages, Sep. 13, 2005.
Material Safety Data Sheet for Lambent MFF 159-100, Lambent Technologies Corp., 3 pages, Apr. 4, 2006.
Material Safety Data Sheet for Lambent MFF-199 SW, Lambent Technologies Corp., 3 pages, Jan. 31, 2005.
Material Safety Data Sheet for Peptoil, Drexel Chemical Company, 1 page, Jan. 7, 2005.
Material Safety Data Sheet for Regreen™ Turfgrass Colorant, Precision Laboratories, Inc., 3 pages, Mar. 1, 2010.
Material Safety Data Sheet for Rovral Green GT Flowable Fungicide, Bayer CropScience Inc., 9 pages, Mar. 2, 2011.
Material Safety Data Sheet for Silsurf A008-UP, Siltech Corporation, 4 pages, Aug. 21, 2009.
Material Safety Data Sheet for Sunspray 6E, Jun. 1, 2009, [retrieved on Sep. 30, 2014]. Retrieved from the Internet: <URL: http://www.recarroll.com/cw3/Assets/product files/Sunspray 6E.pdf>, 5 pages.
Material Safety Data Sheet for Surf AC 820, Drexel Chemical Company, 1 page, Jul. 22, 2005.
Material Safety Data Sheet for Sylgard 309 Silicone Surfactant, Dow Corning Corporation, 9 pages, Apr. 5, 2001.
McCarty and Whitwell, "Plant Growth Regulators for Fine Turf," Clemson University, South Carolina, archived Sep. 15, 2009. Retrieved from the Internet: <URL: http://www.clemson.edu/extension/horticulture/turf/pest_guidelines/growth_regulators.html>, 1 page.
McCowan, "Turf Herbicide Rx: Add Oil," Agricultural Chemicals, 23(4):18-21, 1968.
McCullough et al., "Ethephon and Trinexapac-ethyl Influence Creeping Bentgrass Growth, Quality, and Putting Green Performance," Plant Management Network, 2006. Retrieved from the Internet: <URL: http://www.plantmanagementnetwork.org/publats/research/2006/creeping/>, 7 pages.
McCullough et al., "Plant Growth Regulator Regimens Reduce Poa annua Populations in Creeping Bentgrass," *Plant Management Network*, 6 pages, Mar. 4, 2005.
McCullough, "Turfgrass Growth Regulators for Professional Managers," Extension Agronomist—Weed Science, Georgia Turf, retrieved Aug. 25, 2011. Retrieved from the Internet: <URL: http://commodities.caes.uga edukurfgrass/georgiaturf/publicat/PCRP2011 /PGR.pdf>, 2 pages.
Meister, Jr., Farm Chemicals, 141(1), pp. 4, 38, 42, 44, 46, 48, 77, 78, 80, 82, 84, 86, 92, 94, 96, Jan. 1978.
Mercier, "Use of the growth regulator paclobutrazol in the management of dollar spot of creeping bentgrass in Minnesota," *Phytoprotection*, 80(2):65-70, 1999.
Mergos et al., "Dielectric properties of nanopowder emulsions in paraffin oil," 2011 IEEE International Conference on Dielectric Liquids, Sep. 8, 2011.
Morris, "A Guide to NTEP Turfgrass Ratings," NTEP.org [online], 2011. Retrieved from the Internet: <URL: http://www.ntep.org/reports/ratings.htm>, 5 pages.
Mueller, "Fungicides: Qol Fungicides" Iowa State University, Available from: <URL: http://www.ipm.iastate.edu/ipm/icm/2006/5-22/fungicides.html>, 2 pages.
Mueller, "Fungicides: Triazoles," Intigrated Crop Management, Iowa State University, May 30, 2006. Retrieved from the Internet: <URL: http://www.ipm.iastate.edu/ipm/icm/2006/5-30/fungicides.htm >, 3 pages.
Murphy et al., "Plant Growth Regulators Used in Turfgrass Management," Georgia Turf, Retrieved on Aug. 25, 2011. Retrieved from the Internet: <http://commodities.caes.uga.edu/turfgrass/georgiaturf/WeedMngt/weedcontrol/PGR.htm>, 10 pages.

Murphy, "Turfgrass Growth Regulators for Professional Managers," Extension Agronomist—Weed Science, Georgia Turf, retrieved Aug. 25, 2011. Retrieved from the Internet: <URL: http://commodities.caes.uga.edu/turfgrass/georgiaturf/Publicat/PCRP2009/PGR.09.pdf>, 1 page.
Nalewaja et al., "Crop origin oils with grass control herbicides." *Proc. North Cent. Weed Control Conf.*, vol. 38, p. 3, 1983 (Abstract).
Nelson and Shearer, "2, 4-D and Mycoleptodiscus terrestris for control of Eurasian watermilfoil," *Journal of Aquatic Plant Management*, 43: 29-34, 2005.
Notice for Mecoprop-P TGAC, Commonwealth of Australia Gazette No. NRA 3, 2 pages, Mar. 6, 2001.
Oregon State University, National Forage & Grasslands Cirriculumn, "Discuss the basics of grass growth," forages.oregonstate.edu [online] <URL: http://forages.oregonstate.edu/nfgc/eo/onlineforagecurriculum/instructormaterials/availabletopics/management/growth> copyright 2008, 6 pages.
Ostmeyer, "The Color Green," *Golf Course Management*, pp. 40, 44, Aug. 1994.
Palla et al., "Correlation of dispersion stability with surfactant concentration and abrasive particle size for chemical mechanical polishing (cmp) slurries," *Journal of dispersion science and technology*, 21(5):491-509, 2000.
Pamphlet for Daconil 2787 Flowable Fungicide, Syngenta Crop Protection Canada, Inc., 9 pages, May 2004.
Pamphlet for Daconil Ultrex Fungicide, Syngenta Crop Protection Canada, Inc., 9 pages, May 2004.
Patton and Latin, "Turfgrass Disease Profiles: Rhizoctonia Large Patch," Purdue University, Retrieved from the Internet: <URL: https://www.extension.purdue.edu/extmedia/BP/BP-117-W.pdf> Feb. 2005, 3 pages.
Pavlista, "Paraffin enhances yield and quality of the potato cultivar Atlantic," *J. Prod. Agric.*, 8(1):40-42, 1995.
Perry, "Ground Covers: Specifications and Costs," *California Turfgrass Culture*, 21(3):21-22, 1971.
Perry, "Silicone Surface-Active Agents," Dow Corning Corporation, 2005. Retrieved from the Internet: <URL: http://www.dowcorning.com/content/publishedlit/26/1365.pdf>, 12 pages.
Pest Control for Professional Turfgrass Managers 2011, North Carolina State University, retrieved on Sep. 15, 2011. Retrieved from the Internet: <URL: http://www.turffiles.ncsu.edu/PDFFiles/004176/AG408PestControl_Prof- essionals.pdf>, 58 pages.
Pesticide Product Label System (PPLS), Search Results for PureSpray Oil 10E, Approval dates Apr. 21, 2000, Jul. 23, 2002, Sep. 24, 2003, Mar. 5, 2004. EPA Office of Pesticide Programs. Retrieved from the Internet: <http://oaspub.epa.gov/pestlabl/ppls.srchreslt?CompNum=69526&ProdNum=5>, 26 pages.
Platte Chemical Co., "Product Information Bulletin: Salvo: A premium broadleaf herbicide for use in corn, small grains, grass pastures, reangeland and other crop and noncrop areas," 6 pages, 2001.
Product Bulletin for Caltex, Caltex Australia, retrieved Aug. 2, 2006. Retrieved from the Internet: <URL: http://www.caltex.com.au/products_oil_detail_print.asp?id=229>, 2 pages.
Product Information Sheet for Sylgard 309 Silicone Surfactant, Dow Corning Corporation, 4 pages, May 2004.
Propiconazole Pesticide Information Profile, Extension Toxicology Network, Oct. 1997. Retrieved from the Internet: <URL: http://pmep.cce.cornell.edu/profiles/extoxnet/metiram-propoxur/propiconazole-ext.html>, 6 pages.
PureSpray Spray Oil 10E, Delaware Department of Agriculture Pesticide Database Searches, 2 pages, retrieved Apr. 7, 2005.
Puterka, "Fungal pathogens for arthropod pest control in orchard systems: mycoinsecticidal approach for pear psylla control," *BioControl*, 44(2):183-209, 1999.
Quantification of Phosphorus in Water Based Green Pigments, 1 page, 2009.
Quicksheet for SALVO Herbicide, UAP Canada, 4 pages, 2006.
Rieke, "Thatchremoval," *California Turfgrass Culture*, 21(3):19-20, 1971.

(56) References Cited

OTHER PUBLICATIONS

Ross et al., "The Effect of the Plant Growth Regulator Primo on Winter Hardiness Levels," Prairie Turfgrass Research Centre, retrieved on Aug. 25, 2011. Retrieved from the Internet: <URL: http://www.oldscollege.ca/ptrc/2004_ar/Primohardiness02-05.htm>, 4 pages.
Samoucha et al., "Synergism in fungicide mixtures against Pseudoperonospora cubensis," *Phytoparasitica*, 16(4):337-342, 1988.
Schott et al., "Effects of adjuvants on herbicidal action. III. Effects of petroleum and rapeseed oils on diclofop-methyl action on ryegrass," *Agronomie*, 11(1):27-34, 1991.
Schutte et al., "Application of Azoxystrobin for Control of Benomyl-Resistant Guignardia citricarpa on 'Valencia' Oranges in South Africa," *Plant Dis.*, 87(7): 784-788, Jul. 2003.
Scotts Canada Home: Killex Concentrate, Retrieved Aug. 2, 2006. Retrieved from the Internet: <URL: http://scottscanada.calindex.cfmleventlProductGuide.product/ documentId/30B255B82B>, 2 pages.
Shaposhnikov et al., "Carboxy-substituted phthalocyanine metal complexes," *Russian journal of general chemistry*, 75(9): 1480-1488, 2005.
Shearman et al., "Colorant effects on dormant buffalograss turf performance," *HortTechnology*, 15(2), 244-246, 2005.
Short and Castner, "Turfgrass Insects Sheet 1," University of Florida, Nov. 1992, reviewed Jun. 2005. Retrieved from the Internet: <URL: http://edis.ifas.ufl.edu/in025>, 2 pages.
Short and Castner, "Turfgrass Insects Sheet 2," University of Florida, Nov. 1992, reviewed May 2003. Retrieved from the Internet: <URL: http://edis.ifas.ufl.edu/in026>, 2 pages.
Smitley and Davis, "Black Cutworms," Michigan State University Turfgrass Science, archived on Feb. 12, 2010. Retrieved from the Internet: <URL: http://www.turf.msu.edu/black-cutworms>, 2 pages.
Soomary et al., "Evaluation of Fungicides for Control of the Leaf Spot Disease Caused by Mycosphaerella eumusae on Banana in Mauritius," Food and Agricultural Research Council, Proceedings Fourth Annual Meeting of Agricultural Scientists, pp. 61-65, Feb. 2001.
Specimen Label for AGRI-DEX, Helena Chemical Company, 2 pages, 2005.
Specimen Label for Banner MAXX, Syngenta Crop Protection, Inc., 31 pages, May 2004.
Specimen Label for Blendex VHC, Helena Chemical Company, 2 pages, May 2006.
Specimen Label for Chipco Signature, Bayer CropScience Pty Ltd, 2 pages, May 2004.
Specimen Label for Civitas, Petro-Canada Lubricants, Inc., 9 pages, May 2004.
Specimen Label for Cleary 3336 Plus, Cleary Chemical Corporation, 4 pages, May 2004.
Specimen Label for Fore 80WP Rainshield, Dow AgroSciences, 7 pages. Revised Jan. 8, 2007.
Specimen Label for Grass Greenzit: Permanent Green Pigment for Grass, 2 pages, 1998.
Specimen Label for Harmonizer, Petro-Canada Lubricants, Inc., 1 page, May 2004.
Specimen Label for Killex, Scotts, Canada Ltd., 6 pages, Jul. 23, 2001.
Specimen Label for Peptoil, Drexel Chemical Company, 2 pages, May 2004.
Specimen Label for Regreen, Precision Laboratories, Inc. 2 pages, Dec. 10, 2007.
Specimen Label for Rovral Green GT, Bayer CropScienc Inc., 2 pages, Mar. 19, 2009.
Specimen Label for Sil-Fact, Drexel Chemical Company, 1 page, May 2004.
Specimen Label for Sil-MES 100, Drexel Chemical Company, 1 pages, May 2004.
Specimen Label for Surf-Ac 820, Drexel Chemical Company, 1 page, May 2004.
Specimen Label for Trimec Classic, PBI/Gordon Corporation, 2 pages, 1973.
Specimen Label for Trimec Southern, PBt/Gordon Corporation, 2 pages, 1987.
Technical Data Sheet for Lambent MFF 159-100, Lambent Technologies Corp., 1 page, May 2004.
Technical Data Sheet for Lambent MFF-199 SW, Lambent Technologies Corp., 1 page, May 2004.
Technical Data Sheet for Silsurf A008-UP, Siltech Corporation, 1 page, May 2004.
Technical Information for Lutensol AT types, BASF SE, 10 pages, May 2004.
Technical Sheet for Green Lawnger, Becker Underwood, Inc. 1 page, Nov. 2010.
The Seed Site, "Monocots and Dicots," captured Feb. 24, 2010. Retrieved from the Internet: <URL: http://web.archive.org/web/20100224074428/http://theseedsite.co.uk/monocot.html >, 2 pages.
Trathnigg et al., "Molecular characterization of ethoxylates by complementary chromatographic techniques. Evaluation of efficiency and reliability," *Tenside Surf. Det.*, 40(3), 148-154, 2003.
Tu et al., "Weed control methods handbook: tools and techniques for use in natural areas," *The Nature Conservancy*, Wildland Invasive Species TEAM, version Apr. 2001, 219 pages.
Turfgrass Pest Control, West Virginia University, retrieved on Aug. 22, 2011. Retrieved from the Internet: <URL: http://www.wvu.edu/.about.exten/infores/pubs/pest/pcerti19.pdf>, 12 pages.
University of Arkansas, "Turf Tip—MSMA, Fungicide synergism, Buffalograss, Pythium." Retrieved from the Internet: <URL: http://turf.uark.edu/turfhelp/archives/030509.html> Mar. 5, 2009, 3 pages.
Unruh and Brecke, "Plant Growth Retardants for Fine Turf and Roadsides/Utilities," University of Florida, Apr. 1999, reviewed Sep. 2006, retrieved on Aug. 24, 2011. Retrieved from the Internet: <URL: http://edis.ifas.ufl.edu/pdffiles/WG/WG06400.pdf>, 5 pages.
Vallad and Goodman et al., "Systemic Acquired Resistance and Induced Systemic Resistance in Conventional Agriculture," *Crop Science*, 44(6):1920-1934, 2004.
Van Dam and Kurtz, "A Turfgrass Colorant Study," California Turfgrass Culture, 21(3):17-19, Summer 1971.
van Haeringen et al., "The Development of Solid Spectral Filters for the Regulation of Plant Growth," *Photochemistry and Photobiology*, 67(4):407-413, Apr. 1998.
VanBibber, "Putting the Numbers to PGRs," Grounds MAIN1ENANCE, 2008. Retrieved from the Internet: <URL: http://grounds-mag.com/chemicals/grounds_maintenance_putting_numbers_pgrs/>, 6 pages.
Vann et al., "Rhizoctonia Large Patch Disease of Zoysiagrass and Bermudagrass," University of Arkansas Division of Agriculture, <https://www.uaex.edu/publications/PDF/FSA-7527.pdf> Mar. 1, 2007, 2 pages.
Vincelli, "Chemical Control of Turfgrass Diseases 2011," University of Kentucky College of Agriculture, <URL: http://pest.ca.uky.edu/PSEP/Manuals/ppal.pdf>, 24 pages.
Vol'pin et al., "Redox and fungicidal properties of phthalocyanine metal complexes as related to active oxygen," *Journal of Inorganic Biochemistry*, 81(4): 285-292, 2000.
Walsh et al., "Biology and management of dollar spot (*Sclerotinia homoeocarpa*); an important disease of turfgrass," *HortScience*, 34(1): 13-21, 1999.
Wicks, "Control of grapevine powdery mildew with mineral oil: an assessment of oil concentration and spray volume," *Australian Journal of Grape and Wine Research*, 5: 61-65, 1999.
Wikipedia, "2,4-Dichlorophenoxyacetic acid," retrieved on Aug. 29, 2006. Retrieved from the Internet: <URL: http://en.wikipedia.orglwikii2%2C4-D>, 3 pages.
Womack et al., "A vegetable oil-based invert emulsion for mycoherbicide delivery," *Biological Control*, 6(1), 23-28, 1996.
Yang et al., "Infection of leafy spurge by Alternaria alternata and A. angustiovoidea in the absence of dew," *Phytopathology*, 83(9): 953-958, 1993.

(56) References Cited

OTHER PUBLICATIONS

Youngner et al., "Colorants for Dormant Bermuda and Other Subtropical Grasses," *Southern California Turfgrass Culture*, 8(1):7-8, 1958.
Youngner, "Gibberellic acid on Zoysia grasses," *Southern California Turfgrass Culture*, 8:5-6, 1958.
Youngner, "Kikuyugrass, Pennisetum Clandestinum, and Its Control," *Southern California Turfgrass Culture*, 8(1):1-4, Jan. 1958.
Zhengdong, "Application of SK EnSpray Oil," Pesticide Science and Administration, 28(10):25-29, Dec. 31, 2007.
Chen et al., "Rheological properties of silica particle suspensions in mineral oil," *J Dispers Sci Technol.*, 26(6):791-798, 2005.
Heath et al., "Chelating agents and auxin," *Nature*, 201(4919):585-587, Feb. 8, 1964.
Product Information—Sunoco Sunspray 11N/11E, 1 page, 2009.
Wang, "Pesticide Pharmaceutics," *China Agriculture Press*, pp. 142-143, Aug. 2009, [English translation], 5 pages.
Bereskin & Parr, "Filing of Prior Art under S. 34.1(1)," [filed at the Canadian Intellectual Property Office for App. No. 2,877,585 corresponding to U.S. Appl. No. 13/821,808], 5 pages, Apr. 9, 2015.
Office Action for CA Application No. CA2,507,482 dated Aug. 11, 2009.
Office Action for CA Application No. CA2,507,482 dated Jan. 18, 2011.
Office Action for CA Application No. CA2,507,482 dated Nov. 9, 2011.
Office Action in corresponding Application No. 201180053975.5, dated Apr. 24, 2014, pp. 1-2.
European Search Report for Application No. 11822956.6 dated Feb. 3, 2014, 7 pages.
Examination Report for NZ Application No. NZ590318 dated May 6, 2011.
Office Action dated Nov. 10, 2011 from U.S. Appl. No. 12/563,929, 35 pages.
Office Action (Restriction Requirement) for U.S. Appl. No. 10/908,538 dated Feb. 26, 2009.
Office Action (Restriction Requirement) for U.S. Appl. No. 11/866,157 dated May 16, 2011.
Office Action (Restriction Requirement) for U.S. Appl. No. 12/492,863 dated Aug. 15, 2011.
Office Action for U.S. Appl. No. 10/908,538 dated Apr. 1, 2009.
Office Action for U.S. Appl. No. 11/866,157 dated Aug. 29, 2011.
International Preliminary Report on Patentability for PCT/CA2011/001018 issued Mar. 12, 2013, 6 pages.
International Search Report and Written Opinion for PCT/CA2011/001018 mailed Nov. 29, 2011, 8 pages.
Arysta Life Science, "Banvel Herbicide," retrieved on Nov. 23, 2016, http://www.cdms.net/LDat/Id279008.pdf, 29 pages.
Bell et al., "Comparison of Turfgrass Visual Quality Ratings with Ratings Determined Using a Handheld Optical Sensor," Hortitechnology., 19(2):309-316, 2009.
Beresford, "DMI (demethylation inhibitor) management strategy," Prevention and management strategies., pp. 21-25, 2003.
Bremer et al., "Relationships between Normalized Difference Vegetation Index and Visual Quality in Cool-Season Turfgrass: I. Variation among Species and Cultivars," Crop Science., 51:2212-2218, 2011.
Bunderson et al., "Tools for Evaluating Native Grasses as Low Maintenance Turf," Hortitechnology., 19(3):626-632, 2009.
CAS No. 117428-22-5, picoxystrobin, methyl (2E)-3-methoxy-2-{2-[6-(trifluoromethyl)-2-pyridyloxymethyl]phenyl}acrylate; methyl (2E)-3-methoxy-2-[2-({[6-(trifluoromethyl)pyridin-2-yl]oxy}methyl)phenyl]prop-2-enoate; (E)-Methyl 3-methoxy-2-(2-(((6-(trifluoromethyl)pyridin 2-yl)oxy)methyl)phenyl)acrylate; ACANTO; methyl (αE)-α-(methoxymethylene)-2-[[[6-(trifluoromethyl)-2-pyridinyl]oxy]methyl]benzeneacetate; Picoxystrobin; ZA1963; © 2013-2016, retrieved Nov. 28, 2016, http://www.molbase.com/en/precursor_117428-22-5-moldata-29033.html?synonyms=1, 1 page.

CAS No. 131807-57-3, (RS)-3-anilino-5-methyl-5-(4-phenoxyphenyl)-1,3-oxazolidine-2,4-dione; Famoxate; DPX-JE 874; 3-anilino-5-methyl-5-(4-phenoxyphenyl)-1,3 oxazolidine-2,4-dione; Famoxadone; 3-Anilino-5-methyl-5-(4 phenoxyphenyl)oxazolidine-2,4-dione; 5-methyl-5-(4-phenoxyphenyl)-3-(phenylamino)-2,4-oxazolidinedione; rac-(5R)-3-anilino-5-methyl-5-(4-phenoxyphenyl)-1,3-oxazolidine-2,4-dione; © 2013-2016, retrieved on Nov. 17, 2016, http://www.molbase.com/en/precursor_131807-57-3-moldata-3366.html?synonyms=1, 1 page.
CAS No. 133408-50-1, (E)-Metominostrobin; (2E)-2-(methoxyimino)-N-methyl-2-(2-phenoxyphenyl)acetamide; Metominofen; (E)-2-(methoxyimino)-N-methyl-2-(2-phenoxyphenyl)acetamide; Metominostrobin; ssf-126; (αE)-α-(methoxyimino)-N-methyl-2 phenoxybenzeneacetamide; metaminostrobin; © 2013-2016, retrieved on Nov. 28, 2016, http://www.molbase.com/en/precursor_133408-50-1-moldata-473468.html?synonyms=1, 1 page.
CAS No. 143390-89-0, methyl (αE)-α-(methoxyimino)-2-[(2-methylphenoxy)methyl]benzeneacetate; methyl (2E)-2-methoxyimino-2-[2-[(2-methylphenoxy)methyl]phenyl]acetate; Kresoxim-methyl; methyl (E)-methoxyimino[α-(o-tolyloxy)-o-tolyl]acetate; methyl (2E)-(methoxyimino){[(2-methylphenoxy)methyl]phenyl}acetate; © 2013-2016 , retrieved on Nov. 28, 2016, http://www.molbase.com/en/precursor_143390-89-0-moldata-28515.html?synonyms=1, 1 page.
CAS No. 161326-34-7, (S)-1-Anilino-4-methyl-2-methylthio-4-phenyl-2-imidazolin-5-one; (5S)-3-anilino-5-methyl-2-methylsulfanyl-5-phenylimidazol-4-one; Fenamidone; (5S)-3-anilino-5-methyl-2-(methylsulfanyl)-5-phenyl-3,5-dihydro-4H-imidazol-4-one; (5S)-3,5-dihydro-5-methyl-2-(methylthio)-5-phenyl-3-(phenylamino)-4H-imidazol-4-one; (S)-1-anilino-4-methyl-2-methylthio-4-phenylimidazolin-5-one; © 2013-2016, retrieved on Nov. 17, 2016, http://www.molbase.com/en/precursor_161326-34-7-moldata-475051.html?synonyms=1, 1 page.
CAS No. 248593-16-0, (2E)-2-[2-[[(E)-[(3E,4E)-3,4-bis(methovimino)pentan-2-ylidene]amino]oxymethyl]phenyl]-2-methoxyimino-N-methylacetamide; (2E)-2-(methoxyimino)-2-{2-[(3E,5E,6E)-5-(methovimino)-4,6-dimethyl-2,8-dioxa-3,7-diazanona-3,6-dien-1 yl]phenyl}-N-methylacetamide; Olysastrobin [ISO]; (αE)-α-(methoxyimino)-2-[(3E,5E,6E)-5-(methoxyimino)-4,6-dimethyl-2,8-dioxa-3,7-diaza-3,6-nonadienyl]-N-methylbenzeneacetamide; Orysastrobin; © 2013-2016, retrieved on Nov. 28, 2016, http://www.molbase.com/en/precursor_248593-16-0-moldata-1557223.html?synonyms=1, 1 page.
CAS No. 799247-52-2, pyribencarb; methyl {2-chloro-5-[(1E)-1-(6-methyl-2-pyridylmethoxyimino)ethyl]benzyl}carbamate; methyl [(2-chloro-5-{(1E)-N-[(6-methylpyridin-2-yl)methoxy]ethanimidoyl}phenyl)methyl]carbamate; methyl N-[[2-chloro-5-[(1E)-1-[[(6 methyl-2-pyridinyl)methoxy]imino]ethyl]phenyl]methyl]carbamate; methyl N-[[2-chloro-5-[(Z)-C-methyl-N-[(6-methylpyridin-2-yl)methoxy]carbonimidoyl]phenyl]methyl]carbamate; © 2013-2016, retrieved on Nov. 28, 2016, http://www.molbase.com/en/precursor_799247-52-2-moldata-1607308.html?synonyms=1, 1 page.
CAS No. 850881-70-8, "Coumoxystobin; Coumoxystrobine; methyl (2E)-2-(2-{[(3-butyl-4-methyl-2-oxo-2H-1-benzopyran-7-yl)oxy]methyl}phenyl)-3-methoxyprop-2-enoate; SYP 3375," © 2013-2016, retrieved on Nov. 17, 2016, http://www.molbase.com/en/850881-70-8-moldata-2475984.html, 1 page.
CAS No. 862588-11-2, Pyraoxystrobin; Benzeneacetic acid, 2-[[[3-(4-chlorophenyl)-1-methyl-1H-pyrazol-5-yl]oxy]methyl]-α-(methoxymethylene)-, methyl ester, (aE)—(CA Index Name), *STN*, entered STN on Sep. 7, 2005, retrieved on Nov. 28, 2016, stnc.cas.org, 3 pages.
Fässler et al., "Effects of indole-3-acetic acid (IAA) on sunflower growth and heavy metal uptake in combination with ethylene diamine disuccinic acid (EDDS)," J Chemosphere, 80(8):901-907, Aug. 1, 2010.
Gordon's brand, Amine 400 2,4-D Weed Killer, herbicide label, 4 pages, Oct. 2015.

(56) References Cited

OTHER PUBLICATIONS

Hwang et al., "The response of seeds and seedlings to treatment with indolylacetic acid," Annals of Botany, 4(13):31-37, Jan. 1, 1940.
Lopez et al., "Effect of indole-3-acetic acid, kinetin, and ethylenediaminetetraacetic acid on plant growth and uptake and translocation of lead, micronutrients, and macronutrients in alfalfa plants," Int J Phytoremediation., 11(2):131-149, Feb. 13, 2009.
Mitchell, "Effect of indoleacetic acid on the growth of some crop plants," Proceedings of the American Society for Horticultural Science, vol. 36, pp. 171-176, Arp. 1939.
Sarkissian IV et al., "Regulation of mitochondrial activity by indoleacetic acid," Biochim Biophys Acta., 128(3):413-418, Dec. 14, 1966.
STN Database accession No. 1939:39478, 1 page, Dec. 16, 2001.
Templeman, "The effect of some plant growth-substances on dry-matter production in plants," Empire J Exp Agric., 7(1):76-88, Jan. 1, 1939.

SYNERGISTIC PARAFFINIC OIL AND BOSCALID FUNGICIDES

CROSS REFERENCE TO RELATED APPLICATIONS

This application is a continuation of U.S. application Ser. No. 13/821,808 filed May 31, 2013, which is a U.S. National Phase application of International Patent Application No. PCT/CA2011/001018 filed Sep. 9, 2011, which claims the benefit of U.S. Provisional Patent Application Ser. No. 61/381,179 filed Sep. 9, 2010, all of which are incorporated herein by reference in their entirety.

FIELD

The invention relates to fungicidal compositions comprising a paraffinic oil and a heterocyclic aromatic $C_{18}H_{12}Cl_2N_2O$ compound, and methods for using such compositions on plants, including methods of formulating oil-in-water (O/W) emulsions containing the fungicidal compositions.

BACKGROUND

Grasses are often planted and maintained to provide aesthetically pleasing or recreationally useful groundcover for an area of land, which may be called a lawn, turf, pitch, field or green depending on the context. It is common to refer to the species of grasses that are maintained in this way as turfgrasses. Turfgrass care and maintenance has a rich horticultural tradition, reflecting in part the rich variety of pathologies that affect turfgrasses (see, for example, Walsh, B. et al., *HortScience*, 34, 1999, 13-21).

Dollar spot, thought to be caused by the fungal pathogen *Sclerotinia homoeocarpa*, is a common disease affecting turfgrass species, with symptoms that vary according to species and management practices. Characteristic symptoms of dollar spot infection include bleached, circular patches, with patches sometimes occurring in clusters, particularly on grasses cut short, such as golf course fairways, tees, and greens.

A number of management practices are known for controlling dollar spot disease in turfgrasses, including managing leaf wetness, or preventing moisture or nitrogen stress. Fungicides are also available for controlling dollar spot. For example, the use of the fungicide boscalid for controlling dollar spot disease in turfgrasses has been reported, with boscalid sometimes described as the first fungicide from the carboxamide active ingredient class (one of a class of compounds described in European Patent No. 545099). Boscalid is thought to be a systemic fungicide, acting as an inhibitor of respiration within the fungal cell (CAS No. 188425-85-6; Synonyms: 2-chloro-N-(4'-chloro[1,1'-biphenyl]-2-yl)-nicotinamide; 2-chloro-N-(4'-chloro[1,1'-biphenyl]-2-yl)-3-pyridinecarboxamide; 2-chloro-N-(4'-chloro-2-biphenylyl)nicotinamide; 2-chloro-N-(4'-chlorobiphenyl-2-yl)-nicotinamide; 2-chloro-N-[2-(4-chlorophenyl)phenyl]-pyridine-3-carboxamide; Nicobifen; 2-chloro-N-(4μ-chloro-2-biphenylyl)nicotinamide; Molecular Formula: $C_{18}H_{12}Cl_2N_2O$), having the following structure:

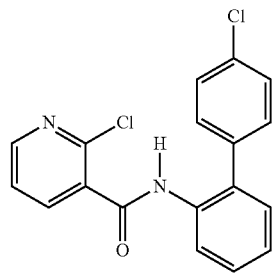 [SMILES: O=C(Nc1ccccc1-c1ccc(Cl)cc1)c1cccnc1Cl]

Boscalid has been made available in a number of commercial formulations, for example from the BASF Corporation under the names Endura™ or Pristine™ or Emerald™.

In an alternative approach to conventional chemical fungicides, oil-in-water emulsions comprising paraffinic oils and paraffinic spray oils have been used for controlling turfgrass pests (see, for example, Canadian Patent Application 2,472,806 and Canadian Patent Application 2,507,482). In addition, oil-in-water formulations comprising paraffinic oils and a pigment for controlling turfgrass pests have been reported (see, for example, WO 2009/155693). For example, Petro-Canada produces CIVITAS™, a broad spectrum fungicide and insecticide for use on golf course turf and landscape ornamentals, used for example to control powdery mildew, adelgids and webworms on landscape ornamentals (US EPA REG. NO. 69526-13). Product labeling indicates that CIVITAS™ may be applied as part of an alternating spray program or in tank mixes with other turf and ornamental protection products; and that CIVITAS™ may be used as a preventative treatment with curative properties for the control of many important diseases on turf, including fairways and roughs.

The combined use of formulations comprising paraffinic oils, pigment and other conventional chemical fungicides has also been reported for treating turfgrass pests, including fungicides such as demethylation inhibitors (e.g., propiconazole), methyl benzimidazole carbamate (e.g., thiophanate-methyl), and dicarboxamides (e.g., iprodione), see, for example, WO 2009/155693.

SUMMARY

In various embodiments, there is provided a fungicidal composition comprising an emulsifier, a paraffinic oil, and 2-chloro-N-(4'-chloro[1,1'-biphenyl]-2-yl)-3-pyridinecarboxamide (boscalid). In selected embodiments, the paraffinic oil and boscalid may be present in amounts that are synergistically effective when applied to a plant for controlling a fungal pathogen of the plant. In a further embodiment, there is provided a use of the composition for controlling a fungal pathogen on a plant. In another embodiment, there is provided a method of controlling a fungal pathogen of a plant, the method comprising applying to the plant a composition comprising an emulsifier and a paraffinic oil, in combination with boscalid. In selected embodiments, the paraffinic oil and boscalid may be applied in amounts that are synergistically effective for controlling the fungal pathogen. In selected embodiments, the method may further comprise mixing the paraffinic oil, the emulsifier, and boscalid before applying the composition to the plant. Compositions of the invention may be formulated as oil-in-water emulsions for application.

In selected embodiments, the paraffinic oil may comprise a paraffin having a number of carbon atoms ranging from about 12 to about 50. In alternative embodiments, the paraffinic oil may comprise a paraffin having a number of carbon atoms ranging from about 16 to about 35. In selected embodiments, the paraffinic oil may comprise a paraffin having an average number of carbon atoms of about 23. In alternative embodiments, the paraffinic oil may have a paraffin content of at least about 80%. In selected embodiments, the paraffinic oil may have a paraffin content of at least about 90%. In alternative embodiments, the paraffinic oil may have a paraffin content of at least about 99%.

In another embodiment, the composition may further comprise a pigment and a silicone surfactant. In selected embodiments, the pigment may be a polychlorinated (Cu II) phthalocyanine. In alternative embodiments, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In selected embodiments, the emulsifier may comprise a natural or synthetic alcohol ethoxylate, a polymeric surfactant, a sorbitan fatty acid ester, or a combination thereof, and the composition may further comprise a polyethylene glycol according to formula IV:

$$R^1-O-(CH_2CH_2O)_f-R^2$$

wherein $R^1$=H or $CH_2$=CH—$CH_2$ or $COCH_3$; $R^2$=H or $CH_2$=CH—$CH_2$ or $COCH_3$; and f≥1.

In selected embodiments, the fungal pathogen may be at least one of a fungus that causes dollar spot in turfgrass and a fungus that causes bentgrass dead spot or bermudagrass dead spot in a turfgrass. In alternative embodiments, the fungal pathogen may be a fungus that blights leaf tissue in a turfgrass. In selected embodiments, the fungal pathogen may be a fungus that causes dollar spot in a turfgrass. In selected embodiments, the fungal pathogen may be *Sclerotinia homoeocarpa*. In selected embodiments, the fungal pathogen may be a fungus that causes bentgrass dead spot or bermudagrass dead spot in a turfgrass. In alternative embodiments, the fungal pathogen may be *Ophiosphaerella agrostis*. In selected embodiments, the turfgrass and the plant may independently be one or more of: bentgrass, bluegrass, ryegrass, *fescue*, bermudagrass, bahiagrass, *zoysia*, beachgrass, wheatgrass, or carpetgrass. In alternative embodiments, the turfgrass and the plant may independently be one or more of: bentgrass, colonial bentgrass, perennial ryegrass, annual ryegrass, Kentucky bluegrass, common bermudagrass, hybrid bermudagrass, annual bluegrass, seashore *paspalum*, St. Augustinegrass, tall *fescue*, bahiagrass, zoysiagrass, centipedegrass, rough stalk bluegrass, buffalo grass, blue grama, or annual bentgrass. In selected embodiments, the turfgrass and the plant may independently be one or more of: creeping bentgrass or annual bluegrass.

In alternative embodiments, boscalid may be applied to the plant at a rate from about 0.02 to about 0.12 oz per 1000 square feet. In selected embodiments, the paraffinic oil may be applied to the plant at a rate from about 0.9 to about 32 oz/1000 square ft. In alternative embodiments, the paraffinic oil may be applied to the plant at a rate of about 8 oz/1000 square ft. In selected embodiments, the paraffinic oil may be applied to the plant at a rate of less than about 31 oz/1000 square ft.

DETAILED DESCRIPTION

This invention is based in part on the fortuitous discovery that fungicidal formulations containing paraffinic oil as an active agent, in combination with the fungicide boscalid, are surprisingly effective in controlling fungal disease, including dollar spot in turfgrasses. The Examples illustrate that combined use of paraffinic oil with boscalid provides an unexpected synergistic response in the control of dollar spot in turfgrass.

The paraffinic oil and boscalid may be provided as components of the same fungicidal composition. Accordingly, in an embodiment, there is provided a composition comprising a paraffinic oil and boscalid. In another embodiment, the composition may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. In an embodiment, the composition may be, for example, an emulsifiable concentrate containing the paraffinic oil, boscalid, and the emulsifier, which is thereafter prepared for use as a diluted oil-in-water (O/W) emulsion.

In another embodiment, the paraffinic oil and boscalid may be used in combination with a pigment. The paraffinic oil, boscalid, and the pigment may be provided as components of the same composition. Accordingly, in an embodiment, there is provided a composition comprising a paraffinic oil, boscalid, and a pigment. In a further embodiment, the composition may further comprise an emulsifier, a silicone surfactant, or a combination thereof. In alternative embodiments, the composition may further comprise an emulsifier. In selected embodiments, the composition may further comprise a silicone surfactant. In alternative embodiments, the composition may further comprise an emulsifier and a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the composition may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the composition may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. In an embodiment, the composition may be, for example, an emulsifiable concentrate containing the paraffinic oil, boscalid, the emulsifier, the pigment, and the silicone surfactant, which is thereafter prepared for use as a diluted oil-in-water (O/W) emulsion. In another embodiment, the composition may be, for example, an emulsifiable concentrate containing the paraffinic oil, boscalid, the emulsifier, the pigment, the silicone surfactant and the polyethylene glycol, which is thereafter prepared for use as a diluted oil-in-water (O/W) emulsion.

The paraffinic oil and boscalid may be provided as components of separate compositions. Accordingly, in an embodiment, there is provided a commercial package which comprises: a first composition comprising a paraffinic oil; and a second composition comprising boscalid. In another embodiment, the first and/or second compositions may further comprise an emulsifier. In an embodiment, the first composition may further comprise an emulsifier. In a further embodiment, the second composition may further comprise an emulsifier. In another embodiment, the first and second compositions may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant.

The paraffinic oil, boscalid, and pigment may be provided as components of two compositions. Accordingly, in an embodiment, there is provided a commercial package which comprises: a first composition comprising a paraffinic oil and boscalid; and a second composition comprising a pigment. In an embodiment, there is provided a commercial package which comprises: a first composition comprising a paraffinic oil and a pigment; and a second composition comprising boscalid. In an embodiment, there is provided a commercial package which comprises: a first composition comprising a paraffinic oil; and a second composition comprising boscalid and a pigment. In alternative embodiments, the first and/or second compositions may further comprise an emulsifier or a silicone surfactant or a combination thereof. In an embodiment, the first and/or second compositions may further comprise an emulsifier. In an embodiment, the first composition may further comprise an emulsifier. In alternative embodiments, the second composition may further comprise an emulsifier. In another embodiment, the first and second compositions may further comprise an emulsifier. In selected embodiments, the first and/or second compositions may further comprise a silicone surfactant. In another embodiment, the first composition may further comprise a silicone surfactant. In another embodiment, the second composition may further comprise a silicone surfactant. In alternative embodiments, the first and second compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first and/or second compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first and/or second compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant.

The paraffinic oil, boscalid, and the pigment may be provided as components of three compositions. In an embodiment, there is provided a commercial package which comprises: a first composition comprising a paraffinic oil; a second composition comprising boscalid; and a third composition comprising a pigment. In an embodiment, the first, second and/or third compositions may further comprise an emulsifier or a silicone surfactant or a combination thereof. In an embodiment, the first, second and/or third compositions may further comprise an emulsifier. In an embodiment, the first composition may further comprise an emulsifier. In another embodiment, the second composition may further comprise an emulsifier. In alternative embodiments, the third composition may further comprise an emulsifier. In an embodiment, the first and second compositions may further comprise an emulsifier. In another embodiment, the first and third compositions may further comprise an emulsifier. In a further embodiment, the second and third compositions may further comprise an emulsifier. In selected embodiments, the first, second and third compositions may further comprise an emulsifier. In an embodiment, the first, second and/or third compositions may further comprise a silicone surfactant. In an embodiment, the first composition may further comprise a silicone surfactant. In another embodiment, the second composition may further comprise a silicone surfactant. In alternative embodiments, the third composition may further comprise a silicone surfactant. In an embodiment, the first and second compositions may further comprise a silicone surfactant. In another embodiment, the first and third compositions may further comprise a silicone surfactant. In a further embodiment, the second and third compositions may further comprise a silicone surfactant. In alternative embodiments, the first, second and third compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first, second and/or third compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first, second and/or third compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant.

The first, second and/or third compositions of the commercial packages may be emulsifiable concentrates, which are thereafter prepared for use as a diluted oil-in-water (O/W) emulsion.

The emulsifiable concentrates may be prepared by admixing suitable amounts of the components of the emulsifiable concentrates, for example, the paraffinic oil, boscalid, pigment, emulsifier, silicone surfactant and/or polyethylene glycol, and mixing and/or applying shear until the emulsifiable concentrate is obtained. In an embodiment, there is provided a method of preparing an emulsifiable concentrate, the method comprising mixing, in any order, a paraffinic oil and boscalid. In alternative embodiments, the method may further comprise mixing, in any order, the paraffinic oil and boscalid with an emulsifier. In alternative embodiments, there is provided a method of preparing an emulsifiable concentrate, the method comprising mixing, in any order, a paraffinic oil, boscalid, a pigment and a silicone surfactant. In selected embodiments, the method may further comprise mixing, in any order, the paraffinic oil, boscalid, the pigment and the silicone surfactant with an emulsifier. In alternative embodiments, the pigment may be dispersed in water and the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the pigment may be dispersed in oil and the method may further comprise mixing, in any order, the paraffinic oil, boscalid, the pigment, the silicone surfactant, and the emulsifier with a polyethylene glycol of the formula IV. In another embodiment, the pigment may be dispersed in oil and the method may further comprise mixing, in any order, the paraffinic oil, boscalid, the pigment, the silicone surfactant, and the emulsifier with a polyethylene glycol of the formula IV, and the emulsifier may comprise a natural or synthetic alcohol ethoxylate, a polymeric surfactant, a sorbitan fatty acid ester, or a combination thereof.

In an embodiment, the emulsifiable concentrates may be prepared for use as separately diluted compositions. The diluted compositions may be used simultaneously or separately for controlling a fungal pathogen of a plant.

In another embodiment, the emulsifiable concentrates may be prepared for use as a diluted O/W emulsion, for example, by tank mixing the emulsifiable concentrates. Accordingly, the paraffinic oil and boscalid may be provided as components of an O/W emulsion. Accordingly, in an embodiment, there is provided a composition comprising a paraffinic oil, boscalid and water. In selected embodiments, the composition may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. The paraffinic oil, boscalid, and pigment may be provided as components of an O/W emulsion. Accordingly, in an embodiment, there is provided a composition comprising a paraffinic oil, boscalid, a pigment and water. In alternative embodiments, the composition may further comprise an emulsifier or a silicone surfactant or a combination thereof. In selected embodiments, the composition may further comprise an emulsifier. In alternative embodiments, the composition may further comprise a silicone surfactant. In selected embodiments, the composition may further comprise an emulsifier and a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the composition may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the composition may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. The O/W emulsions may be used for controlling a fungal pathogen of a plant.

The paraffinic oil and boscalid may be used to prepare O/W emulsions. Accordingly, in an embodiment, there is provided a use of a paraffinic oil and boscalid for preparing an O/W emulsion effective to control a fungal pathogen of a plant. In alternative embodiments, there is also provided a method of preparing an O/W emulsion effective to control a fungal pathogen of a plant, the method comprising mixing, in any order, a paraffinic oil and boscalid. In alternative embodiments, the paraffinic oil and boscalid may be used or mixed with an emulsifier for preparing the O/W emulsion. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. The paraffinic oil, boscalid, and the pigment may be used to prepare O/W emulsions. Accordingly, in another embodiment, there is provided a use of a paraffinic oil, boscalid and a pigment for preparing an O/W emulsion effective to control a fungal pathogen of a plant. In alternative embodiments, there is also provided a method of preparing an O/W emulsion effective to control a fungal pathogen of a plant, the method comprising mixing, in any order, a paraffinic oil, boscalid and a pigment. In alternative embodiments, the paraffinic oil, boscalid and the pigment may be used or mixed with an emulsifier or a silicone surfactant or a combination thereof for preparing the O/W emulsion. In selected embodiments, the paraffinic oil, boscalid and the pigment may be used or mixed with an emulsifier for preparing the O/W emulsion. In alternative embodiments, the paraffinic oil, boscalid and the pigment may be used or mixed with a silicone surfactant for preparing the O/W emulsion. In selected embodiments, the paraffinic oil, boscalid and the pigment may be used or mixed with an emulsifier and a silicone surfactant for preparing the O/W emulsion. In an embodiment, the pigment may be dispersed in water and the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, there is provided a use of a paraffinic oil, boscalid, an emulsifier, a pigment, a silicone surfactant and a polyethylene glycol of the formula IV for preparing an O/W emulsion effective to control a fungal pathogen of a plant, wherein the pigment may be dispersed in oil. In another embodiment, there is provided a use of a paraffinic oil, boscalid, an emulsifier, a pigment, a silicone surfactant and a polyethylene glycol of the formula IV for preparing an O/W emulsion effective to control a fungal pathogen of a plant, wherein the pigment may be dispersed in oil, and the emulsifier may comprise a natural or synthetic alcohol ethoxylate, a polymeric surfactant, a sorbitan fatty acid ester, or a combination thereof. In alternative embodiments, there is provided a method of preparing an O/W emulsion effective to control a fungal pathogen of a plant, the method comprising mixing, in any order, a paraffinic oil, boscalid, an emulsifier, a pigment, a silicone surfactant and a polyethylene glycol of the formula IV, wherein the pigment may be dispersed in oil. In selected embodiments, there is provided a method of preparing an O/W emulsion effective to control a fungal pathogen of a plant, the method comprising mixing, in any order, a paraffinic oil, boscalid, an emulsifier, a pigment, a silicone surfactant and a polyethylene glycol of the formula IV, wherein the pigment may be dispersed in oil, and the emulsifier may comprise a natural or synthetic alcohol ethoxylate, a polymeric surfactant, a sorbitan fatty acid ester, or a combination thereof. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. The O/W emulsions may be used for controlling a fungal pathogen of a plant.

In an embodiment, there is provided a use of a composition comprising a paraffinic oil and boscalid for preparing an O/W emulsion effective to control a fungal pathogen of a plant. In alternative embodiments, there is also provided a method of preparing an O/W emulsion effective to control a fungal pathogen of a plant, the method comprising mixing a composition comprising a paraffinic oil and boscalid with water. In selected embodiments, the composition may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. In another embodiment, there is provided a use of a composition comprising a paraffinic oil, boscalid and a pigment for preparing an O/W emulsion effective to control a fungal pathogen of a plant. In alternative embodiments, there is also provided a method of preparing an O/W emulsion effective to control a fungal pathogen of a plant, the method comprising mixing a composition comprising a paraffinic oil, boscalid and a pigment with water. In selected embodiments, the composition may further comprise an emulsifier or a silicone surfactant or a combination thereof. In alternative embodiments, the composition may further comprise an emulsifier. In another embodiment, the composition may further comprise a silicone surfactant. In selected embodiments, the composition may further comprise an emulsifier and a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the composition may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the composition may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. The O/W emulsions may be used for controlling a fungal pathogen of a plant.

In an embodiment, there is provided a use of a first composition comprising a paraffinic oil, and a second composition comprising boscalid for preparing an O/W emulsion effective to control a fungal pathogen of a plant. In selected embodiments, there is also provided a method of preparing an O/W emulsion effective to control a fungal pathogen of a plant, the method comprising mixing, in any order, a first composition comprising a paraffinic oil, and a second composition comprising boscalid. In an embodiment, the first and/or second compositions may further comprise an emulsifier. In another embodiment, the first composition may further comprise an emulsifier. In an embodiment, the second composition may further comprise an emulsifier. In alternative embodiments, the first and second compositions may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. In an embodiment, there is provided a use of a first composition comprising a paraffinic oil and boscalid, and a second composition comprising a pigment for preparing an O/W emulsion effective to control a fungal pathogen of a plant. In an embodiment, there is provided a use of a first composition comprising a paraffinic oil and a pigment, and a second composition comprising boscalid for preparing an O/W emulsion effective to control a fungal pathogen of a plant. In an embodiment, there is provided a use of a first composition comprising a paraffinic oil, and a second composition comprising boscalid and a pigment for preparing an O/W emulsion effective to control a fungal pathogen of a plant. In an embodiment, there is provided a method of preparing an O/W emulsion effective to control a fungal pathogen of a plant, the method comprising mixing, in any order, a first composition comprising a paraffinic oil and boscalid, and a second composition comprising a pigment. In an embodiment, there is provided a method of preparing an O/W emulsion effective to control a fungal pathogen of a plant, the method comprising mixing, in any order, a first composition comprising a paraffinic oil and a pigment, and a second composition comprising boscalid. In an embodiment, there is provided a method of preparing an O/W emulsion effective to control a fungal pathogen of a plant, the method comprising mixing, in any order, a first composition comprising a paraffinic oil, and a second composition comprising boscalid and a pigment. In selected embodiments, the first and/or second composition may further comprise an emulsifier or a silicone surfactant or a combination thereof. In an embodiment, the first and/or second compositions may further comprise an emulsifier. In another embodiment, the first composition may further comprise an emulsifier. In an embodiment, the second composition may further comprise an emulsifier. In a further embodiment, the first and second compositions may further comprise an emulsifier. In another embodiment, the first and/or second compositions may further comprise a silicone surfactant. In an embodiment, the first composition may further comprise a silicone surfactant. In another embodiment, the second composition may further comprise a silicone surfactant. In selected embodiments, the first and second compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first and/or second compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first and/or second compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. The O/W emulsions may be used for controlling a fungal pathogen of a plant.

In an embodiment, there is provided a use of a first composition comprising a paraffinic oil, a second composition comprising boscalid, and a third composition comprising a pigment for preparing an O/W emulsion effective to control a fungal pathogen of a plant. In selected embodiments, there is also provided a method of preparing an O/W emulsion effective to control a fungal pathogen of a plant, the method comprising mixing, in any order, a first composition comprising a paraffinic oil, a second composition comprising boscalid, and a third composition comprising a pigment. In an embodiment, the first, second and/or third compositions may further comprise an emulsifier or a silicone surfactant or a combination thereof. In an embodiment, the first, second and/or third compositions may further comprise an emulsifier. In another embodiment, the first composition may further comprise an emulsifier. In an embodiment, the second composition may further comprise an emulsifier. In a further embodiment, the third composition may further comprise an emulsifier. In alternative embodiments, the first and second compositions may further comprise an emulsifier. In selected embodiments, the first and third compositions may further comprise an emulsifier. In alternative embodiment, the second and third compositions may further comprise an emulsifier. In selected embodiments, the first, second and third compositions may further comprise an emulsifier. In another embodiment, the first, second and/or third compositions may further comprise a silicone surfactant. In another embodiment, the first composition may further comprise a silicone surfactant. In a further embodiment, the second composition may further comprise a silicone surfactant. In an embodiment, the third composition may further comprise a silicone surfactant. In an embodiment, the first and second compositions may further comprise a silicone surfactant. In another embodiment, the first and third compositions may further comprise a silicone surfactant. In a further embodiment, the second and third compositions may further comprise a silicone surfactant. In alternative embodiments, the first, second and third compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first, second and/or third compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first, second and/or third compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. The O/W emulsions may be used for controlling a fungal pathogen of a plant.

O/W emulsions may be prepared by admixing suitable amounts of the components of the O/W emulsions, for example, the paraffinic oil, boscalid, pigment, emulsifier, silicone surfactant, and/or water, and mixing and/or applying shear until the emulsion is obtained. In alternative embodiments, O/W emulsions may be prepared by admixing suitable amounts of the components of the O/W emulsions, for example, the paraffinic oil, boscalid, the pigment, the emulsifier, the silicone surfactant, the polyethylene glycol, and/or water, and mixing and/or applying shear until the emulsion is obtained. Alternatively, the separate components may be combined at the nozzle of a spray gun to form the O/W emulsion.

In another embodiment, there is provided a use of a paraffinic oil and boscalid, in any order, for controlling a fungal pathogen of a plant. In alternative embodiments, the paraffinic oil may be used in an amount that is synergistically effective when applied to a plant for controlling a fungal pathogen of the plant. In an embodiment, boscalid may be used in an amount that is synergistically effective when applied to a plant for controlling a fungal pathogen of the plant. In selected embodiments, the paraffinic oil and boscalid may be used in amounts that are synergistically effective when applied to a plant for controlling a fungal pathogen of the plant. In a further embodiment, there is provided a use of a paraffinic oil, boscalid, and a pigment, in any order, for controlling a fungal pathogen of a plant. In alternative embodiments, the paraffinic oil may be used in an amount that is synergistically effective when applied to a plant for controlling a fungal pathogen of the plant. In an embodiment, boscalid may be used in an amount that is synergistically effective when applied to a plant for controlling a fungal pathogen of the plant. In an embodiment, the pigment may be used in an amount that is synergistically effective when applied to a plant for controlling a fungal pathogen of the plant. In alternative embodiments, the paraffinic oil and boscalid may be used in amounts that are synergistically effective when applied to a plant for controlling a fungal pathogen of the plant. In alternative embodiments, the paraffinic oil and the pigment may be used in amounts that are synergistically effective when applied to a plant for controlling a fungal pathogen of the plant. In alternative embodiments, boscalid and the pigment may be used in amounts that are synergistically effective when applied to a plant for controlling a fungal pathogen of the plant. In alternative embodiments, the paraffinic oil, boscalid, and the pigment may be used in amounts that are synergistically effective when applied to a plant for controlling a fungal pathogen of the plant. Also provided is a use of any of the O/W emulsions as described herein for controlling a fungal pathogen of a plant.

In an embodiment, there is provided a use of a composition comprising a paraffinic oil and boscalid for controlling a fungal pathogen of a plant. In another embodiment, the composition may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. In another embodiment, there is provided a use of a composition comprising a paraffinic oil, boscalid and a pigment for controlling a fungal pathogen of a plant. In selected embodiments, the composition may further comprise an emulsifier or a silicone surfactant or a combination thereof. In another embodiment, the composition may further comprise an emulsifier. In a further embodiment, the composition may further comprise a silicone surfactant. In selected embodiments, the composition may further comprise an emulsifier and a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the composition may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the composition may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. In selected embodiments, the compositions may further comprise water.

The paraffinic oil and boscalid may be used as components of two compositions for controlling a fungal pathogen of a plant. Accordingly, in an embodiment, there is provided a use, in any order, of a first composition comprising a paraffinic oil, and a second composition comprising boscalid, for controlling a fungal pathogen of a plant. In an embodiment, the first and/or second compositions may further comprise an emulsifier. In another embodiment, the first composition may further comprise an emulsifier. In an embodiment, the second composition may further comprise an emulsifier. In selected embodiments, the first and second compositions may further comprise an emulsifier. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In selected embodiments, the paraffinic oil and boscalid may be present in amounts that are synergistically effective when applied to a plant for controlling a fungal pathogen of the plant. The paraffinic oil, boscalid, and the pigment may be used as components of two compositions for controlling a fungal pathogen of a plant. Accordingly, in an embodiment, there is provided a use, in any order, of a first composition comprising a paraffinic oil and boscalid, and a second composition comprising a pigment for controlling a fungal pathogen of a plant. In an embodiment, there is provided a use, in any order, of a first composition comprising a paraffinic oil, and a second composition comprising boscalid and a pigment for controlling a fungal pathogen of a plant. In an embodiment, there is provided a use, in any order, of a first composition comprising a paraffinic oil and a pigment, and a second composition comprising boscalid for controlling a fungal pathogen of a plant. In alternative embodiments, the first and/or second compositions may further comprise an emulsifier or a silicone surfactant or a combination thereof. In an embodiment, the first and/or second compositions may further comprise an emulsifier. In another embodiment, the first composition may further comprise an emulsifier. In a further embodiment, the second composition may further comprise an emulsifier. In an embodiment, the first and second compositions may further comprise an emulsifier. In an embodiment, the first and/or second compositions may further comprise a silicone surfactant. In another embodiment, the first composition may further comprise a silicone surfactant. In a further embodiment, the second composition may further comprise a silicone surfactant. In selected embodiments, the first and second compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first and/or second compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first and/or second compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. In selected embodiments, the first and/or second compositions may further comprise water.

The paraffinic oil, boscalid, and pigment may be used as components of three compositions for controlling a fungal pathogen of a plant. Accordingly, in an embodiment, there is provided a use, in any order, of a first composition comprising a paraffinic oil, a second composition comprising boscalid, and a third composition comprising a pigment, for controlling a fungal pathogen of a plant. In alternative embodiments, the first, second and/or third compositions may further comprise an emulsifier or a silicone surfactant or a combination thereof. In another embodiment, the first, second and/or third compositions may further comprise an emulsifier. In another embodiment, the first composition may further comprise an emulsifier. In a further embodiment, the second composition may further comprise an emulsifier. In an embodiment, the third composition may further comprise an emulsifier. In an embodiment, the first and second compositions may further comprise an emulsifier. In another embodiment, the first and third compositions may further comprise an emulsifier. In a further embodiment, the second and third compositions may further comprise an emulsifier. In selected embodiments, the first, second and third compositions may further comprise an emulsifier. In another embodiment, the first, second and/or third compositions may further comprise a silicone surfactant. In another embodiment, the first composition may further comprise a silicone surfactant. In a further embodiment, the second composition may further comprise a silicone surfactant. In an embodiment, the third composition may further comprise a silicone surfactant. In an embodiment, the first and second compositions may further comprise a silicone surfactant. In another embodiment, the first and third compositions may further comprise a silicone surfactant. In a further embodiment, the second and third compositions may further comprise a silicone surfactant. In alternative embodiments, the first, second and third compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first, second and/or third compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first, second and/or third compositions may further comprise a polyethylene glycol of the formula IV. In alternative embodiments, the paraffinic oil may be present in an amount that is synergistically effective when applied to a plant for controlling a fungal pathogen of the plant. In an embodiment, boscalid may be present in an amount that is synergistically effective when applied to a plant for controlling a fungal pathogen of the plant. In an embodiment, the pigment may be present in an amount that is synergistically effective when applied to a plant for controlling a fungal pathogen of the plant. In alternative embodiments, the paraffinic oil and boscalid may be present in amounts that are synergistically effective when applied to a plant for controlling a fungal pathogen of the plant. In alternative embodiments, the paraffinic oil and the pigment may be present in amounts that are synergistically effective when applied to a plant for controlling a fungal pathogen of the plant. In alternative embodiments, boscalid and the pigment may be present in amounts that are synergistically effective when applied to a plant for controlling a fungal pathogen of the plant. In alternative embodiments, the paraffinic oil, boscalid, and the pigment may be present in amounts that are synergistically effective when applied to a plant for controlling a fungal pathogen of the plant. In selected embodiments, the first and/or second and/or third compositions may further comprise water.

Also provided is a method of controlling a fungal pathogen of a plant, the method comprising applying to the plant, in any order, a paraffinic oil and boscalid. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In selected embodiments, the paraffinic oil and boscalid may be applied in amounts that are synergistically effective for controlling a fungal pathogen of the plant. In another embodiment, there is provided a method of controlling a fungal pathogen of a plant, the method comprising applying to the plant, in any order, a paraffinic oil, boscalid, and a pigment. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In an embodiment, the pigment may be applied in an amount that is synergistically effective for controlling a fungal pathogen of the plant. In alternative embodiments, the paraffinic oil and boscalid may be applied in amounts that are synergistically effective for controlling a fungal pathogen of the plant. In alternative embodiments, the paraffinic oil and the pigment may be applied in amounts that are synergistically effective for controlling a fungal pathogen of the plant. In alternative embodiments, boscalid and the pigment may be applied in amounts that are synergistically effective for controlling a fungal pathogen of the plant. In alternative embodiments, the paraffinic oil, boscalid, and the pigment may be applied in amounts that are synergistically effective for controlling a fungal pathogen of the plant.

In an embodiment, there is provided a method of controlling a fungal pathogen of a plant, the method comprising applying to the plant a composition comprising a paraffinic oil, in combination with boscalid. In another embodiment, the composition may further comprise an emulsifier. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In selected embodiments, the paraffinic oil and boscalid may be applied in amounts that are synergistically effective for controlling a fungal pathogen of the plant. In an embodiment, there is provided a method of controlling a fungal pathogen of a plant, the method comprising applying to the plant a composition comprising a paraffinic oil and a pigment, in combination with boscalid. In selected embodiments, the composition may further comprise an emulsifier or a silicone surfactant or a combination thereof. In another embodiment, the composition may further comprise an emulsifier. In a further embodiment, the composition may further comprise a silicone surfactant. In selected embodiments, the composition may further comprise an emulsifier and a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, and the composition may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the composition may further comprise a polyethylene glycol of the formula IV. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In an embodiment, the pigment may be applied in an amount that is synergistically effective for controlling a fungal pathogen of the plant. In alternative embodiments, the paraffinic oil and boscalid may be applied in amounts that are synergistically effective for controlling a fungal pathogen of the plant. In alternative embodiments, the paraffinic oil and the pigment may be applied in amounts that are synergistically effective for controlling a fungal pathogen of the plant. In alternative embodiments, boscalid and the pigment may be applied in amounts that are synergistically effective for controlling a fungal pathogen of the plant. In alternative embodiments, the paraffinic oil, boscalid, and the pigment may be applied in amounts that are synergistically effective for controlling a fungal pathogen of the plant. In selected embodiments, the compositions may further comprise water.

The paraffinic oil and boscalid may be applied to the plant as components of two compositions. Accordingly, in an embodiment, there is provided a method of controlling a fungal pathogen of a plant, the method comprising applying, in any order, to the plant a first composition comprising a paraffinic oil, and a second composition comprising boscalid. In another embodiment, the first and/or second compositions may further comprise an emulsifier. In an embodiment, the first composition may further comprise an emulsifier. In an embodiment, the second composition may further comprise an emulsifier. In selected embodiments, the first and second compositions may further comprise an emulsifier. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In selected embodiments, the paraffinic oil and boscalid may be applied in amounts that are synergistically effective for controlling a fungal pathogen of the plant. The paraffinic oil, boscalid, and the pigment may be applied to the plant as components of two compositions. Accordingly, in an embodiment, there is provided a method of controlling a fungal pathogen of a plant, the method comprising applying, in any order, to the plant a first composition comprising a paraffinic oil, and a second composition comprising boscalid and a pigment. In an embodiment, there is provided a method of controlling a fungal pathogen of a plant, the method comprising applying, in any order, to the plant a first composition comprising a paraffinic oil and boscalid, and a second composition comprising a pigment. In an embodiment, there is provided a method of controlling a fungal pathogen of a plant, the method comprising apply, in any order, to the plant a first composition comprising a paraffinic oil and a pigment, and a second composition comprising boscalid. In alternative embodiments, the first and/or second compositions may further comprise an emulsifier or a silicone surfactant or a combination thereof. In another embodiment, the first and/or second compositions may further comprise an emulsifier. In another embodiment, the first composition may further comprise an emulsifier. In a further embodiment, the second composition may further comprise an emulsifier. In alternative embodiments, the first and second compositions may further comprise an emulsifier. In another embodiment, the first and/or second compositions may further comprise a silicone surfactant. In an embodiment, the first composition may further comprise a silicone surfactant. In another embodiment, the second composition may further comprise a silicone surfactant. In a further embodiment, the first and second compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first and/or second compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first and/or second compositions may further comprise a polyethylene glycol of the formula IV. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In an embodiment, the pigment may be applied in an amount that is synergistically effective for controlling a fungal pathogen of the plant. In alternative embodiments, the paraffinic oil and boscalid may be applied in amounts that are synergistically effective for controlling a fungal pathogen of the plant. In alternative embodiments, the paraffinic oil and the pigment may be applied in amounts that are synergistically effective for controlling a fungal pathogen of the plant. In alternative embodiments, boscalid and the pigment may be applied in amounts that are synergistically effective for controlling a fungal pathogen of the plant. In alternative embodiments, the paraffinic oil, boscalid, and the pigment may be applied in amounts that are synergistically effective for controlling a fungal pathogen of the plant. The paraffinic oil, boscalid, and pigment may be applied to the plant as components of three compositions. Accordingly, in an embodiment, there is provided a method of controlling a fungal pathogen of a plant, the method comprising applying, in any order, to the plant a first composition comprising a paraffinic oil, a second composition comprising boscalid, and a third composition comprising a pigment. In alternative embodiments, the first, second and/or third compositions may further comprise an emulsifier or a silicone surfactant or a combination thereof. In another embodiment, first, second and/or third compositions may further comprise an emulsifier. In an embodiment, the first composition may further comprise an emulsifier. In an embodiment, the second composition may further comprise an emulsifier. In a further embodiment, the third composition may further comprise an emulsifier. In selected embodiments, the first and second compositions may further comprise an emulsifier. In alternative embodiments, the first and third compositions may further comprise an emulsifier. In an embodiment, the second and third compositions may further comprise an emulsifier. In a further embodiment, the first, second and third compositions may further comprise an emulsifier. In another embodiment, the first, second and/or third compositions may further comprise a silicone surfactant. In an embodiment, the first composition may further comprise a silicone surfactant. In a further embodiment, the second composition may further comprise a silicone surfactant. In another embodiment, the third composition may further comprise a silicone surfactant. In selected embodiments, the first and second compositions may further comprise a silicone surfactant. In alternative embodiments, the first and third compositions may further comprise a silicone surfactant. In an embodiment, the second and third compositions may further comprise a silicone surfactant. In a further embodiment, the first, second and third compositions may further comprise a silicone surfactant. In an embodiment, the emulsifier may comprise a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof. In another embodiment, the first, second and/or third compositions may further comprise a polyethylene glycol of the formula IV. In another embodiment, the emulsifier may comprise a natural or synthetic alcohol ethoxylate, a polymeric surfactant, a sorbitan fatty acid ester, or a combination thereof, and the first, second and/or third compositions may further comprise a polyethylene glycol of the formula IV. In alternative embodiments, the paraffinic oil may be applied in an amount that is synergistically effective for controlling a fungal pathogen of the plant. In an embodiment, boscalid may be applied in an amount that is synergistically effective for controlling a fungal pathogen of the plant. In an embodiment, the pigment may be applied in an amount that is synergistically effective for controlling a fungal pathogen of the plant. In alternative embodiments, the paraffinic oil and boscalid may be applied in amounts that are synergistically effective for controlling a fungal pathogen of the plant. In alternative embodiments, the paraffinic oil and the pigment may be applied in amounts that are synergistically effective for controlling a fungal pathogen of the plant. In alternative embodiments, boscalid and the pigment may be applied in amounts that are synergistically effective for controlling a fungal pathogen of the plant. In alternative embodiments, the paraffinic oil, boscalid, and the pigment may be applied in amounts that are synergistically effective for controlling a fungal pathogen of the plant. In selected embodiments, the first and/or second and/or third compositions may further comprise water.

Compositions of the invention may be applied to the plant to provide a dosage of the active agents that is sufficient to effectively control the fungal pathogen. The compositions may be reapplied as required. The compositions may be applied to the plant by spraying, misting, sprinkling, pouring, or any other suitable method.

In an embodiment, the paraffinic oil may comprise, for example, an oil enriched in paraffin. In an embodiment, the paraffinic oil may comprise, for example, a paraffin having a number of carbon atoms ranging from about 12 to about 50 or any combinations thereof. In an embodiment, the paraffinic oil may comprise, for example, a paraffin having a number of carbon atoms ranging from about 12 to about 40 or any combinations thereof. In an embodiment, the paraffinic oil may comprise, for example, a paraffin having a number of carbon atoms ranging from about 16 to about 40 or any combinations thereof. In an embodiment, the paraffinic oil may comprise, for example, a paraffin having a number of carbon atoms ranging from about 16 to about 35 or any combinations thereof. In an embodiment, the paraffinic oil may comprise, for example, a paraffin having a number of carbon atoms ranging from about 15 to about 30 or any combinations thereof. In an embodiment, the paraffinic oil may comprise, for example, a paraffin having a number of carbon atoms ranging from about 18 to about 25 or any combinations thereof. In an embodiment, the paraffinic oil may comprise, for example, a paraffin having a number of carbon atoms ranging from about 12 to about 21 or any combinations thereof. In an embodiment, the paraffinic oil may comprise, for example, a paraffin having a number of carbon atoms ranging from about 20 to about 35. In an embodiment, the paraffinic oil may comprise, for example, a paraffin having an average number of carbon atoms that is less than or equal to about 20. In an embodiment, the paraffinic oil may comprise, for example, a paraffin having an average number of carbon atoms ranging from about 12 to about 20. In an embodiment, the paraffinic oil may comprise, for example, a paraffin having an average number of carbon atoms ranging from about 16 to about 30. In an embodiment, the paraffinic oil may comprise, for example, a paraffin having an average number of carbon atoms ranging from about 25 to about 30. In an embodiment, the paraffinic oil may comprise, for example, a paraffin having an average number of carbon atoms of about 16 or about 27. In an embodiment, the paraffinic oil may comprise, for example, a paraffin having an average number of carbon atoms of about 16. In an embodiment, the paraffinic oil may comprise, for example, a paraffin having an average number of carbon atoms of about 27. In an embodiment, the paraffinic oil may comprise, for example, a paraffin having an average number of carbon atoms of about 23. In an embodiment, the paraffinic oil may comprise, for example, a paraffin having a number of carbon atoms ranging from about 16 to about 40 with an average number of carbon atoms of about 27. In an embodiment, the paraffinic oil may comprise, for example, a paraffin having a number of carbon atoms ranging from about 16 to about 35 and having an average number of carbon atoms of about 23. In an embodiment, the paraffinic oil may comprise, for example, a paraffin having a number of carbon atoms ranging from about 12 to about 21 with an average number of carbon atoms of about 16. In an embodiment, the paraffin may be, for example, an isoparaffin. In an embodiment, the paraffin may be, for example, a synthetic isoparaffin.

In an embodiment, paraffin may be present in the paraffinic oil in an amount, for example, of at least about 80%. In an embodiment, paraffin may be present in the paraffinic oil in an amount, for example, of at least about 90%. In an embodiment, paraffin may be present in the paraffinic oil in an amount, for example, of at least about 99%.

In selected embodiments, the paraffinic oil has been refined to remove compounds that are associated with plant injury, for example, aromatic compounds or compounds containing sulfur, nitrogen, or oxygen. In an embodiment, the paraffinic oil may comprise, for example, low levels of aromatic compounds and/or compounds containing sulfur, nitrogen, or oxygen. In an embodiment, the paraffinic oil may comprise, for example, less than about 10 wt % of aromatic compounds and/or compounds containing sulfur, nitrogen, or oxygen. In an embodiment, the paraffinic oil may comprise, for example, less than about 5 wt % of aromatic compounds and/or compounds containing sulfur, nitrogen, or oxygen. In an embodiment, the paraffinic oil may comprise, for example, less than about 2 wt % of aromatic compounds and/or compounds containing sulfur, nitrogen, or oxygen. In an embodiment, the paraffinic oil has substantially no content of aromatic compounds and/or compounds containing sulfur, nitrogen, or oxygen.

Non-limiting examples of suitable paraffinic oils may include, HT100, High Flash Jet, LSRD, and N65DW (available from Petro-Canada, Calgary, AB, Canada).

The expression "oil-in-water (O/W) emulsion" may include, for example, a dispersed system containing at least two normally immiscible phases, one being dispersed as droplets in the other. Emulsions are thermodynamically unstable due to excess free energy associated with the surface of the dispersed droplets such that the particles tend to flocculate (clumping together of dispersed droplets or particles) and subsequently coalesce (fusing together of agglomerates into a larger drop or droplets) to decrease the surface energy. If these droplets fuse, the emulsion will "break" (i.e., the phases will separate) destroying the emulsion and making it difficult to prepare formulations that have a suitable shelf-life for storage. To prevent or slow "breaking" of an emulsion, an emulsifying agent or emulsifier is often added. The type and concentration of a particular emulsifying agent will depend, inter alia, on the emulsion phase components and the desired result.

In an embodiment, the emulsifier may be, for example, a "fast break" or "quick break" emulsifier. A "fast break" or "quick break" emulsifier allows the paraffinic oil to be quickly released from the O/W emulsion upon application to the turfgrass for contact of pests thereon. When a "fast break" or "quick break" emulsifier is present in a suitable amount (for example a selected proportion or ratio with respect to the paraffinic oil), the resulting "fast break" or "quick break" O/W emulsion quickly releases the oil phase upon application to the turfgrass. Consequently, there is less runoff of the O/W emulsion from the grass blades as compared to more stable O/W emulsions such that a sufficient amount of oil adheres to the turfgrass for a sufficient amount of time to effectively contact and control associated turfgrass pests. In an embodiment, for example, the oil phase resides on the turfgrass for a period of not less than one hour. In an embodiment, for example, the oil phase resides on the turfgrass for a period of from not less than 1 hour but not more than 30 days. In an embodiment, the "fast break" or "quick break" emulsion may be, for example, an emulsion having an oil phase that, after mixing with water, is reconstituted in 0.5 to 15 minutes according to the following test:
1. Fill 100 mL graduated cylinder with tap water.
2. Add 1 mL of emulsified oil.
3. Invert graduated cylinder 5 times.
4. Using a stop watch and human observation, measure how long it takes for the oil phase to reconstitute after inversion (step 3).
In selected embodiments, the oil phase may be, for example, reconstituted in 2 to 5 minutes, or 3 to 5 minutes, or 4 to 5 minutes, or 2 to 4 minutes, or 3 to 4 minutes, or 2 to 3 minutes, or 2 minutes, or 3 minutes, or 4 minutes, or 5 minutes according to the test. The "fast break" or "quick break" property of the O/W emulsion must be balanced with the need to provide an O/W emulsion with a suitable shelf life under suitable storing conditions, and for a suitable timeframe.

In selected embodiments, the emulsifier may be, for example, a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or any combination thereof.

In alternative embodiments, the emulsifier may be, for example, a natural or synthetic alcohol ethoxylate, a polymeric surfactant, a sorbitan fatty acid ester, or any combination thereof.

In selected embodiments, the natural or synthetic alcohol ethoxylate may be, for example, a polyoxyethylene (4 to 12) lauryl ether (C12), polyoxyethylene (10) cetyl ether (C16), polyoxyethylene (10) stearyl ether (C18), polyoxyethylene (10) oleyl ether (C18 mono-unsaturated), a polyoxyethylene (2 to 11) C12-C15 alcohol, a polyoxyethylene (3 to 9) C11-C14 alcohol, a polyoxyethylene (9) C12-C14 alcohol, a polyoxyethylene (11) C16-C18 alcohol, a polyoxyethylene (20) C12-C15 alcohol, or any combination thereof. In an embodiment, the natural or synthetic alcohol ethoxylate may be, for example, a polyoxyethylene (4 to 7) lauryl ether (C12), polyoxyethylene (10) cetyl ether (C16), a polyoxyethylene (2 to 11) C12-C15 alcohol, a polyoxyethylene (3 to 9) C11-C14 alcohol, a polyoxyethylene (9) C12-C14 alcohol, or any combination thereof.

In some embodiments, the alcohol alkoxylate may be, for example, a butyl ether polyoxyethylene/polyoxypropylene block copolymer.

In alternative embodiments, the alkyl polysaccharide may be, for example, a C8-C11 alkylpolysaccharide or any combination thereof. The glycerol oleate may be, for example, a glycerol mono-, di-, tri-oleate, or any combination thereof. The polyoxyethylene-polyoxypropylene block copolymer may be, for example, a polyoxyethylene-polyoxypropylene block copolymer having a molecular weight of about 1100 to about 11400 and 10 to 80% EO. The alkyl phenol ethoxylate may be, for example, a nonyl phenol ethoxylate, a dodecyl phenol ethoxylate, or any combination thereof. In an embodiment, the nonyl phenol ethoxylate may be, for example, a polyoxyethylene (2 to 8) nonylphenol.

In selected embodiments, the polymeric surfactant may be, for example, a graft copolymer, a random copolymer, or any combination thereof. In an embodiment, the graft copolymer may be, for example, a polymethacrylic acid and acrylate with polyoxyethylene chains. In an embodiment, the random copolymer may be, for example, a random copolymer having ester and ether groups.

In alternative embodiments, the polyethylene glycol may be, for example, a polyethylene glycol having MW: about 200 to about 8000; MW: about 400 PEG dioleate; or MW: about 600 PEG dioleate.

In alternative embodiments, the sorbitan fatty acid ester ethoxylate may be, for example, polyoxyethylene (20) sorbitan tristearate, polyoxyethylene (20) sorbitan monooleate, polyoxyethylene (5) sorbitan monooleate, polyoxyethylene (20) sorbitan trioleate, or any combination thereof. In an embodiment, the sorbitan fatty acid ester may be, for example, a sorbitan tristearate, a sorbitan triolate, or any combination thereof.

In some embodiments, the emulsifier may be, for example, an alkyl phenol ethoxylate, a mixture of an ethoxylated alcohol and a glycerol oleate, or any combination thereof. In an embodiment, the emulsifier may be, for example, an alkyl phenol ethoxylate. In an embodiment, the emulsifier may be, for example, a nonylphenolethoxylate, a dodecylphenolethoxylate, or any combination thereof. In an embodiment, the emulsifier may be, for example, a nonylphenolethoxylate. In an embodiment, the emulsifier may be, for example, a dodecylphenolethoxylate. In an embodiment, the emulsifier may be, for example, a mixture of an ethoxylated alcohol and a glycerol oleate. In an embodiment, the emulsifier may be, for example, a C10 to C16 alcohol ethoxylate and a glycerol oleate combination. In an embodiment, the emulsifier may be, for example, polyoxyethylene lauryl ether, C10 to C16 alcohol ethoxylates, and glycerol oleate. In an embodiment, the emulsifier may be, for example, ethoxylated alcohols having primary C5-C20 carbon chains with an average of about 2 to about 7 ethoxylation groups, and a glycerol oleate. In an embodiment, the emulsifier may be, for example, a polyoxyethylene (11) C16-18 alcohol. In an embodiment, the emulsifier may be, for example, sorbitan tristearate.

Non-limiting examples of suitable emulsifiers include AL3149 (available from Uniqema), AL3313 (available from Uniqema), PC Emuls Green (available from Petro-Canada, Calgary, AB, Canada), Lutensol™ AT11 (available from BASF), SPAN65 (available from Uniqema), and S-MAZ™65K (available from BASF).

In selected embodiments, the weight ratio of the paraffinic oil to the emulsifier may be, for example, from about 95:5 to about 99.95:0.05. In an embodiment, the weight ratio of the paraffinic oil to the emulsifier may be, for example, from about 98.0:2 to about 99.9:0.1. In an embodiment, the weight ratio of the paraffinic oil to the emulsifier may be, for example, from about 98.5:1.5 to about 99.5:0.5. In an embodiment, the weight ratio of the paraffinic oil to the emulsifier may be, for example, from about 98.5:1.5 to about 99.9:0.1. In an embodiment, the weight ratio of the paraffinic oil to the emulsifier may be, for example, from about 99.2:0.8 to about 99.5:0.5. In an embodiment, the weight ratio of the paraffinic oil to the emulsifier may be, for example, about 98.8:1.2. In an embodiment, the weight ratio of the paraffinic oil to the emulsifier may be, for example, about 99.2:0.8. In an embodiment, the weight ratio of the paraffinic oil to the emulsifier may be, for example, about 99.4:0.6. In an embodiment, the weight ratio of the paraffinic oil to the emulsifier may be, for example, about 99.5:0.5. In an embodiment, the weight ratio of the paraffinic oil to the emulsifier may be, for example, about 99.94:0.06. In an embodiment, the weight ratio of the paraffinic oil to the emulsifier may be, for example, about 99.95:0.05. In an embodiment, the weight ratio of the paraffinic oil to the emulsifier may be, for example, about 99.25:0.75.

In selected embodiments, the emulsifier may be present in the concentrate in an amount, for example, from about 0.05 to about 10.0 wt %, or from about 0.5 to about 10.0 wt %, or from about 1.0 to about 10.0 wt %, or from about 0.05 to about 5.0 wt %, or from about 0.5 to about 5.0 wt %, or from about 1.0 to about 5.0 wt %, or from about 0.05 to about 3.0 wt %, or from about 0.5 to about 3.0 wt %, or from about 1.0 to about 3.0 wt %, or about 0.5 wt %, or about 0.75 wt %, or about 0.8 wt %, or about 1.0 wt %, or about 1.5 wt %, or about 2.0 wt %. In alternative embodiments, the emulsifier may be present in the non-aqueous portion of the O/W emulsion in an amount, for example, from about 0.05 to about 10.0 wt %, or from about 0.5 to about 10.0 wt %, or from about 1.0 to about 10.0 wt %, or from about 0.05 to about 5.0 wt %, or from about 0.5 to about 5.0 wt %, or from about 1.0 to about 5.0 wt %, or from about 0.05 to about 3.0 wt %, or from about 0.5 to about 3.0 wt %, or from about 1.0 to about 3.0 wt %, or about 0.5 wt %, or about 0.75 wt %, or about 0.8 wt %, or about 1.0 wt %, or about 1.5 wt %, or about 2.0 wt %. In selected embodiments, the emulsifier may be present in the O/W emulsion in an amount, for example, from about 2.0 wt % of less, or from about 1.0 wt % or less, or from about 0.01 to about 2.0 wt %, or from about 0.025 to about 2.0 wt %, or from about 0.5 to about 2.0 wt %, or from about 0.01 to about 1.0 wt %, or from about 0.025 to about 1.0 wt %, or from about 0.5 to about 1.0 wt %, or from about 0.01 to about 0.5 wt %, or from about 0.025 to about 0.5 wt %, or from about 0.01 to about 0.25 wt %, or from about 0.025 to about 0.25 wt %, or about 0.05 wt %, or about 0.06 wt %, or about 0.1 wt %, or about 0.12 wt %, or about 0.5 wt %, or about 0.6 wt %, or about 1.2 wt %.

In alternative embodiments, the pigment may be, for example, a phthalocyanine compound. In selected embodiments, the pigment may be, for example, a metal-free phthalocyanine compound. In an embodiment, the pigment may be, for example, a halogenated metal-free phthalocyanine. In an embodiment, the pigment may be, for example, a polychlorinated metal-free phthalocyanine. In alternative embodiments, the pigment may be, for example, a metal phthalocyanine compound. In an embodiment, the pigment may be, for example, a copper phthalocyanine. In an embodiment, the pigment may be, for example, a nonhalogenated copper phthalocyanine. In an embodiment, the pigment may be, for example, a nonchlorinated copper phthalocyanine. In an embodiment, the pigment may be, for example, Phthalocyanine Blue BN (CAS 147-14-8). In an embodiment, the pigment may be, for example, a halogenated copper phthalocyanine. In an embodiment, the pigment may be, for example, Phthalocyanine Green 6G (CAS 14302-13-7). In an embodiment, the pigment may be, for example, polychlorinated (Cu II) phthalocyanine. In an embodiment, the pigment may be, for example, Phthalocyanine Green G (CAS 1328-45-6 and 1328-53-6). Non-limiting examples of suitable pigments may include Sunsperse™ Green 7 (available from Sun Chemical Corp. Performance Pigments Cincinnati, Ohio, USA), Sunsperse™ EXP 006-102 (available from Sun Chemical Corp. Performance Pigments, Cincinnati, Ohio, USA), and Pigment Green 7 powder (available from Hercules Exports, Mumbai, India).

In alternative embodiments, the silicone surfactant may comprise, for example, a silicone polyether. In an embodiment, the silicone surfactant may comprise, for example, a silicone polyether having a suitable alkoxy group with hydrogen end groups (H-capped), methyl end groups (CH$_3$-capped), or acetyl end groups (COCH$_3$-capped). In an embodiment, the silicone polyether may be, for example, a trisiloxane having a suitable alkoxy group with hydrogen end groups (H-capped), methyl end groups (CH$_3$-capped), or acetyl end groups (COCH$_3$-capped). In an embodiment, the silicone surfactant may comprise, for example, a silicone polyether of the formula I:

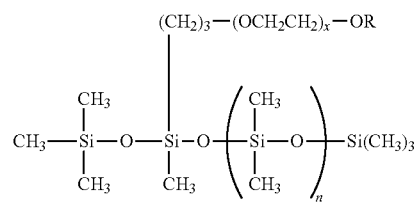

wherein R is H, CH$_3$ or COCH$_3$; x is 1 to 24; and n is 0 or ≥1. In an embodiment, the silicone surfactant may comprise, for example, a silicone polyether of the formula I wherein R=H; x=1 to 24; and n=0. In an embodiment, the silicone surfactant may comprise, for example, a silicone polyether of the formula I wherein R=H; x=1 to 24; and n≥1. In an embodiment, the silicone surfactant may comprise, for example, a silicone polyether of the formula I wherein R=CH$_3$; x=1 to 24; and n=0. In an embodiment, the silicone surfactant may comprise, for example, a silicone polyether of the formula I wherein R=CH$_3$; x=1 to 24; and n≥1. In an embodiment, the silicone surfactant may comprise, for example, a silicone polyether of the formula I wherein R=COCH$_3$; x=1 to 24; and n=0. In an embodiment, the silicone surfactant may comprise, for example, a silicone polyether of the formula I wherein R=COCH$_3$; x=1 to 24; and n≥1.

In selected embodiments, the silicone surfactant may comprise, for example, a silicone polyether of the formula I wherein n=0; x=1-24; the average x=8-10; and R=H. In an embodiment, the silicone surfactant may comprise, for example, a silicone polyether of the formula I wherein n=0; x=1-24, the average x=8-10; and R=COCH$_3$.

In alternative embodiments, the silicone surfactant may comprise, for example, an H-capped dimethyl methyl(polyethylene oxide) silicone polymer. In an embodiment, the H-capped dimethyl methyl(polyethylene oxide) silicone polymer may have, for example, a molecular weight from about 200 to about 6000. In an embodiment, the silicone surfactant may comprise, for example, a silicone polyether of the formula II:

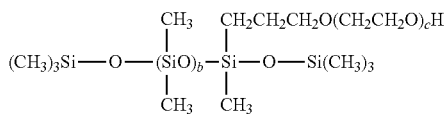

wherein c=2-16; and b=2-70. In an embodiment, for example, the average b=44. In an embodiment, for example, the average c=10.

Alternatively, the silicone surfactant may comprise, for example, an H-capped trisiloxane. In an embodiment, the silicone surfactant may comprise, for example, a silicone polyether of the formula III:

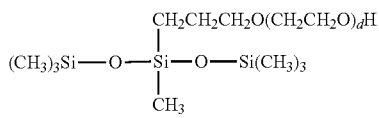

wherein d=1-24. In an embodiment, for example, d=1-20. In an embodiment, for example, the average d=8-10. In an embodiment, for example, the average d=8.

Alternatively, the silicone surfactant may comprise, for example, a silicone copolyol, containing a hydrogen end group and one pendant polyethylene oxide group and has an average molecular weight between about 600 to about 1000 Daltons. In an embodiment, the silicone surfactant may comprise, for example, a trisiloxane with an ethoxylated alkyl group having a hydrogen end group (H-End). In an embodiment, the trisiloxane with an ethoxylated alkyl group having a hydrogen end group may have, for example, a number of ethoxylation groups in the range of 1-20. In an embodiment, the silicone surfactant may comprise, for example, a methyl(propylhydroxide, ethoxylated)bis(trimethylsiloxy) silane. In an embodiment, the silicone surfactant may comprise, for example, a dimethyl, methyl(polyethylene oxide) silicone polymer.

Commercial preparations of the silicone surfactants may or may not contain small amounts of polyethylene glycols (PEG) or other low molecular weight polydimethyl siloxanes (PDMS).

In selected embodiments, the polyethylene glycol may comprise, for example, a polyethylene glycol of the formula IV:

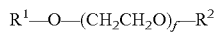

wherein R$^1$=H or CH$_2$=CH—CH$_2$ or COCH$_3$; R$^2$=H or CH$_2$=CH—CH$_2$ or COCH$_3$; and f≥1. In an embodiment, the polyethylene glycol has, for example, a low molecular weight. In an embodiment, the polyethylene glycol has, for example, a molecular weight of about 300 to about 1500 Daltons. In an embodiment, the polyethylene glycol may be, for example, a low molecular weight polyethylene glycol allyl ether. In an embodiment, the polyethylene glycol may be, for example, a low molecular weight polyethylene glycol mono-allyl ether having an average molecular of from about 300 to about 600 Daltons and having from 1 to moles of ethylene glycol with an average ethoxylation (EO) of 8 to 10. In an embodiment, the polyethylene glycol may comprise, for example, a polyethylene glycol of the formula IV wherein R$^1$=CH$_2$=CH—CH$_2$, R$^2$=H, and f=1-20 with an average f=8, a polyethylene glycol of the formula IV wherein R$^1$=CH$_2$=CH—CH$_2$ or COCH$_3$, and R$^2$=COCH$_3$, a polyethylene glycol of the formula IV wherein R$^1$=CH$_2$=CH—CH$_2$, and R$^2$=H, or any combination thereof. In an embodiment, the polyethylene glycol may comprise, for example, a polyethylene glycol of the formula IV wherein R$^1$=CH$_2$=CH—CH$_2$ or COCH$_3$, and R$^2$=COCH$_3$, a polyethylene glycol of the formula IV wherein R$^1$=CH$_2$=CH—CH$_2$, and R$^2$=H, or any combination thereof. In an embodiment, the polyethylene glycol may comprise, for example, a polyethylene glycol of the formula IV wherein R$^1$=CH$_2$=CH—CH$_2$, R$^2$=H, and f=1-20 with an average f=8. In an embodiment, the polyethylene glycol may comprise, for example, a polyethylene glycol of the formula IV wherein R$^1$=CH$_2$=CH—CH$_2$ or COCH$_3$, and R$^2$=COCH$_3$. In an embodiment, the polyethylene glycol may comprise, for example, a polyethylene glycol of the formula IV wherein R$^1$=CH$_2$=CH—CH$_2$, and R$^2$=H. Non-limiting examples of suitable polyethylene glycols may include Polyglykol A500 (available from Clariant).

In alternative embodiments, the silicone surfactant may further comprise, for example, the polyethylene glycol. In selected embodiments, the silicone surfactant may comprise, for example, from about 10 to about 30 wt % of polyethylene glycol. In selected embodiments, the polyethylene glycol may be present in the O/W emulsion in an amount, for example, from about 0.01 to about 0.03 wt %.

Non-limiting examples of suitable silicone surfactants may include Sylgard™ 309 (available from Dow Corning, Midland, Mich., USA), Silfsurf™ A008-UP (available from Siltech Corp. Toronto, ON, Canada), Lambent MFF 199 SW (available from Lambent Technologies Corp., Gurnee, Ill., USA), and Lambent MFF 159-100 (available from Lambent Technologies Corp., Gurnee, Ill., USA).

In selected embodiments, the silicone surfactant may be present in the concentrate in an amount, for example, from about 0.1 to about 5 wt %, or about 1.8 wt %, or about 2 wt %. In alternative embodiments, the silicone surfactant may be present in the non-aqueous portion of the O/W emulsion in an amount, for example, from about 0.1 to about 5 wt %, or about 1.8 wt %, or about 2 wt %. In selected embodiments, the silicone surfactant may be present in the O/W emulsion in an amount, for example, from about 0.01 to about 0.5 wt %, or about 0.1 wt %, or about 0.12 wt %.

In alternative embodiments, boscalid may be used in different crystal forms, and in alternative hydration states, such as an anhydrate or monohydrate (see, for example, WO 03/029219 and WO 04/072039). Boscalid may be commercially available, for example as a product identified as Emerald™ (available from BASF Corporation, Research Triangle Park, N.C., USA).

In alternative embodiments, the aqueous component of the O/W emulsions may comprise distilled water or other waters having a low mineral electrolyte content.

In selected embodiments, the fungicidal compositions may exhibit a synergistic response, for example in controlling a fungal pathogen in turfgrass. In an embodiment, the fungicidal compositions may be synergistic fungicidal compositions for treating a fungal pathogen in turfgrass. In alternative embodiments, the fungicidal composition may exhibit a synergistic response, for example, in controlling dollar spot or dead spot or a combination thereof in turfgrass. In selected embodiments, the fungicidal composition may exhibit a synergistic response, for example, in controlling dollar spot or bentgrass dead spot or bermudagrass dead spot or a combination thereof in turfgrass. In selected embodiments, the fungicidal compositions may exhibit a synergistic response, for example in controlling dollar spot in turfgrass. Accordingly, in an embodiment, the fungicidal compositions may be synergistic fungicidal compositions for treating dollar spot in turfgrass. In selected embodiments, the fungicidal compositions may exhibit a synergistic response, for example in controlling bentgrass dead spot or bermudagrass dead spot in turfgrass. Accordingly, in an embodiment, the fungicidal compositions may be synergistic fungicidal compositions for treating bentgrass dead spot or bermudagrass dead spot or a combination thereof in turfgrass. In alternative embodiments, the fungicidal compositions may be synergistic fungicidal combinations for treating bentgrass dead spot. In selected embodiments, the fungicidal compositions may be synergistic fungicidal composition for treating bermudagrass dead spot in turfgrass. As for example is suggested by Burpee and Latin (Plant Disease Vol. 92 No. 4, April 2008, 601-606), the term "synergy", "synergistic", or the like, may refer to the interaction of two or more agents so that their combined effect is greater than the sum of their individual effects, this may include, in the context of the invention, the action of two or more fungicidal agents in which the total response of a fungus to the fungicidal agent combination is greater than the sum of the individual components.

In selected embodiments, the paraffinic oil may be present in the composition in a synergistically effective amount. In selected embodiments, boscalid may be present in the composition in a synergistically effective amount. In alternative embodiments, the pigment may be present in the composition in a synergistically effective amount. In selected embodiments, the paraffinic oil and boscalid may be present in the composition in synergistically effective amounts. In alternative embodiments, the paraffinic oil and the pigment may be present in the composition in synergistically effective amounts. In selected embodiments, boscalid and the pigment may be present in the composition in synergistically effective amounts. In alternative embodiments, the paraffinic oil, boscalid and the pigment may be present in the composition in synergistically effective amounts. In alternative embodiments, the paraffinic oil may be used or applied to the plant at a rate which supplies a synergistically effective amount of the paraffinic oil to the plant. Similarly, boscalid may be used or applied to the plant at a rate which supplies a synergistically effective amount of boscalid to the plant. Alternatively, the pigment may be used or applied to the plant at a rate which supplies a synergistically effective amount of the pigment to the plant. In selected embodiments, the paraffinic oil and boscalid may be used or applied to the plant at rates which supply synergistically effective amounts of the paraffinic oil and boscalid to the plant. In selected embodiments, the paraffinic oil and the pigment may be used or applied to the plant at rates which supply synergistically effective amounts of the paraffinic oil and the pigment to the plant. In selected embodiments, the boscalid and the pigment may be used or applied to the plant at rates which supply synergistically effective amounts of boscalid and the pigment to the plant. In selected embodiments, the paraffinic oil, boscalid and the pigment may be used or applied to the plant at rates which supply synergistically effective amounts of the paraffinic oil, boscalid and the pigment to the plant.

In alternative embodiments, the paraffinic oil may be used or applied to the plant at a rate that is less than a given rate, such as less than the rate proscribed by product labeling. For example, the paraffinic oil may be used or applied to the plant at, for example, 75% or less of the label rate, or 70% or less of the label rate. Alternatively, the paraffinic oil may be used or applied to the plant at, for example, 50% or less of the label rate, or from about 25% to about 75% of the label rate, or from about 25% to about 50% of the label rate, or at about 75% of the label rate, or at about 50% of the label rate, or at about 25% of the label rate. In selected embodiments, the paraffinic oil may be used or applied to the plant at, for example, from about 0.9 to about 32 oz/1000 square ft, or from about 1 to about 32 oz/1000 square ft, or from about 2 to about 32 oz/1000 square ft, or from about 3 to about 32 oz/1000 square ft, or from about 4 to about 32 oz/1000 square ft, or from about 5 to about 32 oz/1000 square ft, or from about 6 to about 32 oz/1000 square ft, or from about 7 to about 32 oz/1000 square ft, or from about 8 to about 32 oz/1000 square ft, or from about 9 to about 32 oz/1000 square ft, or from about 10 to about 32 oz/1000 square ft, or from about 11 to about 32 oz/1000 square ft, or from about 12 to about 32 oz/1000 square ft, or from about 13 to about 32 oz/1000 square ft, or from about 14 to about 32 oz/1000 square ft, or from about 15 to about 32 oz/1000 square ft, or from about 16 to about 32 oz/1000 square ft, or from about 17 to about 32 oz/1000 square ft, or from about 18 to about 32 oz/1000 square ft, or from about 19 to about 32 oz/1000 square ft, or from about 20 to about 32 oz/1000 square ft, or from about 21 to about 32 oz/1000 square ft, or from about 22 to about 32 oz/1000 square ft, or from about 23 to about 32 oz/1000 square ft, or from about 24 to about 32 oz/1000 square ft, or from about 25 to about 32 oz/1000 square ft, or from about 26 to about 32 oz/1000 square ft, or from about 27 to about 32 oz/1000 square ft, or from about 28 to about 32 oz/1000 square ft, or from about 29 to about 32 oz/1000 square ft, or from about 30 to about 32 oz/1000 square ft, or from about 31 to about 32 oz/1000 square ft, or from about 0.9 to about 31 oz/1000 square ft, or from about 1 to about 31 oz/1000 square ft, or from about 2 to about 31 oz/1000 square ft, or from about 3 to about 31 oz/1000 square ft, or from about 4 to about 31 oz/1000 square ft, or from about 5 to about 31 oz/1000 square ft, or from about 6 to about 31 oz/1000 square ft, or from about 7 to about 31 oz/1000 square ft, or from about 8 to about 31 oz/1000 square ft, or from about 9 to about 31 oz/1000 square ft, or from about 10 to about 31 oz/1000 square ft, or from about 11 to about 31 oz/1000 square ft, or from about 12 to about 31 oz/1000 square ft, or from about 13 to about 31 oz/1000 square ft, or from about 14 to about 31 oz/1000 square ft, or from about 15 to about 31 oz/1000 square ft, or from about 16 to about 31 oz/1000 square ft, or from about 17 to about 31 oz/1000 square ft, or from about 18 to about 31 oz/1000 square ft, or from about 19 to about 31 oz/1000 square ft, or from about 20 to about 31 oz/1000 square ft, or from about 21 to about 31 oz/1000 square ft, or from about 22 to about 31 oz/1000 square ft, or from about 23 to about 31 oz/1000 square ft, or from about 24 to about 31 oz/1000 square ft, or from about 25 to about 31 oz/1000 square ft, or from about 26 to about 31 oz/1000 square ft, or from about 27 to about 31 oz/1000 square ft, or from about 28 to about 31 oz/1000 square ft, or from about 29 to about 31 oz/1000 square ft, or from about 30 to about 31 oz/1000 square ft, or from about 0.9 to about 30 oz/1000 square ft, or from about 1 to about 30 oz/1000 square ft, or from about 2 to about 30 oz/1000 square ft, or from about 3 to about 30 oz/1000 square ft, or from about 4 to about 30 oz/1000 square ft, or from about 5 to about 30 oz/1000 square ft, or from about 6 to about 30 oz/1000 square ft, or from about 7 to about 30 oz/1000 square ft, or from about 8 to about 30 oz/1000 square ft, or from about 9 to about 30 oz/1000 square ft, or from about 10 to about 30 oz/1000 square ft, or from about 11 to about 30 oz/1000 square ft, or from about 12 to about 30 oz/1000 square ft, or from about 13 to about 30 oz/1000 square ft, or from about 14 to about 30 oz/1000 square ft, or from about 15 to about 30 oz/1000 square ft, or from about 16 to about 30 oz/1000 square ft, or from about 17 to about 30 oz/1000 square ft, or from about 18 to about 30 oz/1000 square ft, or from about 19 to about 30 oz/1000 square ft, or from about 20 to about 30 oz/1000 square ft, or from about 21 to about 30 oz/1000 square ft, or from about 22 to about 30 oz/1000 square ft, or from about 23 to about 30 oz/1000 square ft, or from about 24 to about 30 oz/1000 square ft, or from about 25 to about 30 oz/1000 square ft, or from about 26 to about 30 oz/1000 square ft, or from about 27 to about 30 oz/1000 square ft, or from about 28 to about 30 oz/1000 square ft, or from about 29 to about 30 oz/1000 square ft, or from about 0.9 to about 29 oz/1000 square ft, or from about 1 to about 29 oz/1000 square ft, or from about 2 to about 29 oz/1000 square ft, or from about 3 to about 29 oz/1000 square ft, or from about 4 to about 29 oz/1000 square ft, or from about 5 to about 29 oz/1000 square ft, or from about 6 to about 29 oz/1000 square ft, or from about 7 to about 29 oz/1000 square ft, or from about 8 to about 29 oz/1000 square ft, or from about 9 to about 29 oz/1000 square ft, or from about 10 to about 29 oz/1000 square ft, or from about 11 to about 29 oz/1000 square ft, or from about 12 to about 29 oz/1000 square ft, or from about 13 to about 29 oz/1000 square ft, or from about 14 to about 29 oz/1000 square ft, or from about 15 to about 29 oz/1000 square ft, or from about 16 to about 29 oz/1000 square ft, or from about 17 to about 29 oz/1000 square ft, or from about 18 to about 29 oz/1000 square ft, or from about 19 to about 29 oz/1000 square ft, or from about 20 to about 29 oz/1000 square ft, or from about 21 to about 29 oz/1000 square ft, or from about 22 to about 29 oz/1000 square ft, or from about 23 to about 29 oz/1000 square ft, or from about 24 to about 29 oz/1000 square ft, or from about 25 to about 29 oz/1000 square ft, or from about 26 to about 29 oz/1000 square ft, or from about 27 to about 29 oz/1000 square ft, or from about 28 to about 29 oz/1000 square ft, or from about 0.9 to about 28 oz/1000 square ft, or from about 1 to about 28 oz/1000 square ft, or from about 2 to about 28 oz/1000 square ft, or from about 3 to about 28 oz/1000 square ft, or from about 4 to about 28 oz/1000 square ft, or from about 5 to about 28 oz/1000 square ft, or from about 6 to about 28 oz/1000 square ft, or from about 7 to about 28 oz/1000 square ft, or from about 8 to about 28 oz/1000 square ft, or from about 9 to about 28 oz/1000 square ft, or from about 10 to about 28 oz/1000 square ft, or from about 11 to about 28 oz/1000 square ft, or from about 12 to about 28 oz/1000 square ft, or from about 13 to about 28 oz/1000 square ft, or from about 14 to about 28 oz/1000 square ft, or from about 15 to about 28 oz/1000 square ft, or from about 16 to about 28 oz/1000 square ft, or from about 17 to about 28 oz/1000 square ft, or from about 18 to about 28 oz/1000 square ft, or from about 19 to about 28 oz/1000 square ft, or from about 20 to about 28 oz/1000 square ft, or from about 21 to about 28 oz/1000 square ft, or from about 22 to about 28 oz/1000 square ft, or from about 23 to about 28 oz/1000 square ft, or from about 24 to about 28 oz/1000 square ft, or from about 25 to about 28 oz/1000 square ft, or from about 26 to about 28 oz/1000 square ft, or from about 27 to about 28 oz/1000 square ft, or from about 0.9 to about 27 oz/1000 square ft, or from about 1 to about 27 oz/1000 square ft, or from about 2 to about 27 oz/1000 square ft, or from about 3 to about 27 oz/1000 square ft, or from about 4 to about 27 oz/1000 square ft, or from about 5 to about 27 oz/1000 square ft, or from about 6 to about 27 oz/1000 square ft, or from about 7 to about 27 oz/1000 square ft, or from about 8 to about 27 oz/1000 square ft, or from about 9 to about 27 oz/1000 square ft, or from about 10 to about 27 oz/1000 square ft, or from about 11 to about 27 oz/1000 square ft, or from about 12 to about 27 oz/1000 square ft, or from about 13 to about 27 oz/1000 square ft, or from about 14 to about 27 oz/1000 square ft, or from about 15 to about 27 oz/1000 square ft, or from about 16 to about 27 oz/1000 square ft, or from about 17 to about 27 oz/1000 square ft, or from about 18 to about 27 oz/1000 square ft, or from about 19 to about 27 oz/1000 square ft, or from about 20 to about 27 oz/1000 square ft, or from about 21 to about 27 oz/1000 square ft, or from about 22 to about 27 oz/1000 square ft, or from about 23 to about 27 oz/1000 square ft, or from about 24 to about 27 oz/1000 square ft, or from about 25 to about 27 oz/1000 square ft, or from about 26 to about 27 oz/1000 square ft, or from about 0.9 to about 26 oz/1000 square ft, or from about 1 to about 26 oz/1000 square ft, or from about 2 to about 26 oz/1000 square ft, or from about 3 to about 26 oz/1000 square ft, or from about 4 to about 26 oz/1000 square ft, or from about 5 to about 26 oz/1000 square ft, or from about 6 to about 26 oz/1000 square ft, or from about 7 to about 26 oz/1000 square ft, or from about 8 to about 26 oz/1000 square ft, or from about 9 to about 26 oz/1000 square ft, or from about 10 to about 26 oz/1000 square ft, or from about 11 to about 26 oz/1000 square ft, or from about 12 to about 26 oz/1000 square ft, or from about 13 to about 26 oz/1000 square ft, or from about 14 to about 26 oz/1000 square ft, or from about 15 to about 26 oz/1000 square ft, or from about 16 to about 26 oz/1000 square ft, or from about 17 to about 26 oz/1000 square ft, or from about 18 to about 26 oz/1000 square ft, or from about 19 to about 26 oz/1000 square ft, or from about 20 to about 26 oz/1000 square ft, or from about 21 to about 26 oz/1000 square ft, or from about 22 to about 26 oz/1000 square ft, or from about 23 to about 26 oz/1000 square ft, or from about 24 to about 26 oz/1000 square ft, or from about 25 to about 26 oz/1000 square ft, or from about 0.9 to about 25 oz/1000 square ft, or from about 1 to about 25 oz/1000 square ft, or from about 2 to about 25 oz/1000 square ft, or from about 3 to about 25 oz/1000 square ft, or from about 4 to about 25 oz/1000 square ft, or from about 5 to about 25 oz/1000 square ft, or from about 6 to about 25 oz/1000 square ft, or from about 7 to about 25 oz/1000 square ft, or from about 8 to about 25 oz/1000 square ft, or from about 9 to about 25 oz/1000 square ft, or from about 10 to about 25 oz/1000 square ft, or from about 11 to about 25 oz/1000 square ft, or from about 12 to about 25 oz/1000 square ft, or from about 13 to about 25 oz/1000 square ft, or from about 14 to about 25 oz/1000 square ft, or from about 15 to about 25 oz/1000 square ft, or from about 16 to about 25 oz/1000 square ft, or from about 17 to about 25 oz/1000 square ft, or from about 18 to about 25 oz/1000 square ft, or from about 19 to about 25 oz/1000 square ft, or from about 20 to about 25 oz/1000 square ft, or from about 21 to about 25 oz/1000 square ft, or from about 22 to about 25 oz/1000 square ft, or from about 23 to about 25 oz/1000 square ft, or from about 24 to about 25 oz/1000 square ft, or from about 0.9 to about 24 oz/1000 square ft, or from about 1 to about 24 oz/1000 square ft, or from about 2 to about 24 oz/1000 square ft, or from about 3 to about 24 oz/1000 square ft, or from about 4 to about 24 oz/1000 square ft, or from about 5 to about 24 oz/1000 square ft, or from about 6 to about 24 oz/1000 square ft, or from about 7 to about 24 oz/1000 square ft, or from about 8 to about 24 oz/1000 square ft, or from about 9 to about 24 oz/1000 square ft, or from about 10 to about 24 oz/1000 square ft, or from about 11 to about 24 oz/1000 square ft, or from about 12 to about 24 oz/1000 square ft, or from about 13 to about 24 oz/1000 square ft, or from about 14 to about 24 oz/1000 square ft, or from about 15 to about 24 oz/1000 square ft, or from about 16 to about 24 oz/1000 square ft, or from about 17 to about 24 oz/1000 square ft, or from about 18 to about 24 oz/1000 square ft, or from about 19 to about 24 oz/1000 square ft, or from about 20 to about 24 oz/1000 square ft, or from about 21 to about 24 oz/1000 square ft, or from about 22 to about 24 oz/1000 square ft, or from about 23 to about 24 oz/1000 square ft, or from about 0.9 to about 23 oz/1000 square ft, or from about 1 to about 23 oz/1000 square ft, or from about 2 to about 23 oz/1000 square ft, or from about 3 to about 23 oz/1000 square ft, or from about 4 to about 23 oz/1000 square ft, or from about 5 to about 23 oz/1000 square ft, or from about 6 to about 23 oz/1000 square ft, or from about 7 to about 23 oz/1000 square ft, or from about 8 to about 23 oz/1000 square ft, or from about 9 to about 23 oz/1000 square ft, or from about 10 to about 23 oz/1000 square ft, or from about 11 to about 23 oz/1000 square ft, or from about 12 to about 23 oz/1000 square ft, or from about 13 to about 23 oz/1000 square ft, or from about 14 to about 23 oz/1000 square ft, or from about 15 to about 23 oz/1000 square ft, or from about 16 to about 23 oz/1000 square ft, or from about 17 to about 23 oz/1000 square ft, or from about 18 to about 23 oz/1000 square ft, or from about 19 to about 23 oz/1000 square ft, or from about 20 to about 23 oz/1000 square ft, or from about 21 to about 23 oz/1000 square ft, or from about 22 to about 23 oz/1000 square ft, or from about 0.9 to about 22 oz/1000 square ft, or from about 1 to about 22 oz/1000 square ft, or from about 2 to about 22 oz/1000 square ft, or from about 3 to about 22 oz/1000 square ft, or from about 4 to about 22 oz/1000 square ft, or from about 5 to about 22 oz/1000 square ft, or from about 6 to about 22 oz/1000 square ft, or from about 7 to about 22 oz/1000 square ft, or from about 8 to about 22 oz/1000 square ft, or from about 9 to about 22 oz/1000 square ft, or from about 10 to about 22 oz/1000 square ft, or from about 11 to about 22 oz/1000 square ft, or from about 12 to about 22 oz/1000 square ft, or from about 13 to about 22 oz/1000 square ft, or from about 14 to about 22 oz/1000 square ft, or from about 15 to about 22 oz/1000 square ft, or from about 16 to about 22 oz/1000 square ft, or from about 17 to about 22 oz/1000 square ft, or from about 18 to about 22 oz/1000 square ft, or from about 19 to about 22 oz/1000 square ft, or from about 20 to about 22 oz/1000 square ft, or from about 21 to about 22 oz/1000 square ft, or from about 0.9 to about 21 oz/1000 square ft, or from about 1 to about 21 oz/1000 square ft, or from about 2 to about 21 oz/1000 square ft, or from about 3 to about 21 oz/1000 square ft, or from about 4 to about 21 oz/1000 square ft, or from about 5 to about 21 oz/1000 square ft, or from about 6 to about 21 oz/1000 square ft, or from about 7 to about 21 oz/1000 square ft, or from about 8 to about 21 oz/1000 square ft, or from about 9 to about 21 oz/1000 square ft, or from about 10 to about 21 oz/1000 square ft, or from about 11 to about 21 oz/1000 square ft, or from about 12 to about 21 oz/1000 square ft, or from about 13 to about 21 oz/1000 square ft, or from about 14 to about 21 oz/1000 square ft, or from about 15 to about 21 oz/1000 square ft, or from about 16 to about 21 oz/1000 square ft, or from about 17 to about 21 oz/1000 square ft, or from about 18 to about 21 oz/1000 square ft, or from about 19 to about 21 oz/1000 square ft, or from about 20 to about 21 oz/1000 square ft, or from about 0.9 to about 20 oz/1000 square ft, or from about 1 to about 20 oz/1000 square ft, or from about 2 to about 20 oz/1000 square ft, or from about 3 to about 20 oz/1000 square ft, or from about 4 to about 20 oz/1000 square ft, or from about 5 to about 20 oz/1000 square ft, or from about 6 to about 20 oz/1000 square ft, or from about 7 to about 20 oz/1000 square ft, or from about 8 to about 20 oz/1000 square ft, or from about 9 to about 20 oz/1000 square ft, or from about 10 to about 20 oz/1000 square ft, or from about 11 to about 20 oz/1000 square ft, or from about 12 to about 20 oz/1000 square ft, or from about 13 to about 20 oz/1000 square ft, or from about 14 to about 20 oz/1000 square ft, or from about 15 to about 20 oz/1000 square ft, or from about 16 to about 20 oz/1000 square ft, or from about 17 to about 20 oz/1000 square ft, or from about 18 to about 20 oz/1000 square ft, or from about 19 to about 20 oz/1000 square ft, or from about 0.9 to about 19 oz/1000 square ft, or from about 1 to about 19 oz/1000 square ft, or from about 2 to about 19 oz/1000 square ft, or from about 3 to about 19 oz/1000 square ft, or from about 4 to about 19 oz/1000 square ft, or from about 5 to about 19 oz/1000 square ft, or from about 6 to about 19 oz/1000 square ft, or from about 7 to about 19 oz/1000 square ft, or from about 8 to about 19 oz/1000 square ft, or from about 9 to about 19 oz/1000 square ft, or from about 10 to about 19 oz/1000 square ft, or from about 11 to about 19 oz/1000 square ft, or from about 12 to about 19 oz/1000 square ft, or from about 13 to about 19 oz/1000 square ft, or from about 14 to about 19 oz/1000 square ft, or from about 15 to about 19 oz/1000 square ft, or from about 16 to about 19 oz/1000 square ft, or from about 17 to about 19 oz/1000 square ft, or from about 18 to about 19 oz/1000 square ft, or from about 0.9 to about 18 oz/1000 square ft, or from about 1 to about 18 oz/1000 square ft, or from about 2 to about 18 oz/1000 square ft, or from about 3 to about 18 oz/1000 square ft, or from about 4 to about 18 oz/1000 square ft, or from about 5 to about 18 oz/1000 square ft, or from about 6 to about 18 oz/1000 square ft, or from about 7 to about 18 oz/1000 square ft, or from about 8 to about 18 oz/1000 square ft, or from about 9 to about 18 oz/1000 square ft, or from about 10 to about 18 oz/1000 square ft, or from about 11 to about 18 oz/1000 square ft, or from about 12 to about 18 oz/1000 square ft, or from about 13 to about 18 oz/1000 square ft, or from about 14 to about 18 oz/1000 square ft, or from about 15 to about 18 oz/1000 square ft, or from about 16 to about 18 oz/1000 square ft, or from about 17 to about 18 oz/1000 square ft, or from about 0.9 to about 17 oz/1000 square ft, or from about 1 to about 17 oz/1000 square ft, or from about 2 to about 17 oz/1000 square ft, or from about 3 to about 17 oz/1000 square ft, or from about 4 to about 17 oz/1000 square ft, or from about 5 to about 17 oz/1000 square ft, or from about 6 to about 17 oz/1000 square ft, or from about 7 to about 17 oz/1000 square ft, or from about 8 to about 17 oz/1000 square ft, or from about 9 to about 17 oz/1000 square ft, or from about 10 to about 17 oz/1000 square ft, or from about 11 to about 17 oz/1000 square ft, or from about 12 to about 17 oz/1000 square ft, or from about 13 to about 17 oz/1000 square ft, or from about 14 to about 17 oz/1000 square ft, or from about 15 to about 17 oz/1000 square ft, or from about 16 to about 17 oz/1000 square ft, or from about 0.9 to about 16 oz/1000 square ft, or from about 1 to about 16 oz/1000 square ft, or from about 2 to about 16 oz/1000 square ft, or from about 3 to about 16 oz/1000 square ft, or from about 4 to about 16 oz/1000 square ft, or from about 5 to about 16 oz/1000 square ft, or from about 6 to about 16 oz/1000 square ft, or from about 7 to about 16 oz/1000 square ft, or from about 8 to about 16 oz/1000 square ft, or from about 9 to about 16 oz/1000 square ft, or from about 10 to about 16 oz/1000 square ft, or from about 11 to about 16 oz/1000 square ft, or from about 12 to about 16 oz/1000 square ft, or from about 13 to about 16 oz/1000 square ft, or from about 14 to about 16 oz/1000 square ft, or from about 15 to about 16 oz/1000 square ft, or from about 0.9 to about 15 oz/1000 square ft, or from about 1 to about 15 oz/1000 square ft, or from about 2 to about 15 oz/1000 square ft, or from about 3 to about 15 oz/1000 square ft, or from about 4 to about 15 oz/1000 square ft, or from about 5 to about 15 oz/1000 square ft, or from about 6 to about 15 oz/1000 square ft, or from about 7 to about 15 oz/1000 square ft, or from about 8 to about 15 oz/1000 square ft, or from about 9 to about 15 oz/1000 square ft, or from about 10 to about 15 oz/1000 square ft, or from about 11 to about 15 oz/1000 square ft, or from about 12 to about 15 oz/1000 square ft, or from about 13 to about 15 oz/1000 square ft, or from about 14 to about 15 oz/1000 square ft, or from about 0.9 to about 14 oz/1000 square ft, or from about 1 to about 14 oz/1000 square ft, or from about 2 to about 14 oz/1000 square ft, or from about 3 to about 14 oz/1000 square ft, or from about 4 to about 14 oz/1000 square ft, or from about 5 to about 14 oz/1000 square ft, or from about 6 to about 14 oz/1000 square ft, or from about 7 to about 14 oz/1000 square ft, or from about 8 to about 14 oz/1000 square ft, or from about 9 to about 14 oz/1000 square ft, or from about 10 to about 14 oz/1000 square ft, or from about 11 to about 14 oz/1000 square ft, or from about 12 to about 14 oz/1000 square ft, or from about 13 to about 14 oz/1000 square ft, or from about 0.9 to about 13 oz/1000 square ft, or from about 1 to about 13 oz/1000 square ft, or from about 2 to about 13 oz/1000 square ft, or from about 3 to about 13 oz/1000 square ft, or from about 4 to about 13 oz/1000 square ft, or from about 5 to about 13 oz/1000 square ft, or from about 6 to about 13 oz/1000 square ft, or from about 7 to about 13 oz/1000 square ft, or from about 8 to about 13 oz/1000 square ft, or from about 9 to about 13 oz/1000 square ft, or from about 10 to about 13 oz/1000 square ft, or from about 11 to about 13 oz/1000 square ft, or from about 12 to about 13 oz/1000 square ft, or from about 0.9 to about 12 oz/1000 square ft, or from about 1 to about 12 oz/1000 square ft, or from about 2 to about 12 oz/1000 square ft, or from about 3 to about 12 oz/1000 square ft, or from about 4 to about 12 oz/1000 square ft, or from about 5 to about 12 oz/1000 square ft, or from about 6 to about 12 oz/1000 square ft, or from about 7 to about 12 oz/1000 square ft, or from about 8 to about 12 oz/1000 square ft, or from about 9 to about 12 oz/1000 square ft, or from about 10 to about 12 oz/1000 square ft, or from about 11 to about 12 oz/1000 square ft, or from about 0.9 to about 11 oz/1000 square ft, or from about 1 to about 11 oz/1000 square ft, or from about 2 to about 11 oz/1000 square ft, or from about 3 to about 11 oz/1000 square ft, or from about 4 to about 11 oz/1000 square ft, or from about 5 to about 11 oz/1000 square ft, or from about 6 to about 11 oz/1000 square ft, or from about 7 to about 11 oz/1000 square ft, or from about 8 to about 11 oz/1000 square ft, or from about 9 to about 11 oz/1000 square ft, or from about 10 to about 11 oz/1000 square ft, or from about 0.9 to about 10 oz/1000 square ft, or from about 1 to about 10 oz/1000 square ft, or from about 2 to about 10 oz/1000 square ft, or from about 3 to about 10 oz/1000 square ft, or from about 4 to about 10 oz/1000 square ft, or from about 5 to about 10 oz/1000 square ft, or from about 6 to about 10 oz/1000 square ft, or from about 7 to about 10 oz/1000 square ft, or from about 8 to about 10 oz/1000 square ft, or from about 9 to about 10 oz/1000 square ft, or from about 0.9 to about 9 oz/1000 square ft, or from about 1 to about 9 oz/1000 square ft, or from about 2 to about 9 oz/1000 square ft, or from about 3 to about 9 oz/1000 square ft, or from about 4 to about 9 oz/1000 square ft, or from about 5 to about 9 oz/1000 square ft, or from about 6 to about 9 oz/1000 square ft, or from about 7 to about 9 oz/1000 square ft, or from about 8 to about 9 oz/1000 square ft, or from about 0.9 to about 8 oz/1000 square ft, or from about 1 to about 8 oz/1000 square ft, or from about 2 to about 8 oz/1000 square ft, or from about 3 to about 8 oz/1000 square ft, or from about 4 to about 8 oz/1000 square ft, or from about 5 to about 8 oz/1000 square ft, or from about 6 to about 8 oz/1000 square ft, or from about 7 to about 8 oz/1000 square ft, or from about 0.9 to about 7 oz/1000 square ft, or from about 1 to about 7 oz/1000 square ft, or from about 2 to about 7 oz/1000 square ft, or from about 3 to about 7 oz/1000 square ft, or from about 4 to about 7 oz/1000 square ft, or from about 5 to about 7 oz/1000 square ft, or from about 6 to about 7 oz/1000 square ft, or from about 0.9 to about 6 oz/1000 square ft, or from about 1 to about 6 oz/1000 square ft, or from about 2 to about 6 oz/1000 square ft, or from about 3 to about 6 oz/1000 square ft, or from about 4 to about 6 oz/1000 square ft, or from about 5 to about 6 oz/1000 square ft, or from about 0.9 to about 5 oz/1000 square ft, or from about 1 to about 5 oz/1000 square ft, or from about 2 to about 5 oz/1000 square ft, or from about 3 to about 5 oz/1000 square ft, or from about 4 to about 5 oz/1000 square ft, or from about 0.9 to about 4 oz/1000 square ft, or from about 1 to about 4 oz/1000 square ft, or from about 2 to about 4 oz/1000 square ft, or from about 3 to about 4 oz/1000 square ft, or from about 0.9 to about 3 oz/1000 square ft, or from about 1 to about 3 oz/1000 square ft, or from about 2 to about 3 oz/1000 square ft, or from about 0.9 to about 2 oz/1000 square ft, or from about 1 to about 2 oz/1000 square ft, or from about 0.9 to about 1 oz/1000 square ft. In selected embodiments, the paraffinic oil may be used or applied to the plant at, for example, about 0.9 oz/1000 square ft, or about 1 oz/1000 square ft, or about 2 oz/1000 square ft, or about 3 oz/1000 square ft, or about 4 oz/1000 square ft, or about 5 oz/1000 square ft, or about 6 oz/1000 square ft, or about 7 oz/1000 square ft, or about 8 oz/1000 square ft, or about 9 oz/1000 square ft, or about 10 oz/1000 square ft, or about 11 oz/1000 square ft, or about 12 oz/1000 square ft, or about 13 oz/1000 square ft, or about 14 oz/1000 square ft, or about 15 oz/1000 square ft, or about 16 oz/1000 square ft, or about 17 oz/1000 square ft, or about 18 oz/1000 square ft, or about 19 oz/1000 square ft, or about 20 oz/1000 square ft, or about 21 oz/1000 square ft, or about 22 oz/1000 square ft, or about 23 oz/1000 square ft, or about 24 oz/1000 square ft, or about 25 oz/1000 square ft, or about 26 oz/1000 square ft, or about 27 oz/1000 square ft, or about 28 oz/1000 square ft, or about 29 oz/1000 square ft, or about 30 oz/1000 square ft, or about 31 oz/1000 square ft, or about 32 oz/1000 square ft. In alternative embodiments, the paraffinic oil may be used or applied to the plant at, for example, about 7.8 oz/1000 square ft, or about 15.7 oz/1000 square ft, or about 12.5 oz/1000 square ft.

In selected embodiments, the paraffinic oil may be used or applied to the plant at an interval rate of, for example, from 1 day to 90 days, or from 1 day to 60 days, or from 1 day to 30 days, or from 1 day to 21 days, or from 1 day to 14 days, or from 1 day to 7 days, or from 7 days to 90 days, or from 7 days to 60 days, or from 7 days to 30 days, or from 7 days to 21 days, or from 7 days to 14 days, from 14 days to 90 days, from 14 days to 60 days, from 14 days to 30 days, or from 14 days to 21 days, or 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 31 days, or 32 days, or 33 days, or 34 days, or 35 days, or 36 days, or 37 days, or 38 days, or 39 days, or 40 days, or 41 days, or 42 days, or 43 days, or 44 days, or 45 days, or 46 days, or 47 days, or 48 days, or 49 days, or 50 days, or 51 days, or 52 days, or 53 days, or 54 days, or 55 days, or 56 days, or 57 days, or 58 days, or 59 days, or 60 days, or 61 days, or 62 days, or 63 days, or 64 days, or 65 days, or 66 days, or 67 days, or 68 days, or 69 days, or 70 days, or 71 days, or 72 days, or 73 days, or 74 days, or 75 days, or 76 days, or 77 days, or 78 days, or 79 days, or 80 days, or 81 days, or 82 days, or 83 days, or 84 days, or 85 days, or 86 days, or 87 days, or 88 days, or 89 days, or 90 days.

In selected embodiments, boscalid may be used or applied to the plant at a rate that is less than a given rate, such as less than the rate proscribed by product labeling. In alternative embodiments, boscalid may be used or applied to the plant at, for example, 75% or less of the label rate, or 70% or less of the label rate, or 50% or less of the label rate, or from about 25% to about 75% of the label rate, or from about 25% to about 50% of the label rate, or at about 75% of the label rate, or at about 50% of the label rate, or at about 25% of the label rate. In selected embodiments, boscalid may be used or applied to the plant at, for example, from about 0.01 to about 0.18 oz/1000 square ft, or from about 0.02 to about 0.18 oz/1000 square ft, or from about 0.03 to about 0.18 oz/1000 square ft, or from about 0.04 to about 0.18 oz/1000 square ft, or from about 0.05 to about 0.18 oz/1000 square ft, or from about 0.06 to about 0.18 oz/1000 square ft, or from about 0.07 to about 0.18 oz/1000 square ft, or from about 0.08 to about 0.18 oz/1000 square ft, or from about 0.09 to about 0.18 oz/1000 square ft, or from about 0.10 to about 0.18 oz/1000 square ft, or from about 0.11 to about 0.18 oz/1000 square ft, or from about 0.12 to about 0.18 oz/1000 square ft, or from about 0.13 to about 0.18 oz/1000 square ft, or from about 0.14 to about 0.18 oz/1000 square ft, or from about 0.15 to about 0.18 oz/1000 square ft, or from about 0.16 to about 0.18 oz/1000 square ft, or from about 0.17 to about 0.18 oz/1000 square ft, or from about 0.01 to about 0.17 oz/1000 square ft, or from about 0.02 to about 0.17 oz/1000 square ft, or from about 0.03 to about 0.17 oz/1000 square ft, or from about 0.04 to about 0.17 oz/1000 square ft, or from about 0.05 to about 0.17 oz/1000 square ft, or from about 0.06 to about 0.17 oz/1000 square ft, or from about 0.07 to about 0.17 oz/1000 square ft, or from about 0.08 to about 0.17 oz/1000 square ft, or from about 0.09 to about 0.17 oz/1000 square ft, or from about 0.10 to about 0.17 oz/1000 square ft, or from about 0.11 to about 0.17 oz/1000 square ft, or from about 0.12 to about 0.17 oz/1000 square ft, or from about 0.13 to about 0.17 oz/1000 square ft, or from about 0.14 to about 0.17 oz/1000 square ft, or from about 0.15 to about 0.17 oz/1000 square ft, or from about 0.16 to about 0.17 oz/1000 square ft, or from about 0.01 to about 0.16 oz/1000 square ft, or from about 0.02 to about 0.16 oz/1000 square ft, or from about 0.03 to about 0.16 oz/1000 square ft, or from about 0.04 to about 0.16 oz/1000 square ft, or from about 0.05 to about 0.16 oz/1000 square ft, or from about 0.06 to about 0.16 oz/1000 square ft, or from about 0.07 to about 0.16 oz/1000 square ft, or from about 0.08 to about 0.16 oz/1000 square ft, or from about 0.09 to about 0.16 oz/1000 square ft, or from about 0.10 to about 0.16 oz/1000 square ft, or from about 0.11 to about 0.16 oz/1000 square ft, or from about 0.12 to about 0.16 oz/1000 square ft, or from about 0.13 to about 0.16 oz/1000 square ft, or from about 0.14 to about 0.16 oz/1000 square ft, or from about 0.15 to about 0.16 oz/1000 square ft, or from about 0.01 to about 0.15 oz/1000 square ft, or from about 0.02 to about 0.15 oz/1000 square ft, or from about 0.03 to about 0.15 oz/1000 square ft, or from about 0.04 to about 0.15 oz/1000 square ft, or from about 0.05 to about 0.15 oz/1000 square ft, or from about 0.06 to about 0.15 oz/1000 square ft, or from about 0.07 to about 0.15 oz/1000 square ft, or from about 0.08 to about 0.15 oz/1000 square ft, or from about 0.09 to about 0.15 oz/1000 square ft, or from about 0.10 to about 0.15 oz/1000 square ft, or from about 0.11 to about 0.15 oz/1000 square ft, or from about 0.12 to about 0.15 oz/1000 square ft, or from about 0.13 to about 0.15 oz/1000 square ft, or from about 0.14 to about 0.15 oz/1000 square ft, or from about 0.01 to about 0.14 oz/1000 square ft, or from about 0.02 to about 0.14 oz/1000 square ft, or from about 0.03 to about 0.14 oz/1000 square ft, or from about 0.04 to about 0.14 oz/1000 square ft, or from about 0.05 to about 0.14 oz/1000 square ft, or from about 0.06 to about 0.14 oz/1000 square ft, or from about 0.07 to about 0.14 oz/1000 square ft, or from about 0.08 to about 0.14 oz/1000 square ft, or from about 0.09 to about 0.14 oz/1000 square ft, or from about 0.10 to about 0.14 oz/1000 square ft, or from about 0.11 to about 0.14 oz/1000 square ft, or from about 0.12 to about 0.14 oz/1000 square ft, or from about 0.13 to about 0.14 oz/1000 square ft, or from about 0.01 to about 0.13 oz/1000 square ft, or from about 0.02 to about 0.13 oz/1000 square ft, or from about 0.03 to about 0.13 oz/1000 square ft, or from about 0.04 to about 0.13 oz/1000 square ft, or from about 0.05 to about 0.13 oz/1000 square ft, or from about 0.06 to about 0.13 oz/1000 square ft, or from about 0.07 to about 0.13 oz/1000 square ft, or from about 0.08 to about 0.13 oz/1000 square ft, or from about 0.09 to about 0.13 oz/1000 square ft, or from about 0.10 to about 0.13 oz/1000 square ft, or from about 0.11 to about 0.13 oz/1000 square ft, or from about 0.12 to about 0.13 oz/1000 square ft, or from about 0.01 to about 0.12 oz/1000 square ft, or from about 0.02 to about 0.12 oz/1000 square ft, or from about 0.03 to about 0.12 oz/1000 square ft, or from about 0.04 to about 0.12 oz/1000 square ft, or from about 0.05 to about 0.12 oz/1000 square ft, or from about 0.06 to about 0.12 oz/1000 square ft, or from about 0.07 to about 0.12 oz/1000 square ft, or from about 0.08 to about 0.12 oz/1000 square ft, or from about 0.09 to about 0.12 oz/1000 square ft, or from about 0.10 to about 0.12 oz/1000 square ft, or from about 0.11 to about 0.12 oz/1000 square ft, or from about 0.01 to about 0.11 oz/1000 square ft, or from about 0.02 to about 0.11 oz/1000 square ft, or from about 0.03 to about 0.11 oz/1000 square ft, or from about 0.04 to about 0.11 oz/1000 square ft, or from about 0.05 to about 0.11 oz/1000 square ft, or from about 0.06 to about 0.11 oz/1000 square ft, or from about 0.07 to about 0.11 oz/1000 square ft, or from about 0.08 to about 0.11 oz/1000 square ft, or from about 0.09 to about 0.11 oz/1000 square ft, or from about 0.10 to about 0.11 oz/1000 square ft, or from about 0.01 to about 0.10 oz/1000 square ft, or from about 0.02 to about 0.10 oz/1000 square ft, or from about 0.03 to about 0.10 oz/1000 square ft, or from about 0.04 to about 0.10 oz/1000 square ft, or from about 0.05 to about 0.10 oz/1000 square ft, or from about 0.06 to about 0.10 oz/1000 square ft, or from about 0.07 to about 0.10 oz/1000 square ft, or from about 0.08 to about 0.10 oz/1000 square ft, or from about 0.09 to about 0.10 oz/1000 square ft, or from about 0.01 to about 0.09 oz/1000 square ft, or from about 0.02 to about 0.09 oz/1000 square ft, or from about 0.03 to about 0.09 oz/1000 square ft, or from about 0.04 to about 0.09 oz/1000 square ft, or from about 0.05 to about 0.09 oz/1000 square ft, or from about 0.06 to about 0.09 oz/1000 square ft, or from about 0.07 to about 0.09 oz/1000 square ft, or from about 0.08 to about 0.09 oz/1000 square ft, or from about 0.01 to about 0.08 oz/1000 square ft, or from about 0.02 to about 0.08 oz/1000 square ft, or from about 0.03 to about 0.08 oz/1000 square ft, or from about 0.04 to about 0.08 oz/1000 square ft, or from about 0.05 to about 0.08 oz/1000 square ft, or from about 0.06 to about 0.08 oz/1000 square ft, or from about 0.07 to about 0.08 oz/1000 square ft, or from about 0.01 to about 0.07 oz/1000 square ft, or from about 0.02 to about 0.07 oz/1000 square ft, or from about 0.03 to about 0.07 oz/1000 square ft, or from about 0.04 to about 0.07 oz/1000 square ft, or from about 0.05 to about 0.07 oz/1000 square ft, or from about 0.06 to about 0.07 oz/1000 square ft, or from about 0.01 to about 0.06 oz/1000 square ft, or from about 0.02 to about 0.06 oz/1000 square ft, or from about 0.03 to about 0.06 oz/1000 square ft, or from about 0.04 to about 0.06 oz/1000 square ft, or from about 0.05 to about 0.06 oz/1000 square ft, or from about 0.01 to about 0.05 oz/1000 square ft, or from about 0.02 to about 0.05 oz/1000 square ft, or from about 0.03 to about 0.05 oz/1000 square ft, or from about 0.04 to about 0.05 oz/1000 square ft, or from about 0.01 to about 0.04 oz/1000 square ft, or from about 0.02 to about 0.04 oz/1000 square ft, or from about 0.03 to about 0.04 oz/1000 square ft, or from about 0.01 to about 0.03 oz/1000 square ft, or from about 0.02 to about 0.03 oz/1000 square ft, or from about 0.01 to about 0.02 oz/1000 square ft. In selected embodiments, boscalid may be used or applied to the plant at, for example, about 0.01 oz/1000 square ft, or about 0.02 oz/1000 square ft, or about 0.03 oz/1000 square ft, or about 0.04 oz/1000 square ft, or about 0.05 oz/1000 square ft, or about 0.06 oz/1000 square ft, or about 0.07 oz/1000 square ft, or about 0.08 oz/1000 square ft, or about 0.09 oz/1000 square ft, or about 0.10 oz/1000 square ft, or about 0.11 oz/1000 square ft, or about 0.12 oz/1000 square ft, or about 0.13 oz/1000 square ft, or about 0.14 oz/1000 square ft, or about 0.15 oz/1000 square ft, or about 0.16 oz/1000 square ft, or about 0.17 oz/1000 square ft, or about 0.18 oz/1000. In alternative embodiments, boscalid may be used or applied to the plant at, for example, about 0.09 oz/1000 square ft, or about 0.045 oz/1000 square ft.

In selected embodiments, boscalid may be used or applied to the plant at an interval rate of, for example, from 1 day to 90 days, or from 1 day to 60 days, or from 1 day to 30 days, or from 1 day to 21 days, or from 1 day to 14 days, or from 1 day to 7 days, or from 7 days to 90 days, or from 7 days to 60 days, or from 7 days to 30 days, or from 7 days to 21 days, or from 7 days to 14 days, from 14 days to 90 days, from 14 days to 60 days, from 14 days to 30 days, or from 14 days to 21 days, or 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 31 days, or 32 days, or 33 days, or 34 days, or 35 days, or 36 days, or 37 days, or 38 days, or 39 days, or 40 days, or 41 days, or 42 days, or 43 days, or 44 days, or 45 days, or 46 days, or 47 days, or 48 days, or 49 days, or 50 days, or 51 days, or 52 days, or 53 days, or 54 days, or 55 days, or 56 days, or 57 days, or 58 days, or 59 days, or 60 days, or 61 days, or 62 days, or 63 days, or 64 days, or 65 days, or 66 days, or 67 days, or 68 days, or 69 days, or 70 days, or 71 days, or 72 days, or 73 days, or 74 days, or 75 days, or 76 days, or 77 days, or 78 days, or 79 days, or 80 days, or 81 days, or 82 days, or 83 days, or 84 days, or 85 days, or 86 days, or 87 days, or 88 days, or 89 days, or 90 days.

In alternative embodiments, the paraffinic oil and boscalid may be present in the fungicidal composition in a weight ratio of boscalid:paraffinic oil that is synergistically effective. In selected embodiments, the paraffinic oil and boscalid may be used or applied to the plant in a weight ratio of boscalid:paraffinic oil that is synergistically effective. In selected embodiments, the paraffinic oil and boscalid may be used or applied to the plant in a weight ratio of boscalid:paraffinic oil of, for example, from about 0.12:3 to about 0.12:32, or from about 0.12:4 to about 0.12:32, or about 0.12:3, or about 0.12:4, or about 0.12:5, or about 0.12:6, or about 0.12:7, or about 0.12:8, or about 0.12:9, or about 0.12:10, or about 0.12:11, or about 0.12:12, or about 0.12:13, or about 0.12:14, or about 0.12:15, or about 0.12:16, or about 0.12:17, or about 0.12:18, or about 0.12:19, or about 0.12:20, or about 0.12:21, or about 0.12:22, or about 0.12:23, or about 0.12:24, or about 0.12:25, or about 0.12:26, or about 0.12:27, or about 0.12:28, or about 0.12:29, or about 0.12:30, or about 0.12:31, or about 0.12:32. In alternative embodiments, the paraffinic oil and boscalid may be used or applied to the plant in a weight ratio of boscalid:paraffinic oil of, for example, from about 0.02:1 to about 0.02:32, or from about 0.02:2 to about 0.02:32, or about 0.02:1, or about 0.02:2, or about 0.02:3, or about 0.02:4, or about 0.02:5, or about 0.02:6, or about 0.02:7, or about 0.02:8, or about 0.02:9, or about 0.02:10, or about 0.02:11, or about 0.02:12, or about 0.02:13, or about 0.02:14, or about 0.02:15, or about 0.02:16, or about 0.02:17, or about 0.02:18, or about 0.02:19, or about 0.02:20, or about 0.02:21, or about 0.02:22, or about 0.02:23, or about 0.02:24, or about 0.02:25, or about 0.02:26, or about 0.02:27, or about 0.02:28, or about 0.02:29, or about 0.02:30, or about 0.02:31, or about 0.02:32.

In selected embodiments, the pigment may be used or applied to the plant at, for example, from about 0.1 to about 3.0 oz/1000 square ft, or from about 0.2 to about 3.0 oz/1000 square ft, or from about 0.3 to about 3.0 oz/1000 square ft, or from about 0.4 to about 3.0 oz/1000 square ft, or from about 0.5 to about 3.0 oz/1000 square ft, or from about 0.6 to about 3.0 oz/1000 square ft, or from about 0.7 to about 3.0 oz/1000 square ft, or from about 0.8 to about 3.0 oz/1000 square ft, or from about 0.9 to about 3.0 oz/1000 square ft, or from about 1.0 to about 3.0 oz/1000 square ft, or from about 1.2 to about 3.0 oz/1000 square ft, or from about 1.4 to about 3.0 oz/1000 square ft, or from about 1.6 to about 3.0 oz/1000 square ft, or from about 1.8 to about 3.0 oz/1000 square ft, or from about 2.0 to about 3.0 oz/1000 square ft, or from about 2.2 to about 3.0 oz/1000 square ft, or from about 2.4 to about 3.0 oz/1000 square ft, or from about 2.6 to about 3.0 oz/1000 square ft, or from about 2.8 to about 3.0 oz/1000 square ft, or from about 0.1 to about 2.8 oz/1000 square ft, or from about 0.2 to about 2.8 oz/1000 square ft, or from about 0.3 to about 2.8 oz/1000 square ft, or from about 0.4 to about 2.8 oz/1000 square ft, or from about 0.5 to about 2.8 oz/1000 square ft, or from about 0.6 to about 2.8 oz/1000 square ft, or from about 0.7 to about 2.8 oz/1000 square ft, or from about 0.8 to about 2.8 oz/1000 square ft, or from about 0.9 to about 2.8 oz/1000 square ft, or from about 1.0 to about 2.8 oz/1000 square ft, or from about 1.2 to about 2.8 oz/1000 square ft, or from about 1.4 to about 2.8 oz/1000 square ft, or from about 1.6 to about 2.8 oz/1000 square ft, or from about 1.8 to about 2.8 oz/1000 square ft, or from about 2.0 to about 2.8 oz/1000 square ft, or from about 2.2 to about 2.8 oz/1000 square ft, or from about 2.4 to about 2.8 oz/1000 square ft, or from about 2.6 to about 2.8 oz/1000 square ft, or from about 0.1 to about 2.6 oz/1000 square ft, or from about 0.2 to about 2.6 oz/1000 square ft, or from about 0.3 to about 2.6 oz/1000 square ft, or from about 0.4 to about 2.6 oz/1000 square ft, or from about 0.5 to about 2.6 oz/1000 square ft, or from about 0.6 to about 2.6 oz/1000 square ft, or from about 0.7 to about 2.6 oz/1000 square ft, or from about 0.8 to about 2.6 oz/1000 square ft, or from about 0.9 to about 2.6 oz/1000 square ft, or from about 1.0 to about 2.6 oz/1000 square ft, or from about 1.2 to about 2.6 oz/1000 square ft, or from about 1.4 to about 2.6 oz/1000 square ft, or from about 1.6 to about 2.6 oz/1000 square ft, or from about 1.8 to about 2.6 oz/1000 square ft, or from about 2.0 to about 2.6 oz/1000 square ft, or from about 2.2 to about 2.6 oz/1000 square ft, or from about 2.4 to about 2.6 oz/1000 square ft, or from about 0.1 to about 2.4 oz/1000 square ft, or from about 0.2 to about 2.4 oz/1000 square ft, or from about 0.3 to about 2.4 oz/1000 square ft, or from about 0.4 to about 2.4 oz/1000 square ft, or from about 0.5 to about 2.4 oz/1000 square ft, or from about 0.6 to about 2.4 oz/1000 square ft, or from about 0.7 to about 2.4 oz/1000 square ft, or from about 0.8 to about 2.4 oz/1000 square ft, or from about 0.9 to about 2.4 oz/1000 square ft, or from about 1.0 to about 2.4 oz/1000 square ft, or from about 1.2 to about 2.4 oz/1000 square ft, or from about 1.4 to about 2.4 oz/1000 square ft, or from about 1.6 to about 2.4 oz/1000 square ft, or from about 1.8 to about 2.4 oz/1000 square ft, or from about 2.0 to about 2.4 oz/1000 square ft, or from about 2.2 to about 2.4 oz/1000 square ft, or from about 0.1 to about 2.2 oz/1000 square ft, or from about 0.2 to about 2.2 oz/1000 square ft, or from about 0.3 to about 2.2 oz/1000 square ft, or from about 0.4 to about 2.2 oz/1000 square ft, or from about 0.5 to about 2.2 oz/1000 square ft, or from about 0.6 to about 2.2 oz/1000 square ft, or from about 0.7 to about 2.2 oz/1000 square ft, or from about 0.8 to about 2.2 oz/1000 square ft, or from about 0.9 to about 2.2 oz/1000 square ft, or from about 1.0 to about 2.2 oz/1000 square ft, or from about 1.2 to about 2.2 oz/1000 square ft, or from about 1.4 to about 2.2 oz/1000 square ft, or from about 1.6 to about 2.2 oz/1000 square ft, or from about 1.8 to about 2.2 oz/1000 square ft, or from about 2.0 to about 2.2 oz/1000 square ft, or from about 0.1 to about 2.0 oz/1000 square ft, or from about 0.2 to about 2.0 oz/1000 square ft, or from about 0.3 to about 2.0 oz/1000 square ft, or from about 0.4 to about 2.0 oz/1000 square ft, or from about 0.5 to about 2.0 oz/1000 square ft, or from about 0.6 to about 2.0 oz/1000 square ft, or from about 0.7 to about 2.0 oz/1000 square ft, or from about 0.8 to about 2.0 oz/1000 square ft, or from about 0.9 to about 2.0 oz/1000 square ft, or from about 1.0 to about 2.0 oz/1000 square ft, or from about 1.2 to about 2.0 oz/1000 square ft, or from about 1.4 to about 2.0 oz/1000 square ft, or from about 1.6 to about 2.0 oz/1000 square ft, or from about 1.8 to about 2.0 oz/1000 square ft, or from about 0.1 to about 1.8 oz/1000 square ft, or from about 0.2 to about 1.8 oz/1000 square ft, or from about 0.3 to about 1.8 oz/1000 square ft, or from about 0.4 to about 1.8 oz/1000 square ft, or from about 0.5 to about 1.8 oz/1000 square ft, or from about 0.6 to about 1.8 oz/1000 square ft, or from about 0.7 to about 1.8 oz/1000 square ft, or from about 0.8 to about 1.8 oz/1000 square ft, or from about 0.9 to about 1.8 oz/1000 square ft, or from about 1.0 to about 1.8 oz/1000 square ft, or from about 1.2 to about 1.8 oz/1000 square ft, or from about 1.4 to about 1.8 oz/1000 square ft, or from about 1.6 to about 1.8 oz/1000 square ft, or from about 0.1 to about 1.6 oz/1000 square ft, or from about 0.2 to about 1.6 oz/1000 square ft, or from about 0.3 to about 1.6 oz/1000 square ft, or from about 0.4 to about 1.6 oz/1000 square ft, or from about 0.5 to about 1.6 oz/1000 square ft, or from about 0.6 to about 1.6 oz/1000 square ft, or from about 0.7 to about 1.6 oz/1000 square ft, or from about 0.8 to about 1.6 oz/1000 square ft, or from about 0.9 to about 1.6 oz/1000 square ft, or from about 1.0 to about 1.6 oz/1000 square ft, or from about 1.2 to about 1.6 oz/1000 square ft, or from about 1.4 to about 1.6 oz/1000 square ft, or from about 0.1 to about 1.4 oz/1000 square ft, or from about 0.2 to about 1.4 oz/1000 square ft, or from about 0.3 to about 1.4 oz/1000 square ft, or from about 0.4 to about 1.4 oz/1000 square ft, or from about 0.5 to about 1.4 oz/1000 square ft, or from about 0.6 to about 1.4 oz/1000 square ft, or from about 0.7 to about 1.4 oz/1000 square ft, or from about 0.8 to about 1.4 oz/1000 square ft, or from about 0.9 to about 1.4 oz/1000 square ft, or from about 1.0 to about 1.4 oz/1000 square ft, or from about 1.2 to about 1.4 oz/1000 square ft, or from about 0.1 to about 1.2 oz/1000 square ft, or from about 0.2 to about 1.2 oz/1000 square ft, or from about 0.3 to about 1.2 oz/1000 square ft, or from about 0.4 to about 1.2 oz/1000 square ft, or from about 0.5 to about 1.2 oz/1000 square ft, or from about 0.6 to about 1.2 oz/1000 square ft, or from about 0.7 to about 1.2 oz/1000 square ft, or from about 0.8 to about 1.2 oz/1000 square ft, or from about 0.9 to about 1.2 oz/1000 square ft, or from about 1.0 to about 1.2 oz/1000 square ft, or from about 0.1 to about 1.0 oz/1000 square ft, or from about 0.2 to about 1.0 oz/1000 square ft, or from about 0.3 to about 1.0 oz/1000 square ft, or from about 0.4 to about 1.0 oz/1000 square ft, or from about 0.5 to about 1.0 oz/1000 square ft, or from about 0.6 to about 1.0 oz/1000 square ft, or from about 0.7 to about 1.0 oz/1000 square ft, or from about 0.8 to about 1.0 oz/1000 square ft, or from about 0.9 to about 1.0 oz/1000 square ft, or from about 0.1 to about 0.9 oz/1000 square ft, or from about 0.2 to about 0.9 oz/1000 square ft, or from about 0.3 to about 0.9 oz/1000 square ft, or from about 0.4 to about 0.9 oz/1000 square ft, or from about 0.5 to about 0.9 oz/1000 square ft, or from about 0.6 to about 0.9 oz/1000 square ft, or from about 0.7 to about 0.9 oz/1000 square ft, or from about 0.8 to about 0.9 oz/1000 square ft, or from about 0.1 to about 0.8 oz/1000 square ft, or from about 0.2 to about 0.8 oz/1000 square ft, or from about 0.3 to about 0.8 oz/1000 square ft, or from about 0.4 to about 0.8 oz/1000 square ft, or from about 0.5 to about 0.8 oz/1000 square ft, or from about 0.6 to about 0.8 oz/1000 square ft, or from about 0.7 to about 0.8 oz/1000 square ft, or from about 0.1 to about 0.7 oz/1000 square ft, or from about 0.2 to about 0.7 oz/1000 square ft, or from about 0.3 to about 0.7 oz/1000 square ft, or from about 0.4 to about 0.7 oz/1000 square ft, or from about 0.5 to about 0.7 oz/1000 square ft, or from about 0.6 to about 0.7 oz/1000 square ft, or from about 0.1 to about 0.6 oz/1000 square ft, or from about 0.2 to about 0.6 oz/1000 square ft, or from about 0.3 to about 0.6 oz/1000 square ft, or from about 0.4 to about 0.6 oz/1000 square ft, or from about 0.5 to about 0.6 oz/1000 square ft, or from about 0.1 to about 0.5 oz/1000 square ft, or from about 0.2 to about 0.5 oz/1000 square ft, or from about 0.3 to about 0.5 oz/1000 square ft, or from about 0.4 to about 0.5 oz/1000 square ft, or from about 0.1 to about 0.4 oz/1000 square ft, or from about 0.2 to about 0.4 oz/1000 square ft, or from about 0.3 to about 0.4 oz/1000 square ft, or from about 0.1 to about 0.3 oz/1000 square ft, or from about 0.2 to about 0.3 oz/1000 square ft, or from about 0.1 to about 0.2 oz/1000 square ft, or about 0.1 oz/1000 square ft, or about 0.2 oz/1000 square ft, or about 0.3 oz/1000 square ft, or about 0.4 oz/1000 square ft, or about 0.5 oz/1000 square ft, or about 0.6 oz/1000 square ft, or about 0.7 oz/1000 square ft, or about 0.8 oz/1000 square ft, or about 0.9 oz/1000 square ft, or about 1.0 oz/1000 square ft, or about 1.1 oz/1000 square ft, or about 1.2 oz/1000 square ft, or about 1.3 oz/1000 square ft, or about 1.4 oz/1000 square ft, or about 1.5 oz/1000 square ft, or about 1.6 oz/1000 square ft, or about 1.7 oz/1000 square ft, or about 1.8 oz/1000 square ft, or about 1.9 oz/1000 square ft, or about 2.0 oz/1000 square ft, or about 2.1 oz/1000 square ft, or about 2.2 oz/1000 square ft, or about 2.3 oz/1000 square ft, or about 2.4 oz/1000 square ft, or about 2.5 oz/1000 square ft, or about 2.6 oz/1000 square ft, or about 2.7 oz/1000 square ft, or about 2.8 oz/1000 square ft, or about 2.9 oz/1000 square ft, or about 3.0 oz/1000 square ft.

In selected embodiments, the pigment may be used or applied to the plant at an interval rate of, for example, from 1 day to 90 days, or from 1 day to 60 days, or from 1 day to 30 days, or from 1 day to 21 days, or from 1 day to 14 days, or from 1 day to 7 days, or from 7 days to 90 days, or from 7 days to 60 days, or from 7 days to 30 days, or from 7 days to 21 days, or from 7 days to 14 days, from 14 days to 90 days, from 14 days to 60 days, from 14 days to 30 days, or from 14 days to 21 days, or 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 31 days, or 32 days, or 33 days, or 34 days, or 35 days, or 36 days, or 37 days, or 38 days, or 39 days, or 40 days, or 41 days, or 42 days, or 43 days, or 44 days, or 45 days, or 46 days, or 47 days, or 48 days, or 49 days, or 50 days, or 51 days, or 52 days, or 53 days, or 54 days, or 55 days, or 56 days, or 57 days, or 58 days, or 59 days, or 60 days, or 61 days, or 62 days, or 63 days, or 64 days, or 65 days, or 66 days, or 67 days, or 68 days, or 69 days, or 70 days, or 71 days, or 72 days, or 73 days, or 74 days, or 75 days, or 76 days, or 77 days, or 78 days, or 79 days, or 80 days, or 81 days, or 82 days, or 83 days, or 84 days, or 85 days, or 86 days, or 87 days, or 88 days, or 89 days, or 90 days.

In alternative embodiments, the paraffinic oil and the pigment may be present in the fungicidal composition in a weight ratio of paraffinic oil:pigment that is synergistically effective. In selected embodiments, the paraffinic oil and the pigment may be present in a weight ratio of paraffinic oil:pigment of, for example, about 10:1, or about 10.5:1, or about 11:1, or about 11.5:1, or about 12:1, or about 12.5:1, or about 13:1, or about 13.5:1, or about 14:1, or about 14.5:1, or about 15:1, or about 15.5:1, or about 16:1, or about 16.5:1, or about 17:1, or about 17.5:1, or about 18:1, or about 18.5:1, or about 19:1, or about 19.5:1, or about 20:1, or about 20.5:1, or about 21:1, or about 21.5:1, or about 22:1. In selected embodiments, the paraffinic oil and the pigment may be used or applied to the plant in a weight ratio of paraffinic oil:pigment that is synergistically effective. In selected embodiments, the paraffinic oil and the pigment may be used or applied to the plant in a weight ratio of paraffinic oil:pigment of, for example, about 10:1, or about 10.5:1, or about 11:1, or about 11.5:1, or about 12:1, or about 12.5:1, or about 13:1, or about 13.5:1, or about 14:1, or about 14.5:1, or about 15:1, or about 15.5:1, or about 16:1, or about 16.5:1, or about 17:1, or about 17.5:1, or about 18:1, or about 18.5:1, or about 19:1, or about 19.5:1, or about 20:1, or about 20.5:1, or about 21:1, or about 21.5:1, or about 22:1.

In selected embodiments, the composition may be applied to the plant at a total spray volume of from about 0.2 to about 7.0 gallons/1000 square ft, or from about 0.4 to about 7.0 gallons/1000 square ft, or from about 0.8 to about 7.0 gallons/1000 square ft, or from about 1.2 to about 7.0 gallons/1000 square ft, or from about 1.6 to about 7.0 gallons/1000 square ft, or from about 2.0 to about 7.0 gallons/1000 square ft, or from about 2.4 to about 7.0 gallons/1000 square ft, or from about 2.8 to about 7.0 gallons/1000 square ft, or from about 3.0 to about 7.0 gallons/1000 square ft, or from about 3.2 to about 7.0 gallons/1000 square ft, or from about 3.6 to about 7.0 gallons/1000 square ft, or from about 4.0 to about 7.0 gallons/1000 square ft, or from about 4.4 to about 7.0 gallons/1000 square ft, or from about 4.8 to about 7.0 gallons/1000 square ft, or from about 5.0 to about 7.0 gallons/1000 square ft, or from about 5.2 to about 7.0 gallons/1000 square ft, or from about 5.6 to about 7.0 gallons/1000 square ft, or from about 6.0 to about 7.0 gallons/1000 square ft, or from about 6.4 to about 7.0 gallons/1000 square ft, or from about 6.8 to about 7.0 gallons/1000 square ft, or from about 0.2 to about 6.8 gallons/1000 square ft, or from about 0.4 to about 6.8 gallons/1000 square ft, or from about 0.8 to about 6.8 gallons/1000 square ft, or from about 1.2 to about 6.8 gallons/1000 square ft, or from about 1.6 to about 6.8 gallons/1000 square ft, or from about 2.0 to about 6.8 gallons/1000 square ft, or from about 2.4 to about 6.8 gallons/1000 square ft, or from about 2.8 to about 6.8 gallons/1000 square ft, or from about 3.0 to about 6.8 gallons/1000 square ft, or from about 3.2 to about 6.8 gallons/1000 square ft, or from about 3.6 to about 6.8 gallons/1000 square ft, or from about 4.0 to about 6.8 gallons/1000 square ft, or from about 4.4 to about 6.8 gallons/1000 square ft, or from about 4.8 to about 6.8 gallons/1000 square ft, or from about 5.0 to about 6.8 gallons/1000 square ft, or from about 5.2 to about 6.8 gallons/1000 square ft, or from about 5.6 to about 6.8 gallons/1000 square ft, or from about 6.0 to about 6.8 gallons/1000 square ft, or from about 6.4 to about 6.8 gallons/1000 square ft, or from about 0.2 to about 6.4 gallons/1000 square ft, or from about 0.4 to about 6.4 gallons/1000 square ft, or from about 0.8 to about 6.4 gallons/1000 square ft, or from about 1.2 to about 6.4 gallons/1000 square ft, or from about 1.6 to about 6.4 gallons/1000 square ft, or from about 2.0 to about 6.4 gallons/1000 square ft, or from about 2.4 to about 6.4 gallons/1000 square ft, or from about 2.8 to about 6.4 gallons/1000 square ft, or from about 3.0 to about 6.4 gallons/1000 square ft, or from about 3.2 to about 6.4 gallons/1000 square ft, or from about 3.6 to about 6.4 gallons/1000 square ft, or from about 4.0 to about 6.4 gallons/1000 square ft, or from about 4.4 to about 6.4 gallons/1000 square ft, or from about 4.8 to about 6.4 gallons/1000 square ft, or from about 5.0 to about 6.4 gallons/1000 square ft, or from about 5.2 to about 6.4 gallons/1000 square ft, or from about 5.6 to about 6.4 gallons/1000 square ft, or from about 6.0 to about 6.4 gallons/1000 square ft, or from about 0.2 to about 6.0 gallons/1000 square ft, or from about 0.4 to about 6.0 gallons/1000 square ft, or from about 0.8 to about 6.0 gallons/1000 square ft, or from about 1.2 to about 6.0 gallons/1000 square ft, or from about 1.6 to about 6.0
gallons/1000 square ft, or from about 2.0 to about 6.0
gallons/1000 square ft, or from about 2.4 to about 6.0
gallons/1000 square ft, or from about 2.8 to about 6.0
gallons/1000 square ft, or from about 3.0 to about 6.0
gallons/1000 square ft, or from about 3.2 to about 6.0
gallons/1000 square ft, or from about 3.6 to about 6.0
gallons/1000 square ft, or from about 4.0 to about 6.0
gallons/1000 square ft, or from about 4.4 to about 6.0
gallons/1000 square ft, or from about 4.8 to about 6.0
gallons/1000 square ft, or from about 5.0 to about 6.0
gallons/1000 square ft, or from about 5.2 to about 6.0
gallons/1000 square ft, or from about 5.6 to about 6.0
gallons/1000 square ft, or from about 0.2 to about 5.6
gallons/1000 square ft, or from about 0.4 to about 5.6
gallons/1000 square ft, or from about 0.8 to about 5.6
gallons/1000 square ft, or from about 1.2 to about 5.6
gallons/1000 square ft, or from about 1.6 to about 5.6
gallons/1000 square ft, or from about 2.0 to about 5.6
gallons/1000 square ft, or from about 2.4 to about 5.6
gallons/1000 square ft, or from about 2.8 to about 5.6
gallons/1000 square ft, or from about 3.0 to about 5.6
gallons/1000 square ft, or from about 3.2 to about 5.6
gallons/1000 square ft, or from about 3.6 to about 5.6
gallons/1000 square ft, or from about 4.0 to about 5.6
gallons/1000 square ft, or from about 4.4 to about 5.6
gallons/1000 square ft, or from about 4.8 to about 5.6
gallons/1000 square ft, or from about 5.0 to about 5.6
gallons/1000 square ft, or from about 5.2 to about 5.6
gallons/1000 square ft, or from about 0.2 to about 5.2
gallons/1000 square ft, or from about 0.4 to about 5.2
gallons/1000 square ft, or from about 0.8 to about 5.2
gallons/1000 square ft, or from about 1.2 to about 5.2
gallons/1000 square ft, or from about 1.6 to about 5.2
gallons/1000 square ft, or from about 2.0 to about 5.2
gallons/1000 square ft, or from about 2.4 to about 5.2
gallons/1000 square ft, or from about 2.8 to about 5.2
gallons/1000 square ft, or from about 3.0 to about 5.2
gallons/1000 square ft, or from about 3.2 to about 5.2
gallons/1000 square ft, or from about 3.6 to about 5.2
gallons/1000 square ft, or from about 4.0 to about 5.2
gallons/1000 square ft, or from about 4.4 to about 5.2
gallons/1000 square ft, or from about 4.8 to about 5.2
gallons/1000 square ft, or from about 5.0 to about 5.2
gallons/1000 square ft, or from about 0.2 to about 5.0
gallons/1000 square ft, or from about 0.4 to about 5.0
gallons/1000 square ft, or from about 0.8 to about 5.0
gallons/1000 square ft, or from about 1.2 to about 5.0
gallons/1000 square ft, or from about 1.6 to about 5.0
gallons/1000 square ft, or from about 2.0 to about 5.0
gallons/1000 square ft, or from about 2.4 to about 5.0
gallons/1000 square ft, or from about 2.8 to about 5.0
gallons/1000 square ft, or from about 3.0 to about 5.0
gallons/1000 square ft, or from about 3.2 to about 5.0
gallons/1000 square ft, or from about 3.6 to about 5.0
gallons/1000 square ft, or from about 4.0 to about 5.0
gallons/1000 square ft, or from about 4.4 to about 5.0
gallons/1000 square ft, or from about 4.8 to about 5.0
gallons/1000 square ft, or from about 0.2 to about 4.8
gallons/1000 square ft, or from about 0.4 to about 4.8
gallons/1000 square ft, or from about 0.8 to about 4.8
gallons/1000 square ft, or from about 1.2 to about 4.8
gallons/1000 square ft, or from about 1.6 to about 4.8
gallons/1000 square ft, or from about 2.0 to about 4.8
gallons/1000 square ft, or from about 2.4 to about 4.8
gallons/1000 square ft, or from about 2.8 to about 4.8
gallons/1000 square ft, or from about 3.0 to about 4.8
gallons/1000 square ft, or from about 3.2 to about 4.8
gallons/1000 square ft, or from about 3.6 to about 4.8
gallons/1000 square ft, or from about 4.0 to about 4.8
gallons/1000 square ft, or from about 4.4 to about 4.8
gallons/1000 square ft, or from about 0.2 to about 4.4
gallons/1000 square ft, or from about 0.4 to about 4.4
gallons/1000 square ft, or from about 0.8 to about 4.4
gallons/1000 square ft, or from about 1.2 to about 4.4
gallons/1000 square ft, or from about 1.6 to about 4.4
gallons/1000 square ft, or from about 2.0 to about 4.4
gallons/1000 square ft, or from about 2.4 to about 4.4
gallons/1000 square ft, or from about 2.8 to about 4.4
gallons/1000 square ft, or from about 3.0 to about 4.4
gallons/1000 square ft, or from about 3.2 to about 4.4
gallons/1000 square ft, or from about 3.6 to about 4.4
gallons/1000 square ft, or from about 4.0 to about 4.4
gallons/1000 square ft, or from about 0.2 to about 4.0
gallons/1000 square ft, or from about 0.4 to about 4.0
gallons/1000 square ft, or from about 0.8 to about 4.0
gallons/1000 square ft, or from about 1.2 to about 4.0
gallons/1000 square ft, or from about 1.6 to about 4.0
gallons/1000 square ft, or from about 2.0 to about 4.0
gallons/1000 square ft, or from about 2.4 to about 4.0
gallons/1000 square ft, or from about 2.8 to about 4.0
gallons/1000 square ft, or from about 3.0 to about 4.0
gallons/1000 square ft, or from about 3.2 to about 4.0
gallons/1000 square ft, or from about 3.6 to about 4.0
gallons/1000 square ft, or from about 0.2 to about 3.6
gallons/1000 square ft, or from about 0.4 to about 3.6
gallons/1000 square ft, or from about 0.8 to about 3.6
gallons/1000 square ft, or from about 1.2 to about 3.6
gallons/1000 square ft, or from about 1.6 to about 3.6
gallons/1000 square ft, or from about 2.0 to about 3.6
gallons/1000 square ft, or from about 2.4 to about 3.6
gallons/1000 square ft, or from about 2.8 to about 3.6
gallons/1000 square ft, or from about 3.0 to about 3.6
gallons/1000 square ft, or from about 3.2 to about 3.6
gallons/1000 square ft, or from about 0.2 to about 3.2
gallons/1000 square ft, or from about 0.4 to about 3.2
gallons/1000 square ft, or from about 0.8 to about 3.2
gallons/1000 square ft, or from about 1.2 to about 3.2
gallons/1000 square ft, or from about 1.6 to about 3.2
gallons/1000 square ft, or from about 2.0 to about 3.2
gallons/1000 square ft, or from about 2.4 to about 3.2
gallons/1000 square ft, or from about 2.8 to about 3.2
gallons/1000 square ft, or from about 3.0 to about 3.2
gallons/1000 square ft, or from about 0.2 to about 3.0
gallons/1000 square ft, or from about 0.4 to about 3.0
gallons/1000 square ft, or from about 0.8 to about 3.0
gallons/1000 square ft, or from about 1.2 to about 3.0
gallons/1000 square ft, or from about 1.6 to about 3.0
gallons/1000 square ft, or from about 2.0 to about 3.0
gallons/1000 square ft, or from about 2.4 to about 3.0
gallons/1000 square ft, or from about 2.8 to about 3.0
gallons/1000 square ft, or from about 0.2 to about 2.8
gallons/1000 square ft, or from about 0.4 to about 2.8
gallons/1000 square ft, or from about 0.8 to about 2.8
gallons/1000 square ft, or from about 1.2 to about 2.8
gallons/1000 square ft, or from about 1.6 to about 2.8
gallons/1000 square ft, or from about 2.0 to about 2.8
gallons/1000 square ft, or from about 2.4 to about 2.8
gallons/1000 square ft, or from about 0.2 to about 2.4
gallons/1000 square ft, or from about 0.4 to about 2.4
gallons/1000 square ft, or from about 0.8 to about 2.4
gallons/1000 square ft, or from about 1.2 to about 2.4
gallons/1000 square ft, or from about 1.6 to about 2.4
gallons/1000 square ft, or from about 2.0 to about 2.4 gallons/1000 square ft, or from about 0.2 to about 2.0 gallons/1000 square ft, or from about 0.4 to about 2.0 gallons/1000 square ft, or from about 0.8 to about 2.0 gallons/1000 square ft, or from about 1.2 to about 2.0 gallons/1000 square ft, or from about 1.6 to about 2.0 gallons/1000 square ft, or from about 0.2 to about 1.6 gallons/1000 square ft, or from about 0.4 to about 1.6 gallons/1000 square ft, or from about 0.8 to about 1.6 gallons/1000 square ft, or from about 1.2 to about 1.6 gallons/1000 square ft, or from about 0.2 to about 1.2 gallons/1000 square ft, or from about 0.4 to about 1.2 gallons/1000 square ft, or from about 0.8 to about 1.2 gallons/1000 square ft, or from about 0.2 to about 0.8 gallons/1000 square ft, or from about 0.4 to about 0.8 gallons/1000 square ft, or from about 0.2 to about 0.4 gallons/1000 square ft, or about 0.2 gallons/1000 square ft, or about 0.4 gallons/1000 square ft, or about 0.8 gallons/1000 square ft, or about 1.0 gallons/1000 square ft, or about 1.2 gallons/1000 square ft, or about 1.6 gallons/1000 square ft, or about 2.0 gallons/1000 square ft, or about 2.4 gallons/1000 square ft, or about 2.8 gallons/1000 square ft, or about 3.0 gallons/1000 square ft, or about 3.2 gallons/1000 square ft, or about 3.6 gallons/1000 square ft, or about 4.0 gallons/1000 square ft, or about 4.4 gallons/1000 square ft, or about 4.8 gallons/1000 square ft, or about 5.0 gallons/1000 square ft, or about 5.2 gallons/1000 square ft, or about 5.6 gallons/1000 square ft, or about 6.0 gallons/1000 square ft, or about 6.4 gallons/1000 square ft, or about 6.8 gallons/1000 square ft, or about 7.0 gallons/1000 square ft.

The composition may also include, for example, customary additives or adjuvants for the preparation of composition in the field of turf or field crop protection. The composition may comprise, for example, a surfactant, a dispersant, a wetter, a thickener, an organic solvent, a cosolvent, an antifoam, a carboxylic acid, a preservative, a stabilizer and the like.

As used herein, the term "control" or "controlling" is used to refer to preventing, destroying, repelling, mitigating or treating plant diseases, such as diseases caused by turfgrass pathogens. In selected embodiments, the plant disease may be caused by, for example, a fungal pathogen. In alternative embodiments, the fungal pathogen may be, for example, a fungus that blights leaf tissue in a turfgrass. In alternative embodiments, the fungal pathogen may be, for example, *Sclerotinia homoeocarpa* or *Ophiosphaerella agrostis* or a combination thereof. In selected embodiments, the disease may be, for example, dollar spot or bentgrass dead spot or bermudagrass dead spot or a combination thereof. In selected embodiments, the turfgass pathogen is the fungal pathogen *Sclerotinia homoeocarpa*, and the disease may be, for example, dollar spot. In alternative embodiments, the turfgrass pathogen is the fungal pathogen *Ophiosphaerella agrostis*, and the disease may be, for example, bentgrass dead spot or bermudagrass dead spot. In alternative embodiments, the turfgrass pathogen is the fungal pathogen *Ophiosphaerella agrostis*, and the disease may be, for example, bentgrass dead spot. In alternative embodiments, the turfgrass pathogen is the fungal pathogen *Ophiosphaerella agrostis*, and the disease may be, for example, bermudagrass dead spot.

As used herein, the term "turfgrass" refers to a cultivated grass that provides groundcover, for example a turf or lawn that is periodically cut or mowed to maintain a consistent height. Grasses belong to the Poaceae family, which is subdivided into six subfamilies, three of which include common turfgrasses: the Festucoideae subfamily of cool-season turfgrasses; and the Panicoideae and Eragrostoideae subfamilies of warm-season turfgrasses. A limited number of species are in widespread use as turfgrasses, generally meeting the criteria of forming uniform soil coverage and tolerating mowing and traffic. In general, turfgrasses have a compressed crown that facilitates mowing without cutting off the growing point. In the context of the present invention, the term "turfgrass" includes areas in which one or more grass species are cultivated to form relatively uniform soil coverage, including blends that are a combination of differing cultivars of the same species, or mixtures that are a combination of differing species and/or cultivars. For example, turfgrasses may include one or more of the following grasses: bluegrasses (*Poa* spp.), such as kentucky bluegrass (*Poa pratensis*), rough bluegrass (*Poa trivialis*), Canada bluegrass (*Poa compressa*), annual bluegrass (*Poa annua*), upland bluegrass (*Poa glaucantha*), wood bluegrass (*Poa nemoralis*), bulbous bluegrass (*Poa bulbosa*), Big Bluegrass (*Poa ampla*), Canby Bluegrass (*Poa canbyi*), Pine Bluegrass (*Poa scabrella*), Rough Bluegrass (*Poa trivialis*), Sandberg Bluegrass (*Poa secunda*); the bentgrasses and Redtop (*Agrostis* spp.), such as creeping bentgrass (*Agrostis palustris*), colonial bentgrass (*Agrostis capillaris*), velvet bentgrass (*Agrostis canina*), South German Mixed Bentgrass (*Agrostis* spp. including *Agrostis tenius*, *Agrostis canina*, and *Agrostis palustris*), Redtop (*Agrostis alba*), Spike Bentgrass (*Agrostis exerata*); the fescues (*Festucu* spp.), such as red *fescue* (*Festuca rubra* spp. *rubra*) creeping *fescue* (*Festuca rubra*), chewings *fescue* (*Festuca rubra commutata*), sheep *fescue* (*Festuca ovina* var. *ovina*), hard *fescue* (*Festuca longifolia*), hair *fescue* (*Festucu capillata*), tall *fescue* (*Festuca arundinacea*), meadow *fescue* (*Festuca elatior*), Arizona *Fescue* (*Festuca arizonica*), Foxtail *Fescue* (*Festuca megalura*), Idaho *Fescue* (*Festuca idahoensis*), Molate *Fescue* (*Fescue rubra*); the ryegrasses (*Lolium* spp.), such as annual ryegrass (*Lolium multiflorum*), perennial ryegrass (*Lolium perenne*), and italian ryegrass (*Lolium multiflorum*); the wheatgrasses (*Agropyron* spp.), such as crested wheatgrass (*Agropyron cristatum*), desert wheatgrass (*Agropyron desertorum*), western wheatgrass (*Agropyron smithii*), Intermediate Wheatgrass (*Agropyron intermedium*), Pubescent Wheatgrass (*Agropyron trichophorum*), Slender Wheatgrass (*Agropyron trachycaulum*), Streambank Wheatgrass (*Agropyron riparium*), Tall Wheatgrass (*Agropyron elongatum*), and Bluebunch Wheatgrass (*Agropyron spicatum*); beachgrass (*Ammophila breviligulata*); Brome grasses (*Bromus* spp.), such as Arizona Brome (*Bromus arizonicus*), California Brome (*Bromus carinatus*), Meadow Brome (*Bromus biebersteinii*), Mountain Brome (*Bromus marginatus*), Red Brome (*Bromus rubens*), and smooth bromegrass (*Bromus inermis*); cattails such as Timothy (*Phleum pratense*), and sand cattail (*Phleum subulatum*); orchardgrass (*Dactylis glomerata*); Alkaligrass (*Puccinellia distans*); crested dog's-tail (*Cynosurus cristatus*); Bermudagrass (*Cynodon* spp. such as *Cynodon dactylon*); hybrid bermudagrass (such as *Cynodon dactylon*×*C. transvaalensis*); Zoysiagrasses (*Zoysia* spp.) such as *Zoysia japonica*, *Zoysia matrella*, and *Zoysia tenuifolia*; St. Augustinegrass (*Stenotaphrum secundatum*); Centipedegrass (*Eremochloa ophiuroides*); Carpetgrass (*Axonopus fissifolius*); Bahiagrass (*Paspalum notatum*); Kikuyugrass (*Pennisetum clandestinum*); Buffalograss (*Buchloe dactyloids*); Seashore paspalum (*Paspalum vaginatum*); Blue Grama (*Bouteloua gracilis*); Black Grama (*Bouteloua eriopoda*); Sideoats Grama (*Bouteloua curtipendula*); *Sporobolus* spp., such as Alkali Sacaton (*Sporobolus airiodes*), Sand Dropseed (*Sporobolus cryptandrus*), and Prairie Dropseed (*Sporobolus heterolepis*); *Hordeum* spp., such as California Barley (*Hordeum* californicum), Common Barley (Hordeum vulgare), and Meadow Barley (Hordeum brachyantherum); Alopecurus spp., such as Creeping Foxtail (Alopecurus arundinaceus), and Meadow Foxtail (Alopecurus pratensis); Stipa spp., such as Needle & Thread (Stipa comata), Foothill Needlegrass (Stipa lepida), Green Needlegrass (Stipa viridula), Nodding Needlegrass (Stipa cernua), and Purple Needlegrass (Stipa pulchra); Elymus spp., such as Blue Wildrye (Elymus glaucus), Canada Wildrye (Elymus Canadensis), Creeping Wildrye (Elymus triticoides), and Russian Wildrye (Elymus junceus); Buffelgrass (Cenchrus ciliaris); Big Quaking Grass (Briza maxima); Big Bluestem (Andropogon gerardii), Little Bluestem (Schizachyruim scoparium, and Sand Bluestem (Andropogon hallii); Deergrass (Muhlenbergia rigens); Eastern Gamagrass (Tripsacum dactyloides); Galleta (Hilaria jamesii); Galleta (Hilaria jamesii); Tufted Hairgrass (Deschampsia caespitosa); Indian Rice Grass (Oryzopsis hymenoides); Indian Grass (Sorghastrum nutans); Sand Lovegrass (Eragrostis trichodes); Weeping Lovegrass (Eragrostis curvula); California Melic (Melica californica); Prairie Junegrass (Koeleria pyramidata); Prairie Sandreed (Calamovilfa longifolia); Redtop (Agrostis alba); Reed Canarygrass (Phalaris arundinacea); Sloughgrass (Spartina pectinata); Green Sprangletop (Leptochloa dubia); Bottlebush Squirreltail (Sitanion hystrix); Panicum Switchgrass (virgatum); and Purple Threeawn (Aristida purpurea).

In selected embodiments, the turfgrass may be, for example, bentgrass, bluegrass, ryegrass, fescue, bermudagrass, paspalum or bahiagrass, zoysia, beachgrass, wheatgrass, carpetgrass, or any combinations thereof. In an embodiment, the turfgrass may be, for example, creeping bentgrass, colonial bentgrass, perennial ryegrass, annual ryegrass, Kentucky bluegrass, common bermudagrass, hybrid bermudagrass, annual bluegrass, seashore paspalum, St. Augustinegrass, tall fescue, bahiagrass, zoysiagrass, centipedegrass, rough stalk bluegrass, buffalo grass, blue grama, annual bentgrass, redtop, velvet bentgrass, coastal bermudagrass, magennis bermudagrass, blue couch grass, smooth crabgrass, sheep fescue, hard fescue, red fescue, chewing fescue, common velvet grass, Italian ryegrass, Texas bluegrass, plains bluegrass, seaside alkali-grass, muscarene grass, or any combinations thereof. In an embodiment, the turfgrass may be, for example, bentgrass, bermudagrass, hybrid bermudagrass, or any combinations thereof. In an embodiment, the turfgrass may be, for example, bentgrass. In another embodiment, the turfgrass may be, for example, bermudagrass or hybrid bermudagrass or a combination thereof. In an embodiment, the turfgrass may be, for example, creeping bentgrass, colonial bentgrass, velvet bentgrass, roughstalk bluegrass, hybrid bermudagrass, or any combinations thereof. In an embodiment, the turfgrass may be, for example, creeping bentgrass, annual bluegrass, or any combinations thereof. In an embodiment, the turfgrass may be, for example, creeping bentgrass. In an embodiment, the turfgrass may be, for example, annual bluegrass. The term turfgrass encompasses areas having differing intensities of cultivation, such as parks, golf courses, sports fields, sod farms, roadsides, and lawns for housing residences, commercial sites, and institutional grounds. A selected embodiment involves the control of dollar spot on annual bluegrass or creeping bentgrass or a combination thereof, particularly on golf courses. A selected embodiment involves control of bentgrass dead spot or bermudagrass dead spot on bentgrass or hybrid bermudagrass or a combination thereof, particularly on golf courses, for example, on golf course greens.

The present invention includes isomers such as geometrical isomers, optical isomers based on asymmetric carbon, stereoisomers and tautomers and is not limited by the description of the formula illustrated for the sake of convenience.

Various alternative embodiments and examples of the invention are described herein. These embodiments and examples are illustrative, and not limiting.

EXAMPLES

General Methodologies

Studies were established in a completely randomized design with three replications. The treatments included an untreated (fertilizer only) treatment and twenty-three rate/interval combinations of Civitas™ and Emerald™. The label-recommended rates of Civitas™ application to control dollar spot on turfgrass are 8-32 oz/1000 sq.ft. The label-recommended rate of Emerald™ application to control dollar spot on turfgrass is 0.13 oz/1000 sq.ft.

Initial treatments were made on June 16 and continued for 15 weeks (final treatments were made on September 27). Treatments were applied to experimental plots (4'×4') on a mixed stand of creeping bentgrass/annual bluegrass (Agrostis palustris/Poa annua) grown on a sand-based putting green (pH=8.2). Applications were made with a handheld $CO_2$ sprayer at 40 psi (276 kPa) fitted with TeeJet™ XR8015 nozzles calibrated to deliver 2 gallons (7.6 liters) of water per 1,000 ft$^2$ (92.9 m$^2$).

Golf traffic was simulated daily during the season using a modified traffic device with two 0.5 meter diameter rollers that spin at different speeds to create slipping motion. The rollers were fitted with SoftSpikes. The amount of spikes and passes used were designed to simulate 30,000 rounds of golf.

The turf was mowed seven times per week at 0.115" and clippings were collected. Fertility program included ammonium sulfate, iron sulfate and Primo MAXX™ plant growth regulator (available from Syngenta Crop Protection, Inc. Greensboro, N.C., U.S.A) applied every 7-10 days. Annual nitrogen rate was 2.5 lbs per 1000 sq feet, iron was applied at 2-4 ounces per application and Primo MAXX™ at 0.125 ounces of product per 1000 square feet per application. Straight sand topdressing (pH 8.0) was applied every 14 days, typically in conjunction with light vertical mowing or grooming.

Precipitation was such that supplemental irrigation was not required on a regular basis. Data were collected for turf quality and dollar spot disease rates. Data analysis was conducted using linear mixed models with compound symmetric covariance structure to assess treatment effects when repeated measurements were made on the same experimental unit over time. Treatment differences at individual measurement events were evaluated using analysis of variance and Fisher's protected least significant difference (LSD). The MIXED and GLM procedures in SAS/STAT software version 9.1 (SAS, Cary, N.C.) were used to perform the analyses.

TABLE 1

Treatment application regimes

| Treatment (Trt) # | Product | Rate/1000 (oz/1000) | Interval (days) |
|---|---|---|---|
| 1 | Untreated, fertilizer only | — | — |
| 2 | Emerald[a] | 0.13 | 21 |
| 3 | Emerald | 0.065 | 21 |
| 4 | Civitas[b] + Harmonizer[c] | 8/0.5 | 7 |
| 5 | Civitas + Harmonizer | 8/0.5 | 14 |
| 6 | Civitas + Harmonizer | 16/1 | 14 |
| 7 | Civitas + Harmonizer | 16/1 | 21 |

TABLE 1-continued

Treatment application regimes

| Treatment (Trt) # | Product | Rate/1000 (oz/1000) | Interval (days) |
|---|---|---|---|
| 8 | Civitas + Harmonizer | 12.75/1.8 | 21 |
| 9 | Civitas 1P | 17.3 | 14 |
| 10 | Civitas 1P | 17.3 | 21 |
| 11 | Emerald + Trt 4 | 0.13 | 21/7 |
| 12 | Emerald + Trt 5 | 0.13 | 21/14 |
| 13 | Emerald + Trt 6 | 0.13 | 21/14 |
| 14 | Emerald + Trt 7 | 0.13 | 21 |
| 15 | Emerald + Trt 8 | 0.13 | 21 |
| 16 | Emerald + Trt 9 | 0.13 | 21/14 |
| 17 | Emerald + Trt 10 | 0.13 | 21 |
| 18 | Emerald + Trt 4 | 0.065 | 21/7 |
| 19 | Emerald + Trt 5 | 0.065 | 21/14 |
| 20 | Emerald + Trt 6 | 0.065 | 21/14 |
| 21 | Emerald + Trt 7 | 0.065 | 21 |
| 22 | Emerald + Trt 8 | 0.065 | 21 |
| 23 | Emerald + Trt 9 | 0.065 | 21/14 |
| 24 | Emerald + Trt 10 | 0.065 | 21 |

[a] Emerald™ fungicide available from BASF Corporation, Research Triangle Park, NC, USA
[b] Civitas™ fungicide available from Petro-Canada, Mississauga, ON, Canada
[c] Civitas Harmonizer™ available from Petro-Canada, Mississauga, ON, Canada Dollar Spot Three periods of dollar spot infection were observed. Treatments were initiated about seven weeks prior to the first evidence of dollar spot pressure. Initially, dollar spot pressure was observed to be low; however, it was observed to increase to very high pressure by the 14th week of the study.

TABLE 2a

Effect of various treatments on number of dollar spots per plot.

| Treatment (Trt) # | Product | Rate/1000 (oz/1000) | Interval (days) | 27-Jul | 20-Aug | 4-Sep |
|---|---|---|---|---|---|---|
| 1 | Untreated, fertilizer only | — | — | 7.7 | 13.0 | 40.7 |
| 2 | Emerald | 0.13 | 21 | 0 | 0.7 | 10.7 |
| 3 | Emerald | 0.065 | 21 | 0 | 1.3 | 9.7 |
| 4 | Civitas + Harmonizer | 8/0.5 | 7 | 0 | 1.7 | 6.7 |
| 5 | Civitas + Harmonizer | 8/0.5 | 14 | 2.7 | 10.0 | 17.7 |
| 6 | Civitas + Harmonizer | 16/1 | 14 | 1.7 | 7.0 | 14.0 |
| 7 | Civitas + Harmonizer | 16/1 | 21 | 13.3 | 20.0 | 28.0 |
| 8 | Civitas + Harmonizer | 12.75/1.8 | 21 | 1.0 | 5.7 | 12.0 |
| 9 | Civitas 1P | 17.3 | 14 | 0.7 | 5.3 | 15.0 |
| 10 | Civitas 1P | 17.3 | 21 | 2.7 | 8.9 | 14.7 |
| 11 | Emerald + Trt 4 | 0.13 | 21/7 | 0 | 0 | 0.7 |
| 12 | Emerald + Trt 5 | 0.13 | 21/14 | 0 | 0 | 1.3 |
| 13 | Emerald + Trt 6 | 0.13 | 21/14 | 0 | 0 | 0 |
| 14 | Emerald + Trt 7 | 0.13 | 21 | 0 | 0 | 0 |
| 15 | Emerald + Trt 8 | 0.13 | 21 | 0 | 0.3 | 3.3 |
| 16 | Emerald + Trt 9 | 0.13 | 21/14 | 0 | 0 | 4.7 |
| 17 | Emerald + Trt 10 | 0.13 | 21 | 0 | 0 | 1.7 |
| 18 | Emerald + Trt 4 | 0.065 | 21/7 | 0 | 0 | 0 |
| 19 | Emerald + Trt 5 | 0.065 | 21/14 | 0 | 0 | 0 |
| 20 | Emerald + Trt 6 | 0.065 | 21/14 | 0 | 0.3 | 4.3 |
| 21 | Emerald + Trt 7 | 0.065 | 21 | 0 | 0 | 4.0 |
| 22 | Emerald + Trt 8 | 0.065 | 21 | 0 | 0.7 | 0.7 |
| 23 | Emerald + Trt 9 | 0.065 | 21/14 | 0 | 0 | 2.7 |
| 24 | Emerald + Trt 10 | 0.065 | 21 | 0 | 0 | 3.0 |
| | LSD (p = 0.05) | | | 6.8 | 9.5 | 14.8 |

Table 2a illustrates that neither boscalid alone nor CIVITAS alone are capable of sustained elimination of dollar spot, while the combined use of the boscalid and CIVITAS achieves this result, even with half the recommended application rate of boscalid.

Table 2b illustrates that the efficacy of the combination of Emerald and Civitas in treating dollar spot exceeds the expected efficacy, evidencing a synergistic effect. Applying the approach to identifying synergy as set out in S. R. Colby, "Calculating synergistic and antagonistic responses of herbicide combinations", Weeds 15, 20-22 (1967), expected efficacy, E, may be expressed as: $E = X + Y(100-X)/100$, where X is the efficacy, expressed in % of the untreated control, of the first composition (boscalid), and Y is the efficacy, expressed in % of the untreated control, of the second composition (Civitas). Table 2b sets out the expected and actual efficacies for treatments 18 and 19 of Table 2a, illustrating the synergistic effect found with half the recommended rate of boscalid application in combination with the lowest rate of Civitas application.

TABLE 2b

Synergistic effect of various treatments on number of dollar spots per plot.

| Trt # | 20-Aug Actual | 20-Aug Expected | 4-Sep Actual | 4-Sep Expected |
|---|---|---|---|---|
| 1 | 13.0 | | 40.7 | |
| 3 | 1.3 (90.0%) | | 9.7 (76.2%) | |
| 4 | 1.7 (86.9%) | | 6.7 (83.5%) | |
| 5 | 10.0 (23.1%) | | 17.7 (56.5%) | |
| 18 | 0 (100%) | 98.7%[a] | 0 (100%) | 96.1%[b] |
| 19 | 0 (100%) | 92.3%[c] | 0 (100%) | 89.6%[d] |

[a] $E = 90 + 86.9(100 - 90)/100$
[b] $E = 76.2 + 83.5(100 - 76.2)/100$
[c] $E = 90 + 23.1(100 - 90)/100$
[d] $E = 76.2 + 56.5(100 - 76.2)/100$

TABLE 3a

Effect of various treatments on season-long dollar spot infestation.

| Treatment (Trt) # | Product | Rate/1000 (oz/1000) | Interval (days) | DS |
|---|---|---|---|---|
| 1 | Untreated | — | — | 20.4 |
| 2 | Emerald | 0.13 | 21 | 3.8 |
| 3 | Emerald | 0.065 | 21 | 3.7 |
| 4 | Civitas + Harmonizer | 8/0.5 | 7 | 2.8 |
| 5 | Civitas + Harmonizer | 8/0.5 | 14 | 10.1 |
| 6 | Civitas + Harmonizer | 16/1 | 14 | 7.6 |
| 7 | Civitas + Harmonizer | 16/1 | 21 | 20.4 |
| 8 | Civitas + Harmonizer | 12.75/1.8 | 21 | 6.2 |

TABLE 3a-continued

Effect of various treatments on season-long dollar spot infestation.

| Treatment (Trt) # | Product | Rate/1000 (oz/1000) | Interval (days) | DS |
|---|---|---|---|---|
| 9 | Civitas 1P | 17.3 | 14 | 7.0 |
| 10 | Civitas 1P | 17.3 | 21 | 8.7 |
| 11 | Emerald + Trt 4 | 0.13 | 21/7 | 0.2 |
| 12 | Emerald + Trt 5 | 0.13 | 21/14 | 0.4 |
| 13 | Emerald + Trt 6 | 0.13 | 21/14 | 0 |
| 14 | Emerald + Trt 7 | 0.13 | 21 | 0 |
| 15 | Emerald + Trt 8 | 0.13 | 21 | 1.2 |
| 16 | Emerald + Trt 9 | 0.13 | 21/14 | 1.6 |
| 17 | Emerald + Trt 10 | 0.13 | 21 | 0.6 |
| 18 | Emerald + Trt 4 | 0.065 | 21/7 | 0 |
| 19 | Emerald + Trt 5 | 0.065 | 21/14 | 0 |
| 20 | Emerald + Trt 6 | 0.065 | 21/14 | 1.6 |
| 21 | Emerald + Trt 7 | 0.065 | 21 | 1.3 |
| 22 | Emerald + Trt 8 | 0.065 | 21 | 0.4 |
| 23 | Emerald + Trt 9 | 0.065 | 21/14 | 0.9 |
| 24 | Emerald + Trt 10 | 0.065 | 21 | 1.0 |

TABLE 3b

Synergistic effect of various treatments on season-long dollar spot infestation.

| Trt # | Actual | Expected |
|---|---|---|
| 1 | 20.4 | |
| 3 | 3.7 (81.9%) | |
| 4 | 2.8 (86.3%) | |
| 5 | 10.1 (50.5%) | |
| 18 (3 + 4) | 0 (100%) | 97.5%[a] |
| 19 (3 + 5) | 0 (100%) | 91.0%[b] |

[a] E = 81.9 + 86.3(100 − 81.9)/100
[b] E = 81.9 + 50.5(100 − 81.9)/100

Table 3b sets out the expected and actual efficacies for treatments 18 and 19 of Table 3a, illustrating the season-long synergistic effect found with half the recommended rate of boscalid application in combination with the lowest rate of Civitas application.

Turf Quality

Turf quality was assessed on three occasions using a scale of 1 to 9 (where 1=poor quality; 9=excellent quality; and 6=acceptable quality). Significant treatment effects were observed on each rating date and for the seasonal turfgrass quality ratings (Tables 4 and 5). As the study progressed, it was observed that the untreated plots struggled to maintain acceptable quality, mostly the result of severe natural infestations of dollar spot.

TABLE 4

Effect of various treatments on turfgrass quality ratings.

| Treatment (Trt) # | Product | Rate/1000 (oz/1000) | Interval (days) | 29-Jun | 17-Jul | 7-Aug |
|---|---|---|---|---|---|---|
| 1 | Untreated | — | — | 6.0 | 5.4 | 5.0 |
| 2 | Emerald | 0.13 | 21 | 6.0 | 5.6 | 6.0 |
| 3 | Emerald | 0.065 | 21 | 6.0 | 5.8 | 6.1 |
| 4 | Civitas + Harmonizer | 8/0.5 | 7 | 6.3 | 6.2 | 7.1 |
| 5 | Civitas + Harmonizer | 8/0.5 | 14 | 6.1 | 6.1 | 6.6 |
| 6 | Civitas + Harmonizer | 16/1 | 14 | 6.2 | 5.8 | 6.7 |
| 7 | Civitas + Harmonizer | 16/1 | 21 | 6.0 | 5.8 | 6.7 |
| 8 | Civitas + Harmonizer | 12.75/1.8 | 21 | 6.7 | 6.5 | 6.8 |
| 9 | Civitas 1P | 17.3 | 14 | 6.2 | 5.7 | 6.2 |
| 10 | Civitas 1P | 17.3 | 21 | 6.0 | 5.8 | 6.2 |
| 11 | Emerald + Trt 4 | 0.13 | 21/7 | 6.7 | 6.6 | 7.1 |
| 12 | Emerald + Trt 5 | 0.13 | 21/14 | 6.7 | 6.3 | 6.8 |
| 13 | Emerald + Trt 6 | 0.13 | 21/14 | 6.6 | 6.5 | 6.8 |
| 14 | Emerald + Trt 7 | 0.13 | 21 | 6.4 | 6.1 | 6.7 |
| 15 | Emerald + Trt 8 | 0.13 | 21 | 6.9 | 6.9 | 6.5 |
| 16 | Emerald + Trt 9 | 0.13 | 21/14 | 6.2 | 5.9 | 6.3 |
| 17 | Emerald + Trt 10 | 0.13 | 21 | 6.3 | 6.1 | 6.3 |
| 18 | Emerald + Trt 4 | 0.065 | 21/7 | 7.1 | 6.8 | 7.1 |
| 19 | Emerald + Trt 5 | 0.065 | 21/14 | 6.8 | 6.5 | 6.8 |
| 20 | Emerald + Trt 6 | 0.065 | 21/14 | 6.8 | 6.5 | 6.6 |
| 21 | Emerald + Trt 7 | 0.065 | 21 | 6.8 | 6.7 | 6.4 |
| 22 | Emerald + Trt 8 | 0.065 | 21 | 6.8 | 6.7 | 6.8 |
| 23 | Emerald + Trt 9 | 0.065 | 21/14 | 6.0 | 5.9 | 6.8 |
| 24 | Emerald + Trt 10 | 0.065 | 21 | 5.9 | 5.8 | 6.4 |
| | LSD (p = 0.05) | | | 0.6 | 0.8 | 0.3 |

TABLE 5

Effect of various treatments on season-long turfgrass quality ratings.

| Treatment (Trt) # | Product | Rate/1000 (oz/1000) | Interval (days) | TQ |
|---|---|---|---|---|
| 1 | Untreated, fertilizer only | — | — | 5.5 |
| 2 | Emerald | 0.13 | 21 | 5.9 |
| 3 | Emerald | 0.065 | 21 | 6.0 |
| 4 | Civitas + Harmonizer | 8/0.5 | 7 | 6.5 |
| 5 | Civitas + Harmonizer | 8/0.5 | 14 | 6.3 |
| 6 | Civitas + Harmonizer | 16/1 | 14 | 6.2 |
| 7 | Civitas + Harmonizer | 16/1 | 21 | 6.2 |
| 8 | Civitas + Harmonizer | 12.75/1.8 | 21 | 6.7 |
| 9 | Civitas 1P | 17.3 | 14 | 6.0 |
| 10 | Civitas 1P | 17.3 | 21 | 6.0 |
| 11 | Emerald + Trt 4 | 0.13 | 21/7 | 6.8 |
| 12 | Emerald + Trt 5 | 0.13 | 21/14 | 6.6 |
| 13 | Emerald + Trt 6 | 0.13 | 21/14 | 6.6 |
| 14 | Emerald + Trt 7 | 0.13 | 21 | 6.4 |
| 15 | Emerald + Trt 8 | 0.13 | 21 | 6.8 |
| 16 | Emerald + Trt 9 | 0.13 | 21/14 | 6.1 |
| 17 | Emerald + Trt 10 | 0.13 | 21 | 6.2 |
| 18 | Emerald + Trt 4 | 0.065 | 21/7 | 7.0 |
| 19 | Emerald + Trt 5 | 0.065 | 21/14 | 6.7 |
| 20 | Emerald + Trt 6 | 0.065 | 21/14 | 6.6 |
| 21 | Emerald + Trt 7 | 0.065 | 21 | 6.6 |
| 22 | Emerald + Trt 8 | 0.065 | 21 | 6.8 |
| 23 | Emerald + Trt 9 | 0.065 | 21/14 | 6.2 |
| 24 | Emerald + Trt 10 | 0.065 | 21 | 6.0 |

Tables 4 and 5 together illustrate that the combined use of boscalid at half the recommended rate and the lowest rate of Civitas application yielded the best results in terms of turfgrass quality, which was achieved while completely eliminating dollar spot as illustrated in Tables 2 and 3.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein.

The invention includes all embodiments and variations substantially as hereinbefore described and with reference to the examples.

What is claimed is:

1. A method of controlling a fungal pathogen of a plant, the method comprising applying to the plant an emulsifier, a paraffinic oil, a pigment, and boscalid, wherein the paraffinic oil, pigment, and boscalid are applied in amounts that are synergistically effective for controlling the fungal pathogen.

2. The method according to claim 1, further comprising mixing two or more of the paraffinic oil, the emulsifier, the pigment, and boscalid before applying to the plant.

3. The method according to claim 1, wherein the paraffinic oil comprises a paraffin having a number of carbon atoms ranging from about 16 to about 35.

4. The method according to claim 1, wherein the paraffinic oil comprises a paraffin having an average number of carbon atoms of about 23.

5. The method according to claim 1, wherein the paraffinic oil has a paraffin content of at least about 80%.

6. The method according to claim 1, wherein the paraffinic oil has a paraffin content of at least about 90%.

7. The method according to claim 1, wherein the paraffinic oil has a paraffin content of at least about 99%.

8. The method according to claim 1, wherein the method further comprises applying a silicone surfactant to the plant.

9. The method according to claim 1, wherein the pigment is a polychlorinated (Cu II) phthalocyanine.

10. The method according to claim 8, wherein the emulsifier comprises a natural or synthetic alcohol ethoxylate, an alcohol alkoxylate, an alkyl polysaccharide, a glycerol oleate, a polyoxyethylene-polyoxypropylene block copolymer, an alkyl phenol ethoxylate, a polymeric surfactant, a polyethylene glycol, a sorbitan fatty acid ester ethoxylate, or a combination thereof.

11. The method according to claim 8, wherein the emulsifier comprises a natural or synthetic alcohol ethoxylate, a polymeric surfactant, a sorbitan fatty acid ester, or a combination thereof, and the composition further comprises a polyethylene glycol according to formula IV:

wherein $R^1$=H or $CH_2$=CH—$CH_2$ or $COCH_3$; $R^2$=H or $CH_2$=CH—$CH_2$ or $COCH_3$; and f≥1.

12. The method according to claim 1, wherein the fungal pathogen is at least one of a fungus that causes dollar spot in turfgrass and a fungus that causes bentgrass dead spot or bermudagrass dead spot in a turfgrass.

13. The method according to claim 1, wherein the fungal pathogen is a fungus that blights leaf tissue in a turfgrass.

14. The method according to claim 1, wherein the fungal pathogen is a fungus that causes dollar spot in a turfgrass.

15. The method according to claim 1, wherein the fungal pathogen is selected from the group consisting of: *Sclerotinia homoeocarpa* and *Ophiosphaerella agrostis*.

16. The method according to claim 1, wherein the plant is one or more of: bentgrass, bluegrass, ryegrass, *fescue*, bermudagrass, bahiagrass, *zoysia*, beachgrass, wheatgrass or carpetgrass.

17. The method according to claim 1, wherein the plant is one or more of: creeping bentgrass, colonial bentgrass, perennial ryegrass, annual ryegrass, Kentucky bluegrass, common bermudagrass, hybrid bermudagrass, annual bluegrass, seashore *paspalum*, St. Augustinegrass, tall *fescue*, bahiagrass, zoysiagrass, centipedegrass, rough stalk bluegrass, buffalo grass, blue grama, or annual bentgrass.

18. The method according to claim 1, wherein the fungal pathogen is a fungus that causes bentgrass dead spot or bermudagrass dead spot in a turfgrass.

19. The method according to claim 1, wherein boscalid is applied to the plant at a rate from about 0.02 to about 0.12 oz per 1000 square feet.

20. The method according to claim 1, wherein the paraffinic oil is applied to the plant at a rate from about 0.9 to about 32 oz/1000 square ft.

* * * * *